United States Patent [19]
Torkkeli et al.

[11] Patent Number: 5,665,585
[45] Date of Patent: Sep. 9, 1997

[54] RECOMBINANT PRODUCTION OF GLUCOAMYLASE P IN TRICHODERMA

[75] Inventors: Tuula Torkkeli; Vesa Joutsjoki; Helena Torkkeli; Arja Vainio, all of Helsinki; Richard Fagerström, Espoo; Sirpa Aho; Matti Korhola, both of Helsinki, all of Finland; Helena Nevalainen, North Epping, Australia

[73] Assignee: Alko-Yhtiot Oy, Finland

[21] Appl. No.: 385,370

[22] Filed: Feb. 7, 1995

Related U.S. Application Data

[63] Continuation of Ser. No. 104,853, Aug. 12, 1993, abandoned, and a continuation-in-part of Ser. No. 937,789, Sep. 3, 1992, abandoned.

[51] Int. Cl.⁶ .................. C12N 1/15; C12N 9/30; C12N 15/56
[52] U.S. Cl. .................. 435/203; 435/69.1; 435/172.3; 435/183; 435/201; 435/210; 435/254.6; 435/256.8; 435/320.1; 536/23.1; 536/23.2; 536/23.74
[58] Field of Search .................. 435/69.1, 183, 435/201, 203, 210, 254.6, 256.8, 172.3, 320.1; 536/23.1, 23.2, 23.74

[56] References Cited

U.S. PATENT DOCUMENTS

| | | | |
|---|---|---|---|
| 4,211,842 | 7/1980 | Marshall | 435/210 |
| 4,234,686 | 11/1980 | Marshall | 435/94 |
| 4,318,927 | 3/1982 | Marshall | 426/11 |
| 4,318,989 | 3/1982 | Marshall | 435/205 |
| 4,684,525 | 8/1987 | Plainer et al. | 426/16 |
| 4,746,517 | 5/1988 | Ducroo | 426/12 |
| 4,794,175 | 12/1988 | Nunberg et al. | 536/27 |
| 4,863,864 | 9/1989 | Ashikari et al. | 435/205 |
| 4,898,738 | 2/1990 | Yamamoto et al. | 426/17 |
| 4,898,820 | 2/1990 | Hitoshio et al. | 435/95 |
| 4,921,795 | 5/1990 | Bozich, Jr. | 435/96 |
| 4,925,795 | 5/1990 | Takasaki | 435/95 |
| 4,931,389 | 6/1990 | Kobayashi et al. | 435/95 |
| 4,937,193 | 6/1990 | Hinchliffe et al. | 435/172.3 |
| 4,971,906 | 11/1990 | Melasnimei et al. | 435/98 |
| 5,024,941 | 6/1991 | Maine et al. | 435/69.9 |

FOREIGN PATENT DOCUMENTS

| | | |
|---|---|---|
| 0 126 206 A3 | 11/1984 | European Pat. Off. . |
| 0 126 206 B1 | 11/1984 | European Pat. Off. . |
| 0 186 066 A1 | 2/1986 | European Pat. Off. . |
| 0 185 327 A2 | 6/1986 | European Pat. Off. . |
| 0 244 234 A2 | 4/1987 | European Pat. Off. . |
| 0 228 254 A3 | 8/1987 | European Pat. Off. . |
| 0 257 115 A1 | 3/1988 | European Pat. Off. . |
| 0 260 404 A2 | 3/1988 | European Pat. Off. . |
| 0 362 179 A3 | 4/1990 | European Pat. Off. . |
| 0 372 184 A1 | 6/1990 | European Pat. Off. . |
| 0 405 283 A2 | 1/1991 | European Pat. Off. . |
| 0 418 835 A1 | 3/1991 | European Pat. Off. . |
| 0 450 627 A2 | 10/1991 | European Pat. Off. . |
| WO 86/07091 | 12/1986 | WIPO . |
| WO 88/09795 | 12/1988 | WIPO . |
| WO92/06209 | 4/1992 | WIPO . |

OTHER PUBLICATIONS

Boel, E. et al., "Two different types of intervening sequences in the glucoamylase gene from *Aspergillus niger*,"*EMBO J.* 3:1581–1585 (1984).

McCleary, B.V. et al., "Hydrolysis of αD–Glucans and α–D–Gluco–Oligosaccharides by *Cladosporium resinae* Glucoamylases," *Carbohyd. Res.* 86:77–96 (1980).

Hayashida, Shinsaku et al., "Molecular Cloning of the Glucoamylase I Gene of *Aspergillus awamori* var. *kawachi* for Localization of the Raw–starch–affinity Site," *Agric. Biol. Chem.* 53(4):923–929 (1989).

Hata, Y. et al., "Nucleotide sequence and expression of the glucoamylase–encoding gene (glaA) from *Aspergillus oryzae*," *Gene* 108:145–150 (1991).

Ohnishi, H. et al., "Molecular cloning of a glucoamylase gene from a thermophilic *Clostridium* and kinetics of the cloned enzyme," *Eur. J. Biochem.* 207:413–418 (1992).

Shibuya, I. et al., "Molecular Cloning of the Glucoamylase Gene of *Aspergillus shirousami* and Its Expression in *Aspergillus oryzae*," *Agric. Biol. Chem.* 54(8):1905–1914 (1990).

Roberts, I.N. et al., "Heterotogous gene expression in *Aspergillus niger*: a glucoamylase–porcine pancreatic prophospholipase $A_2$ fusion protein is secreted and processed to yield mature enzyme." *Gene* 122:155–161 (1992).

Ward, M. et al., "Improved Production Of Chymosin In *Aspergillus* By Expression As A Glucoamylase–Chymosin Fusion," *Bio/Technol.* 8:435–440 (May, 1990).

Manjunath, P. et al., "Review—Fungal Glucoamylases," *J. Appl. Biochem.* 5:235–260 (1983).

Joutsjoki, V.V. et al., "Glucoamylase P gene of *Hormoconis resinae*: Molecular cloning, sequencing and introduction into *Trichoderma reesei*," *FEMS Microbiol. Letts.* 90:237–244 (1992).

Joutsjoki, V.V. et al., "A Novel Glucoamylase Preparation For Grain Mash Saccharification," *Biotechnol. Letts.* 15(3):277–282 (Mar. 1993).

Vainio, A.E.I. et al., "Cloning and expression of *Hormoconis resinae* glucoamylase P cDNA in *Saccharomyces cerevisiae*," *Curr. Genet.* 24:38–44 (1993).

Joutsjoki, V.V. et al., "Transformation of *Trichoderma reesei* with *Hormoconis resinae* glucoamylase P (gamP) gene: production of a heterotogous glucoamylase by *Trichoderma reesei*," *Curr. Genet* 24: 223–228 (1993).

Joutsjoki, V.V. et al., "Secretion of the *Hormoconis resinae* glucoamylase P enzyme from *Trichoderma reesei* directed by the natural and the cbh1 gene secretion signal," *FEMS Microbiol. Letts.* 112:281–286 (1993).

(List continued on next page.)

*Primary Examiner*—John L. LeGuyader
*Attorney, Agent, or Firm*—Sterne, Kessler, Goldstein & Fox p.l.l.c.

[57] ABSTRACT

The invention is directed to amino acid and DNA sequences of a unique glucoamylase P that has a high debranching activity, a Trichoderma host cell, transformed with such sequences, the expression of such recombinant glucoamylase P, and the industrial uses for the recombinant enzyme and hosts transformed therewith.

35 Claims, 23 Drawing Sheets

OTHER PUBLICATIONS

Contreras, R. et al., "Efficient KEX2–Like Processing Of A Glucoamylase–Interleukin–6 Fusion Protein By *Aspergillus Nidulans* And Secretion Of Mature Interleukin–6," *Bio/Technol.* 9:378–381 (Apr. 1991).

Torkketi, H. et al., "Cloning of *Hormoconis Resinae* Glucoamylase cDNA in *Saccharomyces Cerevisiae,*" XIII Intern. Specialized Symp. on Yeasts, Sep. 18–22, 1989, Leuven, Belgium.

Itoh, T. et al., "Nucleotide Sequence of the Glucoamylase Gene GLU1 in the Yeast *Saccharomycopsis fibuligera,*" *J. Bacteriol.* 169:4171–4176 (1987).

Itoh, T. et al. "Construction and Characterization of Mutant Glucoamylases from the Yeast *Saccharomycopsis fibuligera,*" *Agric. Biol. Chem.* 53(12):3159–3167 (1989).

Derwent Biotechnology Abstracts 1992–1991/Nov. Abstract of Delgado, M.A. et al., "Transformation of brewing yeast: use of a vector conferring resistance to cycloheximide—*Saccharomyces cerevisiae* transformation with vector plasmid YEpCR20 to give transformant with cycloheximide–resistance," Abs. 122361/7, *J. Inst. Brew.* 97(3): (1991).

Nevatainen, K.M.H., et al., "Molecular Industrial Mycology—Systems and Applications for Filamentous Fungi," Mycology Series (8), ed. Sally A. Leong and Berka, R.M, Marcel Dekker, Inc. pub., New York, 1991, pp. 129–147.

Harkki, A. et al., "A Novel Fungal Expression System: Secretion of Active Calf Chymosin from the Filamentous Fungus *Trichoderma reesei* " *Bio/Technol.* 7:596–601 (1989).

Montenecourt, B.S. et al., "Preparation of Mutants of *Trichoderma reesei* with Enhanced Cellulase Production," *Appl. Environ. Microbiol.* 34(6):777–782 (1977).

Dowman, M.G. et al., "The Use of Enzymes to Predict the Digestibility of Animal Feeds," *J. Sci. Food Agric.* 33:689–696 (1982).

Abe, A. et al., "Application of Enzymatic Analysis With Glucoamylase, Pronase and Cellulase to Various Feeds for Cattle," *J. Animal Sci.* 48(6):1483–1490 (1979).

Fagerström, R. et al., "Comparison of two glucoamylases from *Hormoconis resinae,*" *J. Gen. Microbiol.* 136:913–920 (1990).

Fagerström, R. "Subsite mapping of *Hormoconis resinae* glucoamylases and their inhibition by gluconolactone," *J. Gen. Microbiol.* 137:1001–1008 (1991).

Nunberg, J.H. et al., "Molecular Cloning and Characterization of the Glucoamylase Gene of *Aspergillus awamori,*" *Mol. and Cell. Biol.* 4(11):2306–2315 (1984).

Chen, L. et al., "Deletion Analysis of the Native–Starch–Binding Region of *Aspergillus* Glucoamylase in β–Galactosidase Fusion Proteins," *Am, Soc. Microbiol.* 90:269 Abstract 0–36 (1990).

Svensson, B. et al., "The complete amino acid sequence of the glycoprotein, glucoamylase G1, from *Aspergillus niger,*" *Carlsberg Res. Commun.* 48:529–544 (1983).

Derwent Biotechnol. Abs. 1982–1991/Nov. Abstract of Hata, Y. et al., "The glucoamylase cDNA from *Aspergillus oryzae:* its cloning, nucleotide sequence, and expression in *Saccharomyces cerevisiae*—purification and DNA sequence," *Biol. Chem.* 55(4):941–949 (1991).

Derwent Biotechnology Abs. 1982–1991/Nov. Abstract of Shibuya, I. et al., "Molecular cloning of the glucoamylase gene of *Aspergillus shirousami* and its expression in *Aspergillus oryzae*—recombinant enzyme production," *Agric. Biol. Chem.* 54(8):1905–1914 (1990).

Derwent Biotechnology Abs. 1982–1991/Nov. Abstract of Evans, R. et al., "*Activity and thermal stability of genetically truncated forms of Aspergillus glucoamylase*—site–directed mutagenesis and enzyme engineering; gene cloning and expression in *Saccharomyces cerevisiae,*" *Gene* 91(1):131–134 (1990).

Shen, G–J. et al., "Physiological and enzymatic characterization of a novel pullulan–degrading thermophilic *Bacillus* strain 3183," *Appl. Microbiol. Biotechnol.* 33:340–344 (1990).

Ashikari, T. et al., "*Rhizopus* Raw–Starch–Degrading Glucoamylase: Its Cloning and Expression in Yeast," *Agric. Biol. Chem.* 50 (4):957–964 (1986).

Ashikari, T. et al., "Direct fermentation of raw corn to ethanol by yeast transformants containing a modified *Rhizopus* glucoamylase gene," *Appl. Microbiol. Biotechnol.* (32):129–133 (1989).

Yamashita, I. et al., "Nucleotide Sequence of the Extracellular Glucoamylase Gene STA1 in the Yeast *Saccharomyces diastaticus,*" *J. Bacteriol.* 161(2):567–573 (1985).

Derwent Biotechnol. Abs. 1982–1991/Nov. Abstract of Gellissen, G. et al., "Heterologous germ expression in *Hansenula polymorpha:* efficient secretion of glucoamylase—*Schwanniomyces occidentalis* glucoamylase GAM1 gene cloning and plasmid pFMDGAM construction," *Bio/Technology* 9(3):291–295 (1991).

Lee, E.Y.C. et al., "Purification and Properties of Yeast Amylo–1,6–glucosidase–Oligo–1,4→1,4–glucantransferase," *Biochem.* 9(11):2347–2355 (1970).

Dohmen, R.J. et al., "Cloning of the *Schwanniomyces occidentalis* glucoamylase gene (GAM1) and its expression in *Saccharomyces cerevisiae,*" *Gene* 95:111–121 (1990).

Linardi, V.R. et al., "Production of amylases by yeasts," *Can. J. Microbiol.* 36(11):751–3 (1990).

Derwent Biotechnol. Abs. 1982–1991/Nov. Abstract of "New gene cloning, vector and transformant—*Aspergillus usamii* mut. shirousamii acid–tolerant glucoamylase expression in *Saccharomyces cerevisiae* and *Aspergillus oryzae;* potential rice saccharification and ethanol production," JP 88273172 (Kokuzeicho–Chokan).

Derwent Biotechnol. Abs. 1982–1991/Nov. Abstract of "Microorganism transformation—*Saccharomyces cerevisiae* transformation using linear segment, free of unwanted vector sequences, containing *Saccharomyces diastaticus* glucoamylase gene and selectable marker gene," WO90/US/2776 (Infergene).

Derwent Biotechnol. Abs. 1982–1991/Nov. Abstract of "Production of recombinant *protein in eukaryote e.g. Saccharomyces*, Kluyveromyces, Hansenula, Aspergillus, Rhizopos or *Trichoderma* spp.—abzyme (catalytic antibody) or recombinant enzyme e.g. oxidase production using multicopy expression vector," WO 90/EP/1138 (Unlever).

World Food & Drink Report (WFR), "UK—Genetic Engineering of Yeast To Produce Low Calorie Beer," p. 1, Jan. 5, 1987.

Manialis et al. Molecular Cloning: A Laboratory Manual, Cold Spring Harbor Lab., CSH, N.Y. 1982 (pp. 212–229, 404–414, 422–423 & 430–431.

Pentila et al. Gene 61:155–164 (1987).

```
TTCCCGGTTA CTTCCAGACT CATCTCATCA TGCGCCTCCT CCCCTCGTCG   50
TGTGCAGGGG CTCTCTCTTT GCTCTGCTCC CTGGCGATCG CAGCACCTAC  100
GGAATTGAAA GCCAGAGATT TGAGCTCTTT TATAGCTTCA GAGAGAGCAA  150
TTGCATTGCA GGGCGCGCTC AATAACATTG GACCCGATGG CTCAGCAGTA  200
CCAGGGGCTG GAGCGGGCTT CGTAGTCGCA AGTCCTTCAA AGGCCAATCC  250
CGATTACTTC TACACATGGA GTCGGGACTC AGCCTTGACA TTGAAAATGA  300
TCATTGATGA GTTTATCCTT GGAAACACCA CCCTCCAGAC GATAATCGAA  350
CAATATATCC ATGCCCAAGC AGTTCTTCAG ACCGTTTCCA ATCCATCTGG  400
AACCTTCCTG CCTGACGGTG TCGGATTAGG AGAGCCAAAG TTCATGGTCG  450
ATGGAACTCG GTTCAATGGG CCTTGGGGAC GGCCTCAACG TGACGGCCCA  500
GCTCTCCGCG CTATTGCCTT AATGACCTAT AGTAATTGGC TCATTAAGAA  550
TGGTCAATTT GCGGAGGCCA AGACAAAGAT ATGGCCCATT ATTGCCAACG  600
ATCTCTCATA CGTGGGACAA TATTGGAACC AGAGTGGTTT TGACCTTTGG  650
GAAGAAACTT ACGCATCCAG CTTCTTCACC ATCCAGAACC AGCACCGAGC  700
TCTTGTCGAG GGTGCGCAGC TCGCCCATGA TCTCGGTGTC ACATGTACAG  750
GCTGTGACCA GGCACCGGAG GTTCTCTGCT TCCTCCAAAG TTTCTGGAAC  800
GGTAAATACA TCGTGTCGAA CATCAACGTC AATAACGGCC GAACTGGCTT  850
GGATGGAAAC TCCATACTAG GGGCCATCTC AACTTTTGAT ATCGATGCGT  900
ACTGCGATAG TCCAACCTTG CAACCTTGCC ATAGCCAGTC TTTGGCAAAT  950
TTCAAGGTCT TGACAGACAC TTTTAGGAAC TTGTATACCA TCAACGCTGG 1000
CATTCCGGAA GGCCAAGGGG TAGCTGTCGG GAGATACGCC GAGGACGTTT 1050
ACATGGGCGG TAATCCATGG TATCTGATCA CCACCGCAGC AGCAGAGTTC 1100
TTGTATGATG CAGTAGCACA GTGGAAGGCT CGTCATGTGC TCACCGTTGA 1150
CGAGACGTCT CTCGCATTCT TCAAAGATAT CTACCCCGAA GTCACCGTCC 1200
GCGAGTACAA AAGCGGGAAC GCCAACAGCC CATTCGCACA GATCATGGAT 1250
GCTGTGACCG CCTACGCCGA CTCGTACGTC GCCATCGCCG AGAAATACAT 1300
CCCCTCCAAC GGATCCCTCT CGGAGCAATT CAACCGCGAT ACAGGAACCC 1350
CCCTATCCGC CATCGACCTC ACCTGGTCCT ACGCCGCCTT CATAACCATG 1400
TCTCAACGCC GCGCCGGCCA ATACCCCAGC AGCTGGGGCT CCCGCAACGC 1450
CTTGCCGCCT CCTACCACCT GCTCCGCCAG CTCCACCCCG GCATCTACA  1500
CCCCCGCCAC CGCCGCCGGC GCCCCAACG TAACATCCAG CTGCCAGGTC 1550
AGCATCACCT TCAACATCAA CGCCACCACC TACTACGGCG AGAACCTCTA 1600
CGTGATCGGT AACTCGTCAG ATCTGGGCGC CTGGAATATC GCCGATGCGT 1650
ACCCGCTCAG CGCCAGTGCA TATACGCAGG ACCGCCCGCT CTGGAGTGCC 1700
GCTATCCCGT TGAATGCGGG TGAGGTTATT AGCTATCAGT ATGTGCGCCA 1750
GGAAGACTGT GATCAGCCGT ATATATACGA GACGGTTAAT CGCACCCTGA 1800
CGGTACCCGC GTGTGGAGGC GCGGCTGTCA CTACGGATGA TGCGTGGATG 1850
GGACCGGTGG GCTCATCTGG GAATTGCTGA AGGGGGTTTG GGTTTGGGA  1900
TTGAAGATAG ATAGATGGAG ATTTAGATCT GGTTAATTAC TGGGTTTATA 1950
AACTTACGTG CATTCAGTAA TTCATGGGTT TTGCAAAAAA AAAAAA     1996
```

FIG.5

```
Met Arg Leu Leu Pro Ser Ser Cys Ala Gly Ala Leu Ser Leu Leu
             5                  10                  15
Cys Ser Leu Ala Ile Ala Ala Pro Thr Glu Leu Lys Ala Arg Asp
            20                  25                  30
Leu Ser Ser Phe Ile Ala Ser Glu Arg Ala Ile Ala Leu Gln Gly
            35                  40                  45
Ala Leu Asn Asn Ile Gly Pro Asp Gly Ser Ala Val Pro Gly Ala
            50                  55                  60
Gly Ala Gly Phe Val Val Ala Ser Pro Ser Lys Ala Asn Pro Asp
            65                  70                  75
Tyr Phe Tyr Thr Trp Ser Arg Asp Ser Ala Leu Thr Leu Lys Met
            80                  85                  90
Ile Ile Asp Glu Phe Ile Leu Gly Asn Thr Thr Leu Gln Thr Ile
            95                 100                 105
Ile Glu Gln Tyr Ile His Ala Gln Ala Val Leu Gln Thr Val Ser
           110                 115                 120
Asn Pro Ser Gly Thr Phe Leu Pro Asp Gly Val Gly Leu Gly Glu
           125                 130                 135
Pro Lys Phe Met Val Asp Gly Thr Arg Phe Asn Gly Pro Trp Gly
           140                 145                 150
Arg Pro Gln Arg Asp Gly Pro Ala Leu Arg Ala Ile Ala Leu Met
           155                 160                 165
Thr Tyr Ser Asn Trp Leu Ile Lys Asn Gly Gln Phe Ala Glu Ala
           170                 175                 180
Lys Thr Lys Ile Trp Pro Ile Ile Ala Asn Asp Leu Ser Tyr Val
           185                 190                 195
Gly Gln Tyr Trp Asn Gln Ser Gly Phe Asp Leu Trp Glu Glu Thr
           200                 205                 210
Tyr Ala Ser Ser Phe Phe Thr Ile Gln Asn Gln His Arg Ala Leu
           215                 220                 225
Val Glu Gly Ala Gln Leu Ala His Asp Leu Gly Val Thr Cys Thr
           230                 235                 240
Gly Cys Asp Gln Ala Pro Glu Val Leu Cys Phe Leu Gln Ser Phe
           245                 250                 255
Trp Asn Gly Lys Tyr Ile Val Ser Asn Ile Asn Val Asn Asn Gly
           260                 265                 270
Arg Thr Gly Leu Asp Gly Asn Ser Ile Leu Gly Ala Ile Ser Thr
           275                 280                 285
Phe Asp Ile Asp Ala Tyr Cys Asp Ser Pro Thr Leu Gln Pro Cys
           290                 295                 300
His Ser Gln Ser Leu Ala Asn Phe Lys Val Leu Thr Asp Thr Phe
           305                 310                 315
Arg Asn Leu Tyr Thr Ile Asn Ala Gly Ile Pro Glu Gly Gln Gly
```

FIG. 5A

```
                        320                 325                 330
        Val Ala Val Gly Arg Tyr Ala Glu Asp Val Tyr Met Gly Gly Asn
                        335                 340                 345
        Pro Trp Tyr Leu Ile Thr Thr Ala Ala Ala Glu Phe Leu Tyr Asp
                        350                 355                 360
        Ala Val Ala Gln Trp Lys Ala Arg His Val Leu Thr Val Asp Glu
                        365                 370                 375
        Thr Ser Leu Ala Phe Phe Lys Asp Ile Tyr Pro Glu Val Thr Val
                        380                 385                 390
        Arg Glu Tyr Lys Ser Gly Asn Ala Asn Ser Pro Phe Ala Gln Ile
                        395                 400                 405
        Met Asp Ala Val Thr Ala Tyr Ala Asp Ser Tyr Val Ala Ile Ala
                        410                 415                 420
        Glu Lys Tyr Ile Pro Ser Asn Gly Ser Leu Ser Glu Gln Phe Asn
                        425                 430                 435
        Arg Asp Thr Gly Thr Pro Leu Ser Ala Ile Asp Leu Thr Trp Ser
                        440                 445                 450
        Tyr Ala Ala Phe Ile Thr Met Ser Gln Arg Arg Ala Gly Gln Tyr
                        455                 460                 465
        Pro Ser Ser Trp Gly Ser Arg Asn Ala Leu Pro Pro Pro Thr Thr
                        470                 475                 480
        Cys Ser Ala Ser Ser Thr Pro Gly Ile Tyr Thr Pro Ala Thr Ala
                        485                 490                 495
        Ala Gly Ala Pro Asn Val Thr Ser Ser Cys Gln Val Ser Ile Thr
                        500                 505                 510
        Phe Asn Ile Asn Ala Thr Thr Tyr Tyr Gly Glu Asn Leu Tyr Val
                        515                 520                 525
        Ile Gly Asn Ser Ser Asp Leu Gly Ala Trp Asn Ile Ala Asp Ala
                        530                 535                 540
        Tyr Pro Leu Ser Ala Ser Ala Tyr Thr Gln Asp Arg Pro Leu Trp
                        545                 550                 555
        Ser Ala Ala Ile Pro Leu Asn Ala Gly Glu Val Ile Ser Tyr Gln
                        560                 565                 570
        Tyr Val Arg Gln Glu Asp Cys Asp Gln Pro Tyr Ile Tyr Glu Thr
                        575                 580                 585
        Val Asn Arg Thr Leu Thr Val Pro Ala Cys Gly Gly Ala Ala Val
                        590                 595                 600
        Thr Thr Asp Asp Ala Trp Met Gly Pro Val Gly Ser Ser Gly Asn
                        605                 610                 615
        Cys
```

FIG.5B

-291
cctccgcttcttccctcttcccacttcccagggaatgacctttcgtgctacggcgcgcaaccagtcatctcacgatgttgccgcaattgaatcggtc
                                                                                            -200
cgttcaggtttatccgtcaacaagctttaagctttttcaggcttcggggtcgagtggagtaatcgagccatcgtgggagagacaagctcactaggaggcgg
                                                                                            -100
cggggaagttggatattgtgaacatataagagcatgtgctcgttcgttctagctacaatgacttcattcgttttattgttacttccagactcatctcatCATGCGC
                                                                                            +1                M  R
                                                                                            100
CTCCTCCCCTCTGTGTGCAGGGGCTCTCTCTTTGCTCTCGCATCCCCTGGGCTCTGGCGATCGCAGCACTACGGAATTGAAAGCCAGAGATTTGAGCTCTTTTATAG
 L  L  P  S  S  C  A  G  A  L  S  L  L  C  S  L  A  I  A  A  P  T  E  L  K  A  R  *  D  L  S  S  F  I
                                          150                                               200
CTTCAGAGAGAGCAATTGCATTGCAGGGCGCTCAATAACATTGGACCCGATGGCTCAGCAGTACCAGGGCTCTGGAGCGGGGCTTCGTAGTCGCAAGTCC
 A  S  E  R  A  I  A  L  Q  G  A  L  N  N  I  G  P  D  G  S  A  V  P  G  A  G  F  V  V  A  S  P
                                          250                                               300
TTCAAAGGCCAATCCGATTgtcagtaccatctacaaacatcttccttaccacgagtcaggaatcccagttgcgtgtactgactatcattagACTTCTA             Y  F  Y
 S  K  A  N  P  D
                     IVS 1
                                          350                                               400
CACATGGAGTCGGGACTCAGCTTGACATTGAAAATGATCATTGATGAGTTTATCCTTGGAAACACCACCCTCCAGACGATAATCGAACAATATATCCAT
 T  W  S  R  D  S  A  L  T  L  K  M  I  I  D  E  F  I  L  G  N  T  T  L  Q  T  I  I  E  Q  Y  I  H
                                          450                                               500
GCCCAAGCAGTTCTTCAGACCGTTTCCAATCCATCTGGAACCTTCCTGCCTGACGGTGTCGGATTAGGAGAGCCAAAGTTCATGGTCGATGGAACTCGGT
 A  Q  A  V  L  Q  T  V  S  N  P  S  G  T  F  L  P  D  G  V  G  L  G  E  P  K  F  M  V  D  G  T  R
                                          550                                               600
TCAATGGGCCTTGGGGACGGCCCTCAACGTGACGGCCCAGCTCTCCGGCTATTGCCTTAATGACCTATAGTAATTGGCTCATTAAGAATGGTCAATTTgt
 F  N  G  P  W  G  R  P  Q  R  D  G  P  A  L  R  A  I  A  L  M  T  Y  S  N  W  L  I  K  N  G  Q  F

FIG.13A

```
                                                           700
aaggatctcctgtgaacagtgtcgtctggtatagatggatccatgagctatcactcctgcctcagacagtctctcaggttaacctgtgtcttaactca
                                     IVS 2                                                    800
tgaatctccttgccctaggatattgagagtcttttggtccaatcaagcaattgctaattccttgttgtctagGCGGAGGCCAAGACAAAGATATGGCC
                                                                         A  E  A  K  T  K  I  W  P
                                                                                               900
CATTATTGCCAACGATCTCTCATACGTGGGACAATATTGGAAGAGAGTGGTTTGACCTTTGGGAAGAAACTTACGCATCCAGCTTCTTCACCATCCAG
 I  I  A  N  D  L  S  Y  V  G  Q  Y  W  N  Q  S  G  F  D  L  W  E  E  T  Y  A  S  S  F  F  T  I  Q
                           950                                                   1000
AACCAGCACCGAGCTCTTGTCGAGGGTGCGCAGCTCGCCATGCACGATCTCGGTGTCACATGTACAGGCTGTGACCAGGCACCGGAGGTTCTCTGCTTCCTCC
 N  Q  H  R  A  L  V  E  G  A  Q  L  A  H  D  L  G  V  T  C  T  G  C  D  Q  A  P  E  V  L  C  F  L
                                      1050                                                   1100
AAAGTTTCTGGAACGGTAAATACATCGTGTCGAACATCAATAACGGCCGAACTGGCTTGGATGGAAACTCCATACTAGGGGCCATCTCAACTTT
 K  V  S  G  N  G  K  Y  I  V  S  N  I  N  V  N  N  G  R  T  G  L  D  G  N  S  I  L  G  A  I  S  T  F
                                            1150                                                   1200
TGATATCGATGCGTACTGCGATAGTCCAACCTTGCAACCTTGCCATAGCCAGTCTTTGGCAAATTTCAAGGTCTTGACAGACACTTTTAGGAACTTGTAT
 D  I  D  A  Y  C  D  S  P  T  L  Q  P  C  H  S  Q  S  L  A  N  F  K  V  L  T  D  T  F  R  N  L  Y
                                             1250                                                   1300
ACCATCAACGCTGGCATTCCGGAAGGCCAAGGGGTAGCTGTCGGGGAGATACGCCGAGGAGTTTACATGGGCGGTAATCCATGgttggttttccgtggttt
 T  I  N  A  G  I  P  E  G  Q  G  V  A  V  G  R  Y  A  E  D  V  Y  M  G  G  N  P  W
                                               1350                                                    1400
tgccctcatcaatccgtacagtaactgactgatagGTATCTGATCACCACCGCAGCAGCAGAGTTCTTGTATGATGCAGTAGCACAGTGGAAGGCTCGT
  IVS 3                              Y  L  I  T  T  A  A  A  E  F  L  Y  D  A  V  A  Q  W  K  A  R
                                                 1450                                                    1500
CATGTGCTCACCGTTGACGAGACGTCTCTCGCATTCTTCAAAGATATCTACCCCGAAGTCACCGTCCGGAGTACAAAAGGGGAACGCCAACAGCCCAT
 H  V  L  T  V  D  E  T  S  L  A  F  F  K  D  I  Y  P  E  V  T  V  R  E  Y  K  S  G  N  A  N  S  P
```

FIG. 13B

```
1600
TCGGCACAGATCATGGATGCTGTGACCGCCTACGCCGACTCGTACGTCGCCATCGCCGAGAAATACATCCCCTCCAACGATCCCTCTCGGAGCAATTCAA
 F  A  Q  I  M  D  A  V  T  A  Y  A  D  S  Y  V  A  I  A  E  K  Y  I  P  S  N  G  S  L  S  E  Q  F  N
                                                      1650                                    1700
CCCGGATACAGGAACCCCCTCATCCGCCATCGACCTCACCTGGTCCTACGCCTTCATAACCATGTCTCATAACGCCGGCCAATACCCCAGCAGC
 R  D  T  G  T  P  L  S  A  I  D  L  T  W  S  Y  A  A  F  I  T  M  S  Q  R  R  A  G  Q  Y  P  S  S
                            1750                                    1800
TGGGGCTCCCGCAACGCCTTGCCGCCTCCTACCACCTGCTCCGCCAGTCTCCACCCCGGCATCTACACCCCGGCCACCGCCGCCCCAACGTAA
 W  G  S  R  N  A  L  P  P  P  T  T  C  S  A  S  S  T  P  G  I  Y  T  P  A  T  A  A  G  A  P  N  V
                1850                                    1900
CATCCAGCTGCCAGGTCAGCATCACCTTCAACATCAACGCCACCACTACGGCGGAGAACCTCTACGTGATCGGTAACTCGTCAGATCTGGGCGCCTG
 T  S  S  C  Q  V  S  I  T  F  N  I  N  A  T  T  Y  Y  G  E  N  L  Y  V  I  G  N  S  S  D  L  G  A  W
    1950                                    2000
GAATATCGCCGATGCGTACCCGCTCAGCGCCAGTGCATATACGGACCAGGACCGCCCGCTCTGGAGTGCCGCTATCCCGTTGAATGCGGGTGAGGTTATTAGC
 N  I  A  D  A  Y  P  L  S  A  S  A  Y  T  Q  D  R  P  L  W  S  A  A  I  P  L  N  A  G  E  V  I  S
                    2050                                    2100
TATCAGTATGTGCGCCAGGAAGACTGTGATCAGCCGTATATATACGAGACGGTTAATCGCACCCTGACGGTACCCGCGTGTGGAGGCGCGGCTCTCACTA
 Y  Q  Y  V  R  Q  E  D  C  D  Q  P  Y  I  Y  E  T  V  N  R  T  L  T  V  P  A  C  G  G  A  A  V  T
                            2150                                    2200
CGGATGATGCGTGGATGGGACCGGTTGGGCTCATCTGGAATTGCTGAagggggtttgggattgaagatagatgagatttagatctggt
 T  D  D  A  W  M  G  P  V  G  S  S  G  N  C  STOP
                                    2250                                    2300
taattactgggtttataactttacgtgcattcagtaattcatgggtttgcaaatctgattctcatataagatatgaatatgtaggacctttctctctt
                    2350                                    2400
cgcattgctgcttcctttgcagaacaaaaggggggaaaaggcgttacacatacgagtccgagtccccgcgaatcaagactgggggattagatatctataat
            2450
gggggattctgcttctcccgccgagtcatcagaaggggggagtccc
```

FIG. 13C

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 1996 base pairs
( B ) TYPE: nucleic acid
( C ) STRANDEDNESS: both
( D ) TOPOLOGY: both ( x i ) SEQUENCE DESCRIPTION: SEQ ID NO:1:

| | | | | | |
|---|---|---|---|---|---|
| TTCCCGGTTA | CTTCCAGACT | CATCTCATCA | TGCGCCTCCT | CCCCTCGTCG | TGTGCAGGGG | 60 |
| CTCTCTCTTT | GCTCTGCTCC | CTGGCGATCG | CAGCACCTAC | GGAATTGAAA | GCCAGAGATT | 120 |
| TGAGCTCTTT | TATAGCTTCA | GAGAGAGCAA | TTGCATTGCA | GGGCGCGCTC | AATAACATTG | 180 |
| GACCCGATGG | CTCAGCAGTA | CCAGGGGCTG | GAGCGGGCTT | CGTAGTCGCA | AGTCCTTCAA | 240 |
| AGGCCAATCC | CGATTACTTC | TACACATGGA | GTCGGACTC | AGCCTTGACA | TTGAAAATGA | 300 |
| TCATTGATGA | GTTTATCCTT | GGAAACACCA | CCCTCCAGAC | GATAATCGAA | CAATATATCC | 360 |
| ATGCCCAAGC | AGTTCTTCAG | ACCGTTTCCA | ATCCATCTGG | AACCTTCCTG | CCTGACGGTG | 420 |
| TCGGATTAGG | AGAGCCAAAG | TTCATGGTCG | ATGGAACTCG | GTTCAATGGG | CCTTGGGGAC | 480 |
| GGCCTCAACG | TGACGGCCCA | GCTCTCCGCG | CTATTGCCTT | AATGACCTAT | AGTAATTGGC | 540 |
| TCATTAAGAA | TGGTCAATTT | GCGGAGGCCA | AGACAAAGAT | ATGGCCCATT | ATTGCCAACG | 600 |
| ATCTCTCATA | CGTGGGACAA | TATTGGAACC | AGAGTGGTTT | TGACCTTTGG | GAAGAAACTT | 660 |
| ACGCATCCAG | CTTCTTCACC | ATCCAGAACC | AGCACCGAGC | TCTTGTCGAG | GGTGCGCAGC | 720 |
| TCGCCCATGA | TCTCGGTGTC | ACATGTACAG | GCTGTGACCA | GGCACCGGAG | GTTCTCTGCT | 780 |
| TCCTCCAAAG | TTTCTGGAAC | GGTAAATACA | TCGTGTCGAA | CATCAACGTC | AATAACGGCC | 840 |
| GAACTGGCTT | GGATGGAAAC | TCCATACTAG | GGCCATCTC | AACTTTTGAT | ATCGATGCGT | 900 |
| ACTGCGATAG | TCCAACCTTG | CAACCTTGCC | ATAGCCAGTC | TTTGGCAAAT | TTCAAGGTCT | 960 |
| TGACAGACAC | TTTTAGGAAC | TTGTATACCA | TCAACGCTGG | CATTCCGGAA | GGCCAAGGGG | 1020 |
| TAGCTGTCGG | GAGATACGCC | GAGGACGTTT | ACATGGGCGG | TAATCCATGG | TATCTGATCA | 1080 |
| CCACCGCAGC | AGCAGAGTTC | TTGTATGATG | CAGTAGCACA | GTGGAAGGCT | CGTCATGTGC | 1140 |
| TCACCGTTGA | CGAGACGTCT | CTCGCATTCT | TCAAAGATAT | CTACCCCGAA | GTCACCGTCC | 1200 |
| GCGAGTACAA | AAGCGGGAAC | GCCAACAGCC | CATTCGCACA | GATCATGGAT | GCTGTGACCG | 1260 |
| CCTACGCCGA | CTCGTACGTC | GCCATCGCCG | AGAAATACAT | CCCCTCCAAC | GGATCCCTCT | 1320 |
| CGGAGCAATT | CAACCGCGAT | ACAGGAACCC | CCTATCCGC | CATCGACCTC | ACCTGGTCCT | 1380 |
| ACGCCGCCTT | CATAACCATG | TCTCAACGCC | GCGCCGGCCA | ATACCCCAGC | AGCTGGGGCT | 1440 |
| CCCGCAACGC | CTTGCCGCCT | CCTACCACCT | GCTCCGCCAG | CTCCACCCCG | GGCATCTACA | 1500 |
| CCCCCGCCAC | CGCCGCCGGC | GCCCCAACG | TAACATCCAG | CTGCCAGGTC | AGCATCACCT | 1560 |
| TCAACATCAA | CGCCACCACC | TACTACGGCG | AGAACCTCTA | CGTGATCGGT | AACTCGTCAG | 1620 |
| ATCTGGGCGC | CTGGAATATC | GCCGATGCGT | ACCCGCTCAG | CGCCAGTGCA | TATACGCAGG | 1680 |
| ACCGCCCGCT | CTGGAGTGCC | GCTATCCCGT | TGAATGCGGG | TGAGGTTATT | AGCTATCAGT | 1740 |
| ATGTGCGCCA | GGAAGACTGT | GATCAGCCGT | ATATATACGA | GACGGTTAAT | CGCACCCTGA | 1800 |
| CGGTACCCGC | GTGTGGAGGC | GCGGCTGTCA | CTACGGATGA | TGCGTGGATG | GGACCGGTGG | 1860 |

```
GCTCATCTGG GAATTGCTGA AGGGGGTTTG GGGTTTGGGA TTGAAGATAG ATAGATGGAG      1920

ATTTAGATCT GGTTAATTAC TGGGTTTATA AACTTACGTG CATTCAGTAA TTCATGGGTT      1980

TTGCAAAAAA AAAAAA                                                      1996
```

( 2 ) INFORMATION FOR SEQ ID NO:2:

( i ) SEQUENCE CHARACTERISTICS:
        ( A ) LENGTH: 616 amino acids
        ( B ) TYPE: amino acid
        ( D ) TOPOLOGY: both ( x i ) SEQUENCE DESCRIPTION: SEQ ID NO:2:

```
Met Arg Leu Leu Pro Ser Ser Cys Ala Gly Ala Leu Ser Leu Leu Cys
 1               5                  10                  15

Ser Leu Ala Ile Ala Ala Pro Thr Glu Leu Lys Ala Arg Asp Leu Ser
            20                  25                  30

Ser Phe Ile Ala Ser Glu Arg Ala Ile Ala Leu Gln Gly Ala Leu Asn
        35                  40                  45

Asn Ile Gly Pro Asp Gly Ser Ala Val Pro Gly Ala Gly Ala Gly Phe
    50                  55                  60

Val Val Ala Ser Pro Ser Lys Ala Asn Pro Asp Tyr Phe Tyr Thr Trp
65                  70                  75                  80

Ser Arg Asp Ser Ala Leu Thr Leu Lys Met Ile Ile Asp Glu Phe Ile
                85                  90                  95

Leu Gly Asn Thr Thr Leu Gln Thr Ile Ile Glu Gln Tyr Ile His Ala
            100                 105                 110

Gln Ala Val Leu Gln Thr Val Ser Asn Pro Ser Gly Thr Phe Leu Pro
        115                 120                 125

Asp Gly Val Gly Leu Gly Glu Pro Lys Phe Met Val Asp Gly Thr Arg
    130                 135                 140

Phe Asn Gly Pro Trp Gly Arg Pro Gln Arg Asp Gly Pro Ala Leu Arg
145                 150                 155                 160

Ala Ile Ala Leu Met Thr Tyr Ser Asn Trp Leu Ile Lys Asn Gly Gln
                165                 170                 175

Phe Ala Glu Ala Lys Thr Lys Ile Trp Pro Ile Ile Ala Asn Asp Leu
            180                 185                 190

Ser Tyr Val Gly Gln Tyr Trp Asn Gln Ser Gly Phe Asp Leu Trp Glu
        195                 200                 205

Glu Thr Tyr Ala Ser Ser Phe Phe Thr Ile Gln Asn Gln His Arg Ala
    210                 215                 220

Leu Val Glu Gly Ala Gln Leu Ala His Asp Leu Gly Val Thr Cys Thr
225                 230                 235                 240

Gly Cys Asp Gln Ala Pro Glu Val Leu Cys Phe Leu Gln Ser Phe Trp
                245                 250                 255

Asn Gly Lys Tyr Ile Val Ser Asn Ile Asn Val Asn Asn Gly Arg Thr
            260                 265                 270

Gly Leu Asp Gly Asn Ser Ile Leu Gly Ala Ile Ser Thr Phe Asp Ile
        275                 280                 285

Asp Ala Tyr Cys Asp Ser Pro Thr Leu Gln Pro Cys His Ser Gln Ser
    290                 295                 300

Leu Ala Asn Phe Lys Val Leu Thr Asp Thr Phe Arg Asn Leu Tyr Thr
305                 310                 315                 320

Ile Asn Ala Gly Ile Pro Glu Gly Gln Gly Val Ala Val Gly Arg Tyr
                325                 330                 335

Ala Glu Asp Val Tyr Met Gly Gly Asn Pro Trp Tyr Leu Ile Thr Thr
```

|     |     |     |     |     |     |     | 340 |     |     |     |     | 345 |     |     |     |     | 350 |     |     |
|-----|-----|-----|-----|-----|-----|-----|-----|-----|-----|-----|-----|-----|-----|-----|-----|-----|-----|-----|-----|

Ala Ala Ala Glu Phe Leu Tyr Asp Ala Val Ala Gln Trp Lys Ala Arg
    355                                      360                            365

His Val Leu Thr Val Asp Glu Thr Ser Leu Ala Phe Phe Lys Asp Ile
   370                                  375                              380

Tyr Pro Glu Val Thr Val Arg Glu Tyr Lys Ser Gly Asn Ala Asn Ser
385                                    390                          395                400

Pro Phe Ala Gln Ile Met Asp Ala Val Thr Ala Tyr Ala Asp Ser Tyr
                   405                        410                        415

Val Ala Ile Ala Glu Lys Tyr Ile Pro Ser Asn Gly Ser Leu Ser Glu
           420                          425                          430

Gln Phe Asn Arg Asp Thr Gly Thr Pro Leu Ser Ala Ile Asp Leu Thr
        435                       440                          445

Trp Ser Tyr Ala Ala Phe Ile Thr Met Ser Gln Arg Arg Ala Gly Gln
   450                                455                          460

Tyr Pro Ser Ser Trp Gly Ser Arg Asn Ala Leu Pro Pro Pro Thr Thr
465                                  470                        475                480

Cys Ser Ala Ser Ser Thr Pro Gly Ile Tyr Thr Pro Ala Thr Ala Ala
                   485                        490                        495

Gly Ala Pro Asn Val Thr Ser Ser Cys Gln Val Ser Ile Thr Phe Asn
           500                          505                          510

Ile Asn Ala Thr Thr Tyr Tyr Gly Glu Asn Leu Tyr Val Ile Gly Asn
        515                       520                        525

Ser Ser Asp Leu Gly Ala Trp Asn Ile Ala Asp Ala Tyr Pro Leu Ser
   530                            535                         540

Ala Ser Ala Tyr Thr Gln Asp Arg Pro Leu Trp Ser Ala Ala Ile Pro
545                                  550                        555                560

Leu Asn Ala Gly Glu Val Ile Ser Tyr Gln Tyr Val Arg Gln Glu Asp
                   565                        570                        575

Cys Asp Gln Pro Tyr Ile Tyr Glu Thr Val Asn Arg Thr Leu Thr Val
           580                          585                        590

Pro Ala Cys Gly Gly Ala Ala Val Thr Thr Asp Asp Ala Trp Met Gly
        595                       600                          605

Pro Val Gly Ser Ser Gly Asn Cys
   610                           615

( 2 ) INFORMATION FOR SEQ ID NO:3:

( i ) SEQUENCE CHARACTERISTICS:
     ( A ) LENGTH: 2745 base pairs
     ( B ) TYPE: nucleic acid
     ( C ) STRANDEDNESS: both
     ( D ) TOPOLOGY: both ( i x ) FEATURE:
     ( A ) NAME/KEY: CDS
     ( B ) LOCATION: join(295..520, 594..898, 1075..1583, 1637..2447)

( x i ) SEQUENCE DESCRIPTION: SEQ ID NO:3:

```
CCTCCGCTTC  TTCCCCTCTT  CCCCACTTCC  CCAGGGGAAT  GACCTTCGTG  CTACGGCGCG        60

CAACCAGTCA  TCTCACGATG  TTGCCGCAAT  TGAATCGGTC  CGTTCAGGTT  TATCCGTCAA       120

CAAGCTTTAA  GCTTTTCAGG  CTTCGGGGTC  GAGTGGAGTA  ATCGAGCCAT  CGTGGGAGAG       180

ACAAGCTCAC  TAGGAGGCGG  CGGGGAAGTT  GGATATTGTG  AACATATAAG  AGCATGCTCG       240

TTCTAGCTAC  AATGACTTCA  TTCGTTTTAT  TGTTACTTCC  AGACTCATCT  CATC ATG       297
                                                                    Met
                                                                      1
```

```
CGC CTC CTC CCC TCG TCG TGT GCA GGG GCT CTC TCT TTG CTC TGC TCC        345
Arg Leu Leu Pro Ser Ser Cys Ala Gly Ala Leu Ser Leu Leu Cys Ser
             5                  10                  15

CTG GCG ATC GCA GCA CCT ACG GAA TTG AAA GCC AGA GAT TTG AGC TCT        393
Leu Ala Ile Ala Ala Pro Thr Glu Leu Lys Ala Arg Asp Leu Ser Ser
            20                  25                  30

TTT ATA GCT TCA GAG AGA GCA ATT GCA TTG CAG GGC GCG CTC AAT AAC        441
Phe Ile Ala Ser Glu Arg Ala Ile Ala Leu Gln Gly Ala Leu Asn Asn
        35                  40                  45

ATT GGA CCC GAT GGC TCA GCA GTA CCA GGG GCT GGA GCG GGC TTC GTA        489
Ile Gly Pro Asp Gly Ser Ala Val Pro Gly Ala Gly Ala Gly Phe Val
    50                  55                  60                  65

GTC GCA AGT CCT TCA AAG GCC AAT CCC GAT    T GTCAGTACCC ATCTACAAAC    540
Val Ala Ser Pro Ser Lys Ala Asn Pro Asp
                70                  75

ATCTTCCTTA CCACGAGTCA GGAATCCCAG TTGCGTGTAC TGACTATCAT TAG  AC         595
                                                             Tyr

TTC TAC ACA TGG AGT CGG GAC TCA GCC TTG ACA TTG AAA ATG ATC ATT        643
Phe Tyr Thr Trp Ser Arg Asp Ser Ala Leu Thr Leu Lys Met Ile Ile
            80                  85                  90

GAT GAG TTT ATC CTT GGA AAC ACC ACC CTC CAG ACG ATA ATC GAA CAA        691
Asp Glu Phe Ile Leu Gly Asn Thr Thr Leu Gln Thr Ile Ile Glu Gln
        95                  100                 105

TAT ATC CAT GCC CAA GCA GTT CTT CAG ACC GTT TCC AAT CCA TCT GGA        739
Tyr Ile His Ala Gln Ala Val Leu Gln Thr Val Ser Asn Pro Ser Gly
    110                 115                 120

ACC TTC CTG CCT GAC GGT GTC GGA TTA GGA GAG CCA AAG TTC ATG GTC        787
Thr Phe Leu Pro Asp Gly Val Gly Leu Gly Glu Pro Lys Phe Met Val
125                 130                 135                 140

GAT GGA ACT CGG TTC AAT GGG CCT TGG GGA CGG CCT CAA CGT GAC GGC        835
Asp Gly Thr Arg Phe Asn Gly Pro Trp Gly Arg Pro Gln Arg Asp Gly
                145                 150                 155

CCA GCT CTC CGC GCT ATT GCC TTA ATG ACC TAT AGT AAT TGG CTC ATT        883
Pro Ala Leu Arg Ala Ile Ala Leu Met Thr Tyr Ser Asn Trp Leu Ile
            160                 165                 170

AAG AAT GGT CAA TTT GTAAGGATCT CCTGTGAACA GTGTCGTCTG GTATAGATGG        938
Lys Asn Gly Gln Phe
            175

ATCCATGAGC TATCACTCCT GCCTCAGACA GTCTCTCAAG GTTAAACCTG TGCTTTAACT      998

CATGAATCTC CTTGCCCCTA GGATATTGAG AGTCTTTTGG TCCAATCAAG CAATTGCTAA     1058

TTCCCTTGTT GTCTAG GCG GAG GCC AAG ACA AAG ATA TGG CCC ATT ATT        1107
                Ala Glu Ala Lys Thr Lys Ile Trp Pro Ile Ile
                                180                 185

GCC AAC GAT CTC TCA TAC GTG GGA CAA TAT TGG AAC CAG AGT GGT TTT       1155
Ala Asn Asp Leu Ser Tyr Val Gly Gln Tyr Trp Asn Gln Ser Gly Phe
        190                 195                 200

GAC CTT TGG GAA GAA ACT TAC GCA TCC AGC TTC TTC ACC ATC CAG AAC       1203
Asp Leu Trp Glu Glu Thr Tyr Ala Ser Ser Phe Phe Thr Ile Gln Asn
205                 210                 215                 220

CAG CAC CGA GCT CTT GTC GAG GGT GCG CAG CTC GCC CAT GAT CTC GGT       1251
Gln His Arg Ala Leu Val Glu Gly Ala Gln Leu Ala His Asp Leu Gly
                225                 230                 235

GTC ACA TGT ACA GGC TGT GAC CAG GCA CCG GAG GTT CTC TGC TTC CTC       1299
Val Thr Cys Thr Gly Cys Asp Gln Ala Pro Glu Val Leu Cys Phe Leu
            240                 245                 250

CAA AGT TTC TGG AAC GGT AAA TAC ATC GTG TCG AAC ATC AAC GTC AAT       1347
Gln Ser Phe Trp Asn Gly Lys Tyr Ile Val Ser Asn Ile Asn Val Asn
        255                 260                 265

AAC GGC CGA ACT GGC TTG GAT GGA AAC TCC ATA CTA GGG GCC ATC TCA       1395
```

|     |     |     |     |     |     |     |     |     |     |     |     |     |     |     |      |
|-----|-----|-----|-----|-----|-----|-----|-----|-----|-----|-----|-----|-----|-----|-----|------|
| Asn | Gly | Arg | Thr | Gly | Leu | Asp | Gly | Asn | Ser | Ile | Leu | Gly | Ala | Ile | Ser  |
|     | 270 |     |     |     | 275 |     |     |     |     | 280 |     |     |     |     |      |
| ACT | TTT | GAT | ATC | GAT | GCG | TAC | TGC | GAT | AGT | CCA | ACC | TTG | CAA | CCT | TGC  | 1443
| Thr | Phe | Asp | Ile | Asp | Ala | Tyr | Cys | Asp | Ser | Pro | Thr | Leu | Gln | Pro | Cys  |
| 285 |     |     |     |     | 290 |     |     |     |     | 295 |     |     |     |     | 300  |
| CAT | AGC | CAG | TCT | TTG | GCA | AAT | TTC | AAG | GTC | TTG | ACA | GAC | ACT | TTT | AGG  | 1491
| His | Ser | Gln | Ser | Leu | Ala | Asn | Phe | Lys | Val | Leu | Thr | Asp | Thr | Phe | Arg  |
|     |     |     |     | 305 |     |     |     |     | 310 |     |     |     |     | 315 |      |
| AAC | TTG | TAT | ACC | ATC | AAC | GCT | GGC | ATT | CCG | GAA | GGC | CAA | GGG | GTA | GCT  | 1539
| Asn | Leu | Tyr | Thr | Ile | Asn | Ala | Gly | Ile | Pro | Glu | Gly | Gln | Gly | Val | Ala  |
|     |     |     | 320 |     |     |     |     | 325 |     |     |     |     | 330 |     |      |
| GTC | GGG | AGA | TAC | GCC | GAG | GAC | GTT | TAC | ATG | GGC | GGT | AAT | CCA |     | TG   | 1583
| Val | Gly | Arg | Tyr | Ala | Glu | Asp | Val | Tyr | Met | Gly | Gly | Asn | Pro |     | Trp  |
|     |     | 335 |     |     |     |     | 340 |     |     |     |     | 345 |     |     |      |

GTTGGTTTCC GTGGTTTTGC CCTCATCAAT CCGTACAGTA ACTGACTTGA TAG G TAT        1640
                                                              Tyr

|     |     |     |     |     |     |     |     |     |     |     |     |     |     |     |      |
|-----|-----|-----|-----|-----|-----|-----|-----|-----|-----|-----|-----|-----|-----|-----|------|
| CTG | ATC | ACC | ACC | GCA | GCA | GCA | GAG | TTC | TTG | TAT | GAT | GCA | GTA | GCA | CAG  | 1688
| Leu | Ile | Thr | Thr | Ala | Ala | Ala | Glu | Phe | Leu | Tyr | Asp | Ala | Val | Ala | Gln  |
|     | 350 |     |     |     |     | 355 |     |     |     |     | 360 |     |     |     |      |
| TGG | AAG | GCT | CGT | CAT | GTG | CTC | ACC | GTT | GAC | GAG | ACG | TCT | CTC | GCA | TTC  | 1736
| Trp | Lys | Ala | Arg | His | Val | Leu | Thr | Val | Asp | Glu | Thr | Ser | Leu | Ala | Phe  |
| 365 |     |     |     |     | 370 |     |     |     |     | 375 |     |     |     |     | 380  |
| TTC | AAA | GAT | ATC | TAC | CCC | GAA | GTC | ACC | GTC | CGC | GAG | TAC | AAA | AGC | GGG  | 1784
| Phe | Lys | Asp | Ile | Tyr | Pro | Glu | Val | Thr | Val | Arg | Glu | Tyr | Lys | Ser | Gly  |
|     |     |     |     | 385 |     |     |     |     | 390 |     |     |     |     | 395 |      |
| AAC | GCC | AAC | AGC | CCA | TTC | GCA | CAG | ATC | ATG | GAT | GCT | GTG | ACC | GCC | TAC  | 1832
| Asn | Ala | Asn | Ser | Pro | Phe | Ala | Gln | Ile | Met | Asp | Ala | Val | Thr | Ala | Tyr  |
|     |     |     | 400 |     |     |     |     | 405 |     |     |     |     | 410 |     |      |
| GCC | GAC | TCG | TAC | GTC | GCC | ATC | GCC | GAG | AAA | TAC | ATC | CCC | TCC | AAC | GGA  | 1880
| Ala | Asp | Ser | Tyr | Val | Ala | Ile | Ala | Glu | Lys | Tyr | Ile | Pro | Ser | Asn | Gly  |
|     |     | 415 |     |     |     |     | 420 |     |     |     |     | 425 |     |     |      |
| TCC | CTC | TCG | GAG | CAA | TTC | AAC | CGC | GAT | ACA | GGA | ACC | CCC | CTA | TCC | GCC  | 1928
| Ser | Leu | Ser | Glu | Gln | Phe | Asn | Arg | Asp | Thr | Gly | Thr | Pro | Leu | Ser | Ala  |
|     | 430 |     |     |     |     | 435 |     |     |     |     | 440 |     |     |     |      |
| ATC | GAC | CTC | ACC | TGG | TCC | TAC | GCC | GCC | TTC | ATA | ACC | ATG | TCT | CAA | CGC  | 1976
| Ile | Asp | Leu | Thr | Trp | Ser | Tyr | Ala | Ala | Phe | Ile | Thr | Met | Ser | Gln | Arg  |
| 445 |     |     |     |     | 450 |     |     |     |     | 455 |     |     |     |     | 460  |
| CGC | GCC | GGC | CAA | TAC | CCC | AGC | AGC | TGG | GGC | TCC | CGC | AAC | GCC | TTG | CCG  | 2024
| Arg | Ala | Gly | Gln | Tyr | Pro | Ser | Ser | Trp | Gly | Ser | Arg | Asn | Ala | Leu | Pro  |
|     |     |     |     | 465 |     |     |     |     | 470 |     |     |     |     | 475 |      |
| CCT | CCT | ACC | ACC | TGC | TCC | GCC | AGC | TCC | ACC | CCG | GGC | ATC | TAC | ACC | CCC  | 2072
| Pro | Pro | Thr | Thr | Cys | Ser | Ala | Ser | Ser | Thr | Pro | Gly | Ile | Tyr | Thr | Pro  |
|     |     |     | 480 |     |     |     |     | 485 |     |     |     |     | 490 |     |      |
| GCC | ACC | GCC | GCC | GGC | GCC | CCC | AAC | GTA | ACA | TCC | AGC | TGC | CAG | GTC | AGC  | 2120
| Ala | Thr | Ala | Ala | Gly | Ala | Pro | Asn | Val | Thr | Ser | Ser | Cys | Gln | Val | Ser  |
|     |     | 495 |     |     |     |     | 500 |     |     |     |     | 505 |     |     |      |
| ATC | ACC | TTC | AAC | ATC | AAC | GCC | ACC | ACC | TAC | TAC | GGC | GAG | AAC | CTC | TAC  | 2168
| Ile | Thr | Phe | Asn | Ile | Asn | Ala | Thr | Thr | Tyr | Tyr | Gly | Glu | Asn | Leu | Tyr  |
|     | 510 |     |     |     |     | 515 |     |     |     |     | 520 |     |     |     |      |
| GTG | ATC | GGT | AAC | TCG | TCA | GAT | CTG | GGC | GCC | TGG | AAT | ATC | GCC | GAT | GCG  | 2216
| Val | Ile | Gly | Asn | Ser | Ser | Asp | Leu | Gly | Ala | Trp | Asn | Ile | Ala | Asp | Ala  |
| 525 |     |     |     |     | 530 |     |     |     |     | 535 |     |     |     |     | 540  |
| TAC | CCG | CTC | AGC | GCC | AGT | GCA | TAT | ACG | CAG | GAC | CGC | CCG | CTC | TGG | AGT  | 2264
| Tyr | Pro | Leu | Ser | Ala | Ser | Ala | Tyr | Thr | Gln | Asp | Arg | Pro | Leu | Trp | Ser  |
|     |     |     |     | 545 |     |     |     |     | 550 |     |     |     |     | 555 |      |
| GCC | GCT | ATC | CCG | TTG | AAT | GCG | GGT | GAG | GTT | ATT | AGC | TAT | CAG | TAT | GTG  | 2312
| Ala | Ala | Ile | Pro | Leu | Asn | Ala | Gly | Glu | Val | Ile | Ser | Tyr | Gln | Tyr | Val  |
|     |     |     | 560 |     |     |     |     | 565 |     |     |     |     | 570 |     |      |
| CGC | CAG | GAA | GAC | TGT | GAT | CAG | CCG | TAT | ATA | TAC | GAG | ACG | GTT | AAT | CGC  | 2360
| Arg | Gln | Glu | Asp | Cys | Asp | Gln | Pro | Tyr | Ile | Tyr | Glu | Thr | Val | Asn | Arg  |

```
                575                         580                         585
ACC CTG ACG GTA CCC GCG TGT GGA GGC GCG GCT GTC ACT ACG GAT GAT              2408
Thr Leu Thr Val Pro Ala Cys Gly Gly Ala Ala Val Thr Thr Asp Asp
    590             595                     600

GCG TGG ATG GGA CCG GTG GGC TCA TCT GGG AAT TGC TGAAGGGGGT                   2454
Ala Trp Met Gly Pro Val Gly Ser Ser Gly Asn Cys
605                 610                 615

TTGGGGTTTG GGATTGAAGA TAGATAGATG GAGATTTAGA TCTGGTTAAT TACTGGGTTT            2514

ATAAACTTAC GTGCATTCAG TAATTCATGG GTTTTGCAAA TCTGATTCTC ATATAAAGAT            2574

ATGAATATGG TAGGACCTTC TCTCTTCGCA TTGCTGCTTC CTTTGCAGAA CAAAAGGGGG            2634

AAAGGCTGTT ACACATACGA GTCCGAGTCC CCGCGAATCA AGACTGGGGG ATTAGATATC            2694

TATAATGGGG ATTCTGCTTC TCCCGCCGAG TCATCAGAAG GGGGGAGTCC C                    2745
```

( 2 ) INFORMATION FOR SEQ ID NO:4:

( i ) SEQUENCE CHARACTERISTICS:
        ( A ) LENGTH: 616 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Arg Leu Leu Pro Ser Ser Cys Ala Gly Ala Leu Ser Leu Leu Cys
 1               5                  10                  15

Ser Leu Ala Ile Ala Ala Pro Thr Glu Leu Lys Ala Arg Asp Leu Ser
                20                  25                  30

Ser Phe Ile Ala Ser Glu Arg Ala Ile Ala Leu Gln Gly Ala Leu Asn
            35                  40                  45

Asn Ile Gly Pro Asp Gly Ser Ala Val Pro Gly Ala Gly Ala Gly Phe
        50                  55                  60

Val Ala Ser Pro Ser Lys Ala Asn Pro Asp Tyr Phe Tyr Thr Trp
 65                  70                  75                  80

Ser Arg Asp Ser Ala Leu Thr Leu Lys Met Ile Ile Asp Glu Phe Ile
                85                  90                  95

Leu Gly Asn Thr Thr Leu Gln Thr Ile Ile Glu Gln Tyr Ile His Ala
               100                 105                 110

Gln Ala Val Leu Gln Thr Val Ser Asn Pro Ser Gly Thr Phe Leu Pro
               115                 120                 125

Asp Gly Val Gly Leu Gly Glu Pro Lys Phe Met Val Asp Gly Thr Arg
       130                 135                 140

Phe Asn Gly Pro Trp Gly Arg Pro Gln Arg Asp Gly Pro Ala Leu Arg
145                 150                 155                 160

Ala Ile Ala Leu Met Thr Tyr Ser Asn Trp Leu Ile Lys Asn Gly Gln
               165                 170                 175

Phe Ala Glu Ala Lys Thr Lys Ile Trp Pro Ile Ile Ala Asn Asp Leu
               180                 185                 190

Ser Tyr Val Gly Gln Tyr Trp Asn Gln Ser Gly Phe Asp Leu Trp Glu
               195                 200                 205

Glu Thr Tyr Ala Ser Ser Phe Phe Thr Ile Gln Asn Gln His Arg Ala
       210                 215                 220

Leu Val Glu Gly Ala Gln Leu Ala His Asp Leu Gly Val Thr Cys Thr
225                 230                 235                 240

Gly Cys Asp Gln Ala Pro Glu Val Leu Cys Phe Leu Gln Ser Phe Trp
               245                 250                 255
```

```
Asn Gly Lys Tyr Ile Val Ser Asn Ile Val Asn Asn Gly Arg Thr
        260                 265                 270

Gly Leu Asp Gly Asn Ser Ile Leu Gly Ala Ile Ser Thr Phe Asp Ile
        275                 280                 285

Asp Ala Tyr Cys Asp Ser Pro Thr Leu Gln Pro Cys His Ser Gln Ser
    290                 295                 300

Leu Ala Asn Phe Lys Val Leu Thr Asp Thr Phe Arg Asn Leu Tyr Thr
305                 310                 315                 320

Ile Asn Ala Gly Ile Pro Glu Gly Gln Gly Val Ala Val Gly Arg Tyr
                325                 330                 335

Ala Glu Asp Val Tyr Met Gly Gly Asn Pro Trp Tyr Leu Ile Thr Thr
            340                 345                 350

Ala Ala Ala Glu Phe Leu Tyr Asp Ala Val Ala Gln Trp Lys Ala Arg
        355                 360                 365

His Val Leu Thr Val Asp Glu Thr Ser Leu Ala Phe Phe Lys Asp Ile
    370                 375                 380

Tyr Pro Glu Val Thr Val Arg Glu Tyr Lys Ser Gly Asn Ala Asn Ser
385                 390                 395                 400

Pro Phe Ala Gln Ile Met Asp Ala Val Thr Ala Tyr Ala Asp Ser Tyr
                405                 410                 415

Val Ala Ile Ala Glu Lys Tyr Ile Pro Ser Asn Gly Ser Leu Ser Glu
            420                 425                 430

Gln Phe Asn Arg Asp Thr Gly Thr Pro Leu Ser Ala Ile Asp Leu Thr
        435                 440                 445

Trp Ser Tyr Ala Ala Phe Ile Thr Met Ser Gln Arg Arg Ala Gly Gln
    450                 455                 460

Tyr Pro Ser Ser Trp Gly Ser Arg Asn Ala Leu Pro Pro Pro Thr Thr
465                 470                 475                 480

Cys Ser Ala Ser Ser Thr Pro Gly Ile Tyr Thr Pro Ala Thr Ala Ala
                485                 490                 495

Gly Ala Pro Asn Val Thr Ser Ser Cys Gln Val Ser Ile Thr Phe Asn
            500                 505                 510

Ile Asn Ala Thr Thr Tyr Tyr Gly Glu Asn Leu Tyr Val Ile Gly Asn
        515                 520                 525

Ser Ser Asp Leu Gly Ala Trp Asn Ile Ala Asp Ala Tyr Pro Leu Ser
    530                 535                 540

Ala Ser Ala Tyr Thr Gln Asp Arg Pro Leu Trp Ser Ala Ala Ile Pro
545                 550                 555                 560

Leu Asn Ala Gly Glu Val Ile Ser Tyr Gln Tyr Val Arg Gln Glu Asp
                565                 570                 575

Cys Asp Gln Pro Tyr Ile Tyr Glu Thr Val Asn Arg Thr Leu Thr Val
            580                 585                 590

Pro Ala Cys Gly Gly Ala Ala Val Thr Thr Asp Asp Ala Trp Met Gly
        595                 600                 605

Pro Val Gly Ser Ser Gly Asn Cys
610                 615
```

( 2 ) INFORMATION FOR SEQ ID NO:5:

( i ) SEQUENCE CHARACTERISTICS:
        ( A ) LENGTH: 74 base pairs
        ( B ) TYPE: nucleic acid
        ( C ) STRANDEDNESS: both
        ( D ) TOPOLOGY: both ( i x ) FEATURE:
        ( A ) NAME/KEY: CDS -continued ( B ) LOCATION: 14..73

( x i ) SEQUENCE DESCRIPTION: SEQ ID NO:5:

| | | | | | | | | | | | | | | | |
|---|---|---|---|---|---|---|---|---|---|---|---|---|---|---|---|
| GCGGACTGGC | ATC | ATG | TAT | CGG | AAG | TTG | GCC | GTC | ATC | TCG | GCC | TTC | TTG | | 49 |
| | | Met | Tyr | Arg | Lys | Leu | Ala | Val | Ile | Ser | Ala | Phe | Leu | | |
| | | 1 | | | 5 | | | | | 10 | | | | | |

| | | | | | | | |
|---|---|---|---|---|---|---|---|
| GCC | ACA | GCT | CGT | GCT | CAG | TTG | AGC T | 74 |
| Ala | Thr | Ala | Arg | Ala | Gln | Leu | Ser | |
| 15 | | | | | | 20 | | |

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Tyr | Arg | Lys | Leu | Ala | Val | Ile | Ser | Ala | Phe | Leu | Ala | Thr | Ala | Arg |
|---|---|---|---|---|---|---|---|---|---|---|---|---|---|---|---|
| 1 | | | | 5 | | | | | 10 | | | | | 15 | |

| Ala | Gln | Leu | Ser |
|---|---|---|---|
| | | | 20 |

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: both ( x i ) SEQUENCE DESCRIPTION: SEQ ID NO:7:

| Ala | Asn | Pro | Asp | Tyr | Phe |
|---|---|---|---|---|---|
| 1 | | | | 5 | |

RECOMBINANT PRODUCTION OF GLUCOAMYLASE P IN TRICHODERMA

CROSS-REFERENCE TO RELATED APPLICATIONS

This application is a continuation of application Ser. No. 08/104,853, filed Aug. 12, 1993, now abandoned, and is a Continuation-In-Part (CIP) of U.S. application Ser. No. 07/937,789, filed Sep. 3, 1992, now abandoned.

FIELD OF THE INVENTION

The invention is in the field of molecular biology, and specifically is directed to the recombinant expression of Hormoconis resinae glucoamylase. Compared to the glucoamylase-pullulanase mixes commonly used in industrial processes, the high debranching activity and the high limit dextrinase activity of this enzyme on starch makes it especially useful for industrial purposes. In addition, the host organism, *T. reesei*, secretes enzyme activities which are important for the degradation of complexes around and in starch granules of raw material.

BACKGROUND OF THE INVENTION

I. Host

A. *Trichoderma reesei*

The mesophilic filamentous fungus *Trichoderma reesei* is very efficient in secreting cellulase enzymes into the growth medium. In optimized cultivation conditions, amounts of up to 40 g/l of extracellular cellulase have been reported (Durand et al., *Enzyme Microb. Technol.* 10:341–346 (1988); Durand et al., in *Biochemistry and Genetics of Cellulose Degradation*, Academic Press, 1988, pp. 135–151).

Development of transformation systems for *T. reesei* (Knowles et al., EP244,234; Penttilä et al., *Gene* 61:155–164 (1987); Berka et al., EP215,594) has made possible the application of genetic engineering methods to the fungus. By genetic engineering, production profiles of different cellulase enzymes have been modulated e.g., to give strains with improved levels of the endoglucanase I enzyme. The strong cbh1 promoter has been applied to promote endoglucanase expression (Nevalainen, H., et al., "The molecular biology of Trichoderma and its application to the expression of both homologous and heterologous genes," in *Molecular Industrial Mycology*, Leong and Berka, eds., Marcel Dekker Inc., New York, pp. 129–148 (1992); and Harkki, A. et al., *Enzyme Microb. Technol.* 13:227–233 (1991)).

In addition to tailoring the production profiles of homologous proteins, the production potential of *T. reesei* has been harnessed to express various heterologous proteins in the fungus. So far examples are few and include e.g., calf chymosin (Knowles et al., EP244,234; Berka et al., EP215, 594; Harkki, A., et al., *Bio/Technol.* 7:596–603 (1989); Uusitalo, J. M., et al., *J. Biotechnol.* 17:35–50 (1991), CBH 1-Fab fusion antibodies raised against 2-phenyl-oxazolone (Nyyssönen et al., WO92/01797) and a fungal ligninolytic enzyme (Saloheimo, M. and Niku-Paavola, M. -L., *Bio/Technol.* 9:987–990 (1991)). For improved expression, the desired gene has been inserted into a cbh1 expression cassette and introduced into *T. reesei* by protoplast transformation (Harkki, A., et al., *Bio/Technol.* 7:596–603 (1989); Nyyssönen et al., WO92/01797; Saloheimo, M. and Niku-Paavola, M. -L, *Bio/Technol.* 9:987–990 (1991)). Even though heterologous filamentous fungal promoters such as Aspergillus amdS, argB and glucomylase (GA) can function in *T. reesei* at least to some extent (Penttilä et al., *Gene* 61:155–164 (1987); Knowles et al., EP244,234) efficient expression requires the use of a homologous promoter. In addition, better yields have been obtained in some cases by producing the desired gene product as a fusion protein (Harkki, A., et al, *Bio/Technol.* 7:596–603 (1989); Nyyssönen et al., WO92/01791). The yields of heterologous proteins obtained from *T. reesei* have varied between 10–150 mg/l.

II. Glucoamylases

Glucoamylase enzymes (α-1,4,-glucan glucohydrolase, EC 3.2.1.3) are starch hydrolyzing exoacting carbohydrases. They are microbial enzymes and are produced extracellularly by many molds and some yeasts. Starch is a heterogeneous polysaccharide containing 15–30% amylose and 70–85% amylopectin. Amylose is a linear polymer of 500 or more α-D(1–4)-linked glucose residues. Amylopectin is a branched polymer composed of about 20–30 α-D(1–4)-linked glucose units, which are connected to each other through α-D(1–6) linkages. These branch points comprise 4–5% of the total glucosidic bonds in starch.

Glucoamylases hydrolyze both α-1,4 and α-1,6 linkages in polysaccharides such as starch, liberating glucose units from nonreducing ends of the polysaccharides. These two activities are distinct. By hydrolyzing α-1,4 and α1,6 glucosidic bonds, glucomylases liberate β-D-glucose units from terminal nonreducing ends of a glucose polymer such as starch.

III. Debranching activities

Pullulanases are endo-acting hydrolytic enzymes specific for cleaving α-(1,6)-glucosidic bonds. However, the utility of pullulanases in many, industrial processes is limited by their inability to efficiently hydrolyze polymers smaller than maltosyl maltose. In contrast, some glucoamylases such as *Hormoconis resinae* glucoamylase P can hydrolyze a broad range of polymeric substrates including isomaltose (two glucose units connected by an α-(1,6)-glucosidic bond) and panose.

Glucoamylases differ considerably in their ability to hydrolyze α-(1,6)-glucosidic bonds. The highest debranching activities are found in the enzymes of fungi such as *Hormoconis resinae* (prior name *Cladosporium resinae*). Research on this fungus has revealed that it actually produces two distinct glucoamylases which exhibit different molecular masses and pI values. The smaller glucoamylase P, has a very high debranching activity whereas the larger glucoamylase S, has virtually no debranching activity as measured using pullulan (Fagerström et al., *J. Gen. Microbiol.* 136:913–920 (1990); McCleary & Anderson, *Carbohydrate Research* 86:77–96 (1980)).

IV. Isolation and Recombinant Expression of Glucoamylase

Several genes coding for various glucoamylases have been cloned and expressed either in yeast or fungal expression systems.

A procedure for purifying glucoamylase P as well as portions of its amino acid sequence have been published (Fagerström et al., *J. Gen. Microbiol.* 136:913–920 (1990)). In addition, a restriction map of two overlapping glucoamylase cDNA fragments has been published as well as evidence which suggests that recombinant laboratory yeast may be used to express this gene (Torkkeli et al., *XIII International Specialized Symposium on Yeasts*, Leuven, Belgium (1989)).

The glucoamylase genes from both *Aspergillus niger* (WO 86/07091; WO 88/09795; U.S. Pat. No. 5,024,941) and from *Aspergillus awamori* (U.S. Pat. No. 4,794,175 and EP Patent No. 126206) have been cloned and expressed in yeast cells.

The glucoamylase gene from a fungus of the genus Rhizopus has been expressed in *Saccharomyces cerevisiae* (EP Application Publication No. 186066). In addition, other types of amylolytic yeast have been constructed by the introduction of a modified Rhizopus glucoamylase gene (Ashikari et al., *App. Microbiol. and Biotech.* 32:129–133 (1989)).

A recombinant Saccharomyces has been constructed by transforming *S. cerevisiae* with a glucoamylase gene from *C. albicans* resulting in the secretion of the α-(1,4)-glucosidic bond-cleaving enzyme (EP Patent Application Publication No. 0362179).

The glucoamylase gene from *Schwanniomyces castellii* has been cloned and expressed in *Saccharomyces cerevisiae* as well as in other forms of yeast (EP Patent Application Publications No. 0260404 and No. 0257115).

Brewing yeasts have been transformed with a recombinant plasmid having a gene coding for a glucoamylase of *Saccharomyces diastaticus* (Park et al., MBAA *Technical Quarterly* 27:112–116 (1990)).

An amylolytic *S. cerevisiae* strain which is able to use starch as its sole source of carbon has been developed and used to express the α-amylase and glucoamylase genes of *Schwanniomyces occidentalis* (Hollenberg and Strasser, *Food Biotechnology* 4:527–534 (1990)).

Dohmen et al., *Gene* 95:111–121 (1990), have expressed a *Schwanniomyces occidentalis* glucoamylase in *S. cerevisiae* cells by transforming the cells with centromere plasmids carrying the glucoamylase gene fused to different *S. cerevisiae* promoters.

The amino acid sequences of several different microbial glucoamylases have been determined. The complete sequences of *Aspergillus niger* (Svensson et al., *Carlsberg Res. Comm.* 48:529–544 (1983)) and *Aspergillus awamori* (Nunberg et al., *Mol. and Cell. Biol.* 4:2306–2315 (1984)) glucoamylases are identical. The glucoamylase enzymes from *Rhizopus oryzae* (Ashikari et al., *Agricultural and Biological Chem.* 50:957–964 (1986)), *Saccharomyces diastaticus* (Yamashita et al., *J. Bacteriol.* 161:567–573 (1985)), *Saccharomyces cerevisiae* (Yamashita et al., *J. Bacteriol.* 169:2142–2149 (1987)); *Aspergillus shirousami* (Shibuya et al., *Agric. Bio. Chem.* 54:1905–1914 (1990)); *Schwanniomyces occidentalis* (Dohmen et al., *Gene* 95:111–121 (1987)); Clostridium sp. G0005 (Ohnishi et al., *Eur. J. Biochem.* 207:413–418 (1992)); and *Saccharomycopsis fibuligera* (Itoh et al., *J. Bacteriol.* 169:4171–4176 (1987)) have also been sequenced.

V. Industrial Uses of Glucoamylases

The most widely used organism for commercial alcohol fermentation, *Saccharomyces cerevisiae*, cannot directly use starch as a growth substrate because *S. cerevisiae* lacks the enzymes necessary to hydrolyze the starch polymer to fermentable monomeric units. As a result, starch must undergo a pre-fermentation hydrolysis process before it can be used for large-scale ethanol production.

Typically, in the ethanol process, the starch polymer is ground, gelatinized by heating and then liquified by α-amylase, an endo-acting enzyme which hydrolyzes α-(1, 4)-glucosidic bonds. As a result, α-limit dextrins containing α-(1,6)-glucosidic bonds are formed. Currently, cleavage of these α-(1,6)-glucosidic bond linkages constitutes the main rate limiting step in the complete hydrolysis process and industrial use of substrates containing these bonds.

Efforts have been made to enhance the efficiency of this process through improved enzymatic protocols for the treatment of starch. For example, the glucoamylase most commonly used in ethanol production comes from Aspergillus. However, the debranching activity of this enzyme is often not sufficient for production purposes and preparations must be supplemented with other enzymes such as pullulanases. Pullulanases are ineffective in degrading small α-limit dextrins.

U.S. Pat. No. 4,211,842 and U.S. Pat. No. 4,234,686 present a method for obtaining a mixture of starch degrading enzymes from *Cladosporium resinae* (former name for *Hormoconis resinae*), and a procedure for isolating a glucoamylase with high debranching activity from the mixture. U.S. Pat. No. 4,318,927 suggests producing a low caloric alcoholic beverage using a mixture of starch-degrading enzymes recovered from the culture medium of *Cladosporium resinae* (ATCC No. 20495). Others have described beer production, especially low-calorie (light) beer wherein the unfermentable carbohydrate dextrin is broken down into fermentable sugars by glucoamylase enzymes of different origin (U.S. Pat. No. 4,684,525, *World Food & Drink Report* (WFD), Jan. 5, 1987), *Chemical Marketing Reporter*, Apr. 7, 1986, p.121). U.S. Pat. No. 4,863,864 and EP 185,327 describe alcohol production from starch using glucoamylase. U.S. Pat. No. 4,898,738 describes sake production using Aspergillus glucoamylase.

In addition to manufacturing processes directed to the production of alcohols or alcoholic beverages, glucoamylases are useful in a wide variety of applications requiring the hydrolysis of raw starch, or the presence of a debranching activity. For example, such applications include starch analysis (Rickard, J. E. et al., *J. Sc. Food and Agricul.* 41:373–379 (1987); the manufacture of glucose syrups (Illanes, A., *Alimentos* 8:22–29 (1983)), high-DE glucose syrups and high-maltose syrups (EP 405,283, Shen, G. J. et al., *Appl. Microbiol. Biotech.* 33:340–344 (1990)), the production of isomaltose (U.S. Pat. No. 4,898,820); the hydrolysis of maltose and maltodextrins (Celebi, S. S. et al., *J. Appl. Biochem. Biotechnol.* 27:164–171 (1991)); the preparation of high purity dextrose (EP452,238, JP 3,139, 289); high maltotetraose and high maltose content starch hydrolysates (U.S. Pat. No. 4,971,906, U.S. Pat. No. 4,925, 795); straight linear dextrin for use in food, medicines and cosmetics (JP 2049594); rice preparations that lack stickiness (JP 2031652); the preparation of food fibers by the enzymatic treatment of seed husks or brans, such as, for example, corn hull hydrolysis or maize husks, rice husks, soy bean husks, skins of peanuts, and brans of rice, wheat, barley, oat, adlay, rye, (JP 2101016), and especially the elimination of serum cholesterol elevation factor from wheat bran (JP 63185931); highly stable emulsions useful in the preparation of chocolate (EP 135,768B); the assay of starch contents of various biological materials, the assay of α-amylase (U.S. Pat. No. 4,902,621); the production of polysaccharides with improved rheological properties over raw starch (AU 8826548); the production of crystalline 2-O-alpha-D-glycopyranosyl-L-ascorbic acid (EP 425,066); lubricants and gels (EP 372,184); the synthesis of branched cyclodextrin (U.S. Pat. No. 4,931,389, Yoshida, Y. et al., *Hakko Kogaku Kaishi* 68:197–203 (1990)); an additive to laundry and dish washing detergents (U.S. Pat. No. 5,020, 377, EP 418,835, EP 450,627, EP 425,397); use in enzyme electrodes and multi-enzyme electrodes (Hamid, J. A. et al., *Analyst* 115:1289–1295 (1990)); use of fragments containing the starchbinding domain for the preparation of genetically engineered peptide affinity tails for the recovery of fusion proteins (Ford, C. et al., *J. Cell. Biochem.* (Suppl.) 14D:30 (1990), Chen, L. et al., *Abst. Annu. Meet. Am. Soc. Microbiol.* 90:269 (1990)); wood and textile industry applications such as, for example, the preparation of plywood adhesives and particle board binders (Mukherjee, S., Brazil Patent No. 400/88, issued Sep. 5, 1989) and saccharification of lignocellulosic materials; the preparation of high solids dextrin adhesives for the high speed coating of paper and wrinkle-free conversion of paper to envelopes, poster board, etc. (U.S. Pat. No. 4,921,795); the preservation of protein-containing animal or vegetable fodder (EP 346,909); the production of polysaccharides such as xanthine by aerobic fermentation of microorganisms wherein fermentation occurs in the presence of starch and an amylolytic enzyme such as glucoamylase (EP 319,372); improving the filterability of glucose syrups and/or lowering the viscosity of the same (U.S. Pat. No. 4,746,517); lowering the viscosity of organic slurries in fermentation processes (Wu, Y. V. et al., *J. Agric. Food Chem.* 37:1174–1177 (1989); the bioconversion of distillery wastes (Perdih, A. et al., *Enzyme Microb. Technol.* 13:848–852 (1991) or vegetable wastes (Von Richter, G. *Starch* 35:113–118 (1983)) or fruit waste (Horn, C. H. et al., *Biol. Wastes* 24:127–136 (1988) into feedstuff including feed additives, bulk fillers, sweetening agents, liquid feed components for farm animals, raw materials for ethanol production for consumption and as a fuel source); the preparation of feedstuff from meat by-products such as slaughterhouse, leather and good processing industry wastes (NL 8403620); treatment of feeds and fodder to increase contents of reducing sugars (SU 869745), improved utilization of sugar present in such feedstuff (Panciroli, G., *Suinicoltura* 24:19–24 (1983) including grass hays, mixed hays, legume hays, corn silage and rice straw (Abe, A. et al., *J. Anim. Sci.* 48:1483–1490 (1979)); and assays to predict the digestibility of animal feeds (Dowman, M. G. et al., *J. Sci. Food Agric* 33:689–696 (1982)). When used as a feed additive for food animals, the recombinant bacterial biomass may be added directly to the animal's fodder (SU 916,336).

Research has also been directed to the discovery, cloning and expression of enzymes with greater hydrolysis efficiency. A method of preparing glucoamylase S by culturing *Cladosporium resinae* (ATCC No. 20495) has been presented in U.S. Pat. No. 4,318,989.

Fagerström et al., *J. Gen. Microbiol.* 136:913–920 (1991) have presented evidence which suggests that of all the currently available glycoamylase enzymes, *H. resinae* glucoamylase P has the most favorable characteristics for industrial use because it is characterized by having an exceptionally high debranching activity. Thus, glucoamylase P may eliminate the need for the supplemental debranching enzymes in many industrial processes. However, *H. resinae* produces glucoamylase P in only minimal amounts (U.S. Pat. No. 4,318,927) and therefore, cannot be used efficiently in ethanol production. Therefore, a need still exists for an economical, large scale production of glucoamylase with a high debranching activity.

SUMMARY OF THE INVENTION

Recognizing the need for a recombinant host that can produce large quantities of *H. resinae* glucoamylase P, and cognizant of the ability of many filamentous fungi to secrete large quantities of proteins, the inventors investigated the use of filamentous fungi for the expression of *H. resinae* glucoamylase P cDNA and genomic DNA. Accordingly, the cDNA and gene for *H. resinae* glucoamylase P, a unique glucoamylase P that has a high debranching activity, has been isolated and sequenced. These efforts have culminated in the stable transformation of Trichoderma with DNA encoding *H. resinae* glucoamylase P, and the expression of this protein in large quantities from the recombinant host.

Therefore, the invention is directed to nucleic acid sequences encoding *H. resinae* glucoamylase P, including the native gene sequence and biologically functional fragments and derivatives thereof.

In another embodiment the invention is directed to the amino acid sequence of glucoamylase P, and to biologically functional fragments and derivatives thereof.

In another embodiment, the invention is directed to a stable transformed Trichoderma host, and methods for the expression of *Hormoconis resinae* glucoamylase P therefrom.

In another embodiment, the invention is directed to the culture medium, and enzyme preparations therefrom, obtained from the growth or culture of such transformed hosts, and the use of such preparations.

In another embodiment, the invention is directed to brewing methods using the enzyme preparations of the invention, and especially, the treatment of wort so as to improve the characteristics of wort, including increasing wort filterability, decreasing wort viscosity, and increasing the volume of wort extract.

In one further embodiment, the invention is, directed to mash treatment during the mashing, liquefaction and/or saccharification step, using the enzyme preparation of this invention, such treatment resulting in increased ethanol yields and improved saccharification of grain mash.

The Trichoderma-expressed recombinant glucoamylase P is an economical source of glucoamylase P for use in a wide variety of industrial applications involving the degradation of starch-like polymers.

Deposit of Microorganisms

An *E. coli* host carrying plasmid pALK305 (ALKO2311), encoding a cDNA gene for *H. resinae* glucoamylase P has been deposited at the Deutsche Sammlung von Microorganismen und Zellkulturen GMbH (DSM) (German Collection of Micro-organisms and Cell Cultures) on 17 Feb. 1992 and is assigned number DSM 6921.

BRIEF DESCRIPTION OF THE DRAWINGS

The figure of the constructions are not in scale unless otherwise noted.

FIG. 5 shows the nucleotide sequence (Seq ID No. 1), and FIG. 5A and 5B show the deduced amino acid sequence (Seq. ID No. 2), of the H. resinae glucoamylase P cDNA. The amino acids are numbered from the initiation site of translation. The N-terminal amino acid residue of the mature protein is Asp (amino acid number 30).

| SacII | | SacI |
|---|---|---|
| GGACTGGCATCATGTATCGGAAGTTGGCCGTCATCTCGGCCTTCTTGGCCACAGCTCGTGCTCAGTTGAGCT | | |
| CGCCTGACCGTAGTACATAGCCTTCAACCGGCAGTAGAGCCGGAAGAACCGGTGTCGAGCACGAGTCAAC | | |

The resulting plasmid, pALK308, was digested with PstI and XbaI. This generated a 4 kb fragment which was end-filled and then inserted into pALK100 which had been digested with PvuII and dephosphorylated. Prior to transformation, pALK310 was linearized with EcoRI.

Figure 7:
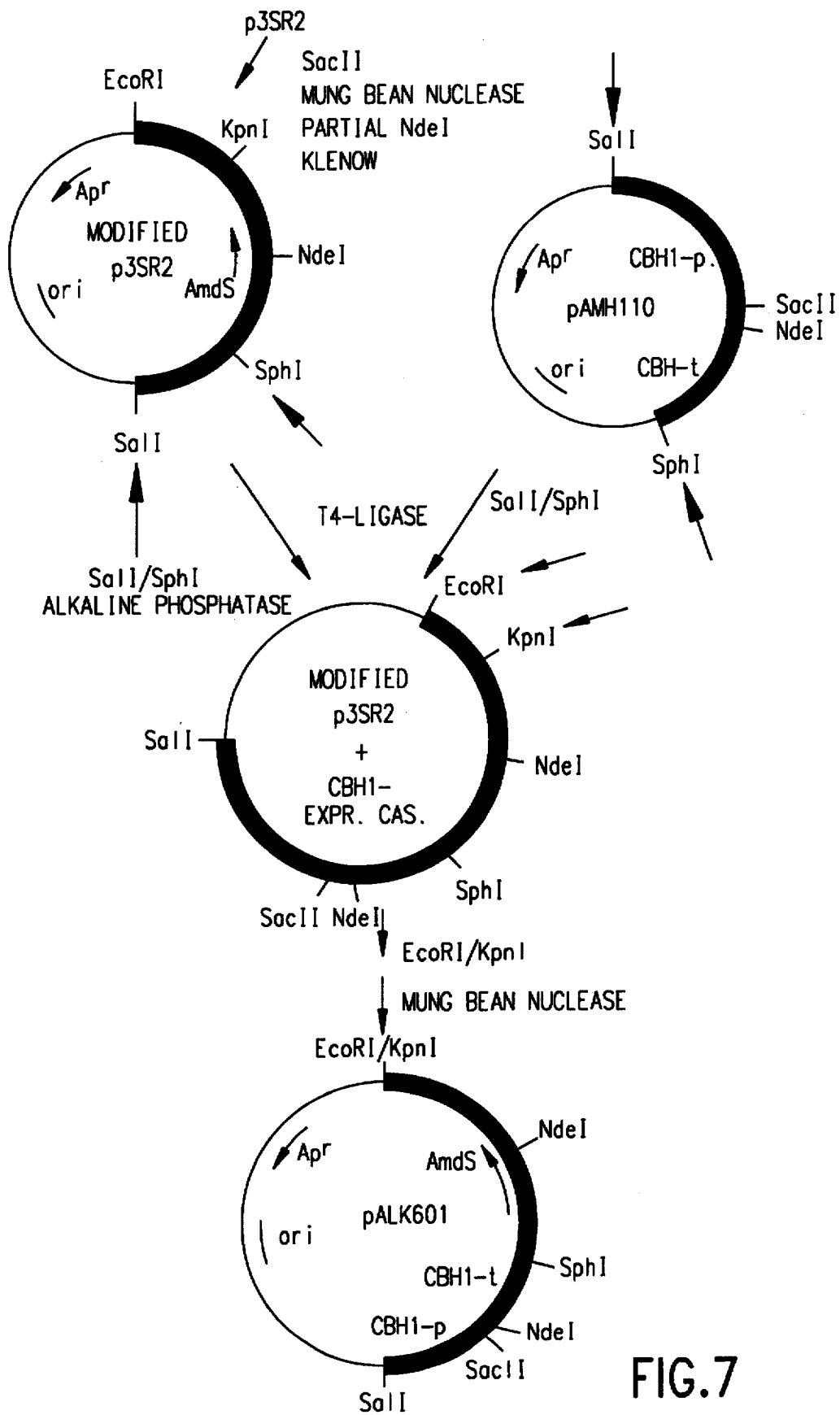

FIG. 7 shows the construction of the T. reesei expression vector pALK601.

Figure 8:
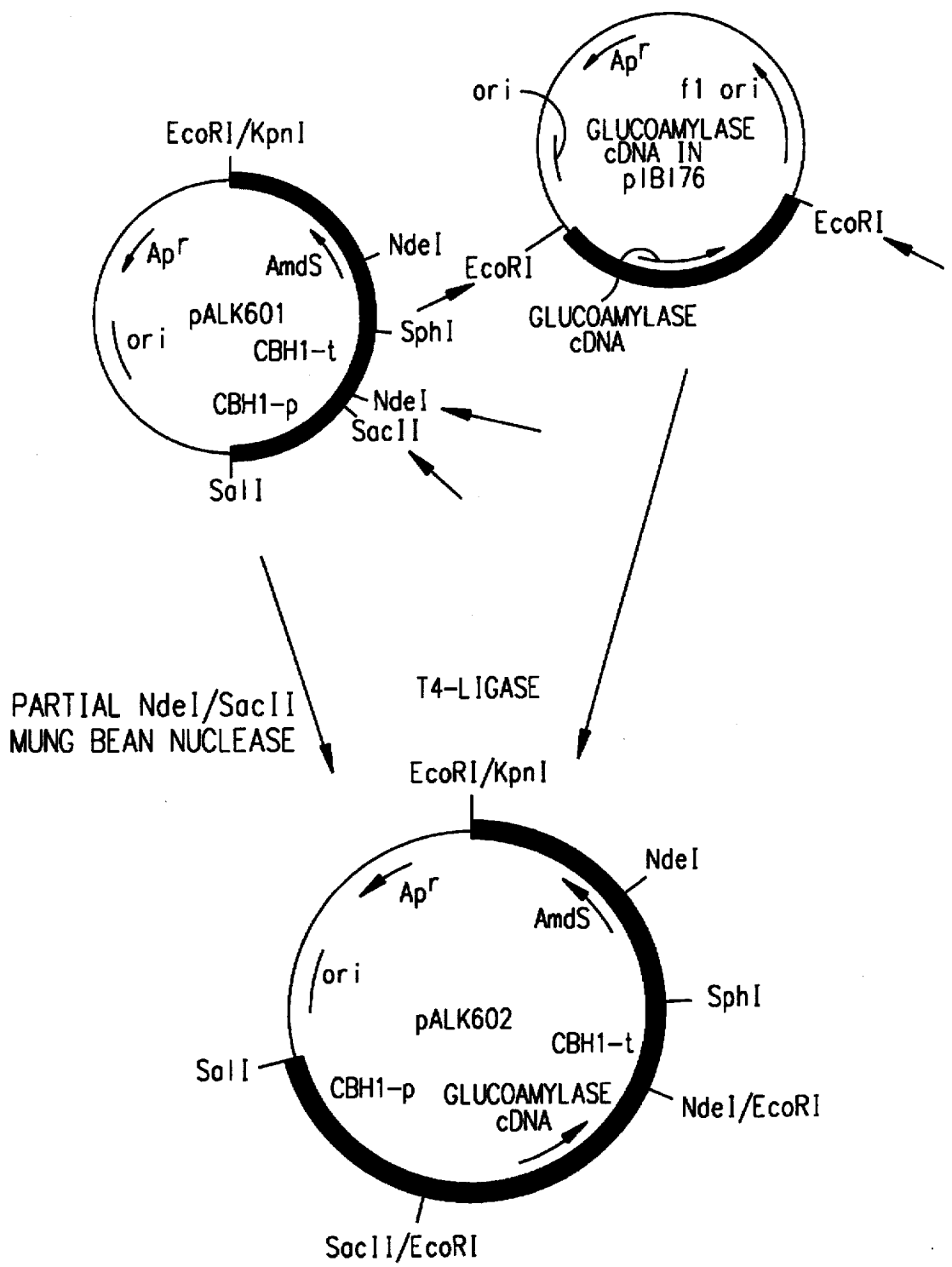

FIG. 8 shows the construction of pALK602, a vector for expressing H. resinae glucoamylase P in T. reesei.

Figure 9:
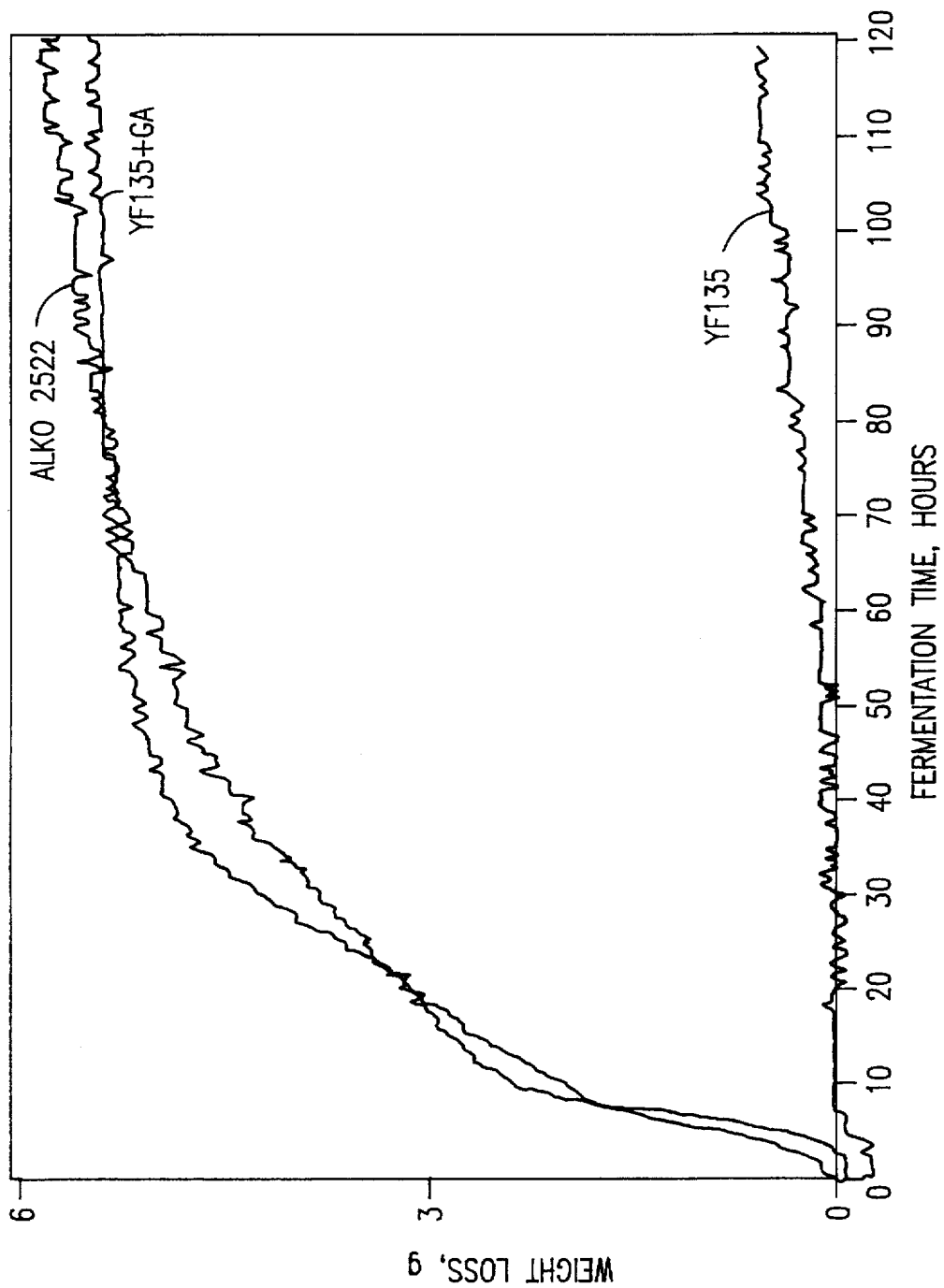

FIG. 9 shows the weight loss during ethanol fermentation of the yeast strains YF135, ALKO2522, and YF135 in the presence of added glucoamylase (YF135+GA).

Figure 10:
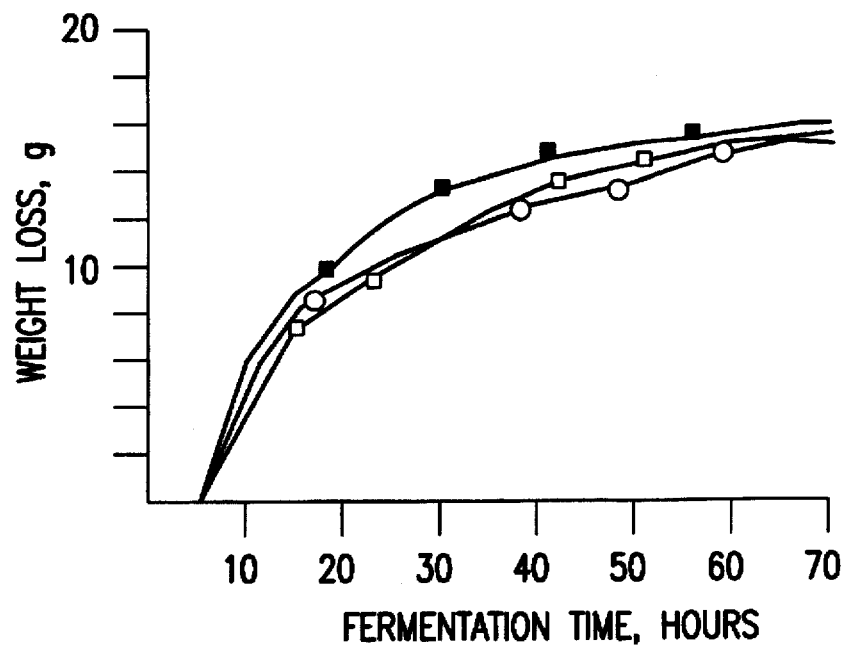

FIG. 10 shows the weight loss of saccharified grain mash during ethanol fermentation. Mash was saccharified for 30 min with 22.0 U of A. niger GAR (open circles), 22.0 U of Hormoconis resinae glucoamylase P (GAMP) from T. reesei (closed squares) or 16.5 U of GAMP from T. reesei (open squares).

Figure 11:
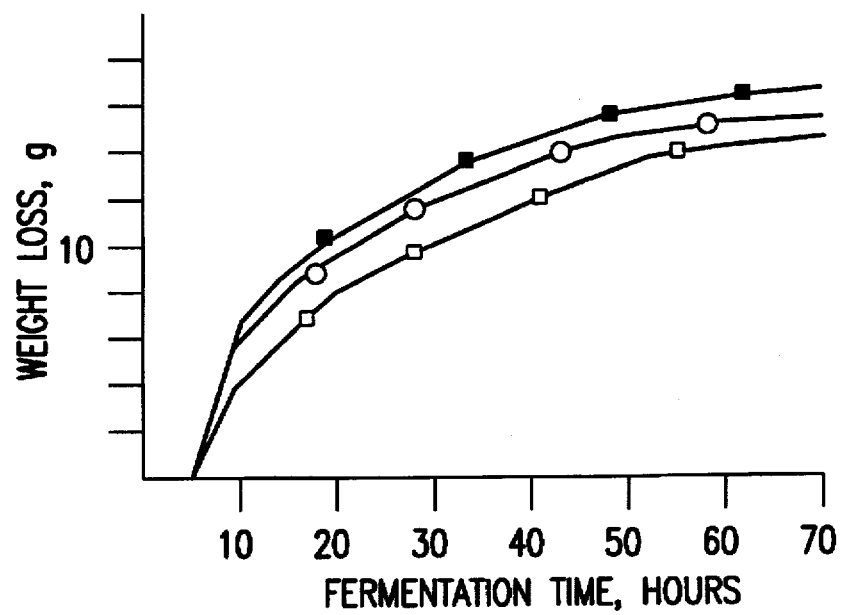

FIG. 11 shows the weight loss of saccharified grain mash during ethanol fermentation. Mash was saccharified for 120 min with 22.0 U of A. niger GAR (open circles), 22.0 U of GAMP from T. reesei (closed squares) or 16.5 U of GAMP from T. reesei (open squares).

Figure 12:
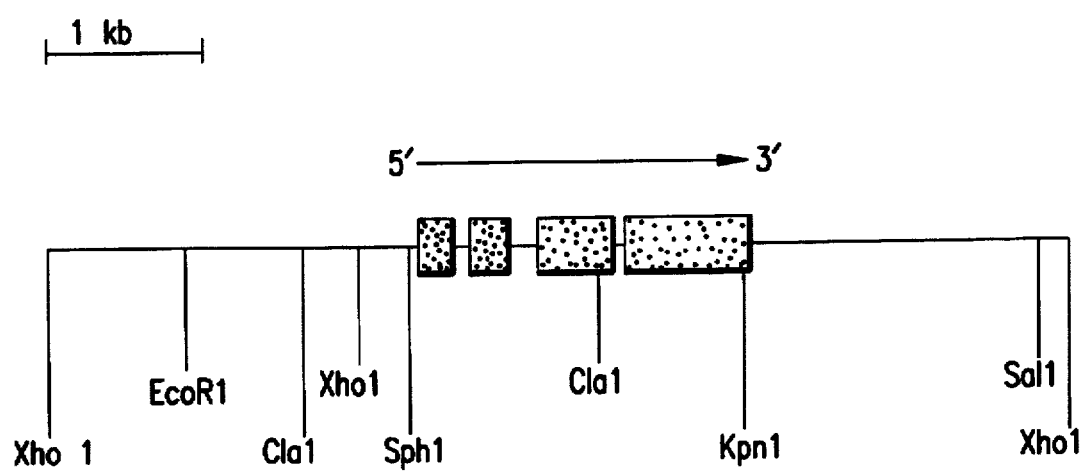

FIG. 12 shows the restriction endonuclease map of the cloned Hormoconis resinae genome area surrounding the glucoamylase P gene. Protein-encoding regions are indicated as solid boxes.

FIG. 13 (A,B,C) nucleotide sequence of the glucoamylase P gene (Seq ID No. 3) from Hormoconis resinae as determined from the insert of a genomic recombinant pBluescript plasmid. Intervening sequences (designated IVS) and both 5' and 3' non-translated regions are in lower case letters. The deduced protein sequence is presented (Seq. ID No. 4) and the first amino acid of the mature protein (Fagerström, R. et al., J. Gen. Microb. 136:913–920 (1990)) is marked with an asterisk. The TATA and CAAT sequences upstream of the translation initiation site and the ATAAA sequence downstream of the translation termination site are underlined. The CTGACT consensus sequence in the two short introns is also denoted with underlining. The sequence data presented here have been submitted to the EMBL database under accession No. X68143.

The 9.7 kb SalI-SphI segment, which contains the gamP and the amdS genes, was used to transform T. reesei ALKO2221. Abbreviations: S, SalI; Sal, SacI; SalI, SacII; Sp, SphI; p, promoter; t, terminator.

Figure 18:
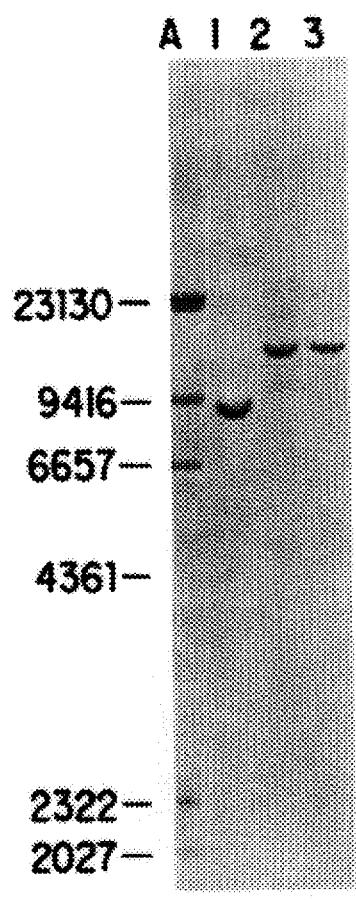
Figure 18A:

FIGS. 18 and 18a are Southern blot analyses of total DNA from the untransformed T. reesei host strain ALKO2221 and the transformant strains ALKO3435 and ALKO3435a probed with digoxigenin labeled probes. FIG. 18: 5 µg of XhoI-digested DNA from ALKO2221 (lane 1), ALKO3435 (lane 2) and ALKO3435a (lane 3) probed with the SalI-SphI cbh1 expression cassette from plasmid pAMH110 (Nevalainen, H. et al., in Molecular Industrial Mycology, Leong, S. A. and Berka, R., eds., pp. 129–148, Marcel Deccer, Inc., New York (1991)). FIG. 18A: 5 µg of SacII-digested DNA from ALKO2221 (lane 1), ALKO3435 (lane 2) and ALKO3435a (lane 3) probed with the SphI-SalI fragment, containing the genomic gamP gene, from plasmid pALK608 (Joutsjoki, V. V., et al., FEMS Microbiol. Lett. 99:237–144 (1992)). In each of FIGS. 18 and 18A, lanes A and B are HindIII- and EcoRI-HindIII-digested λ markers, respectively. The sizes of the fragments are indicated in base pairs.

Figure 19:
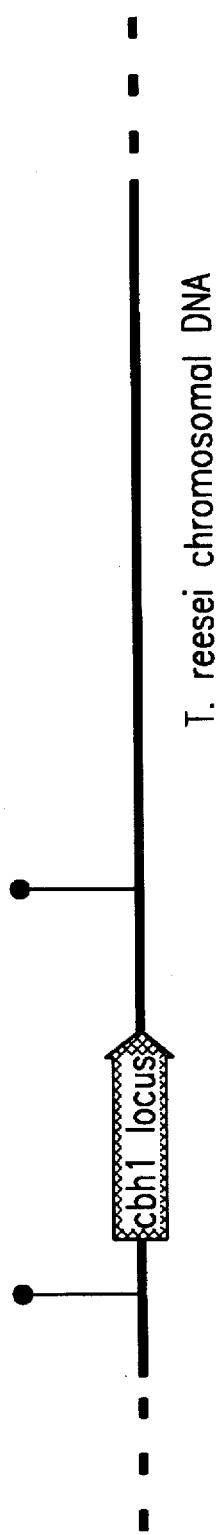
Figure 19A:
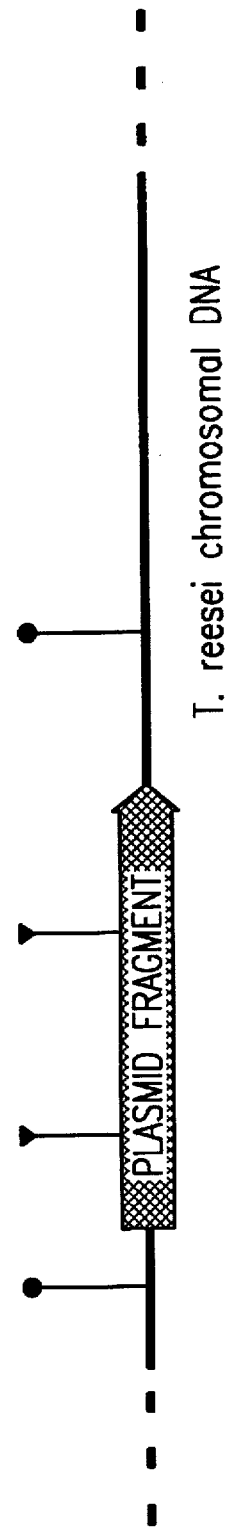

FIGS. 19 and 19A schematically present the cbh1 locus in the genome of the untransformed T. reesei host strain ALKO2221 and in the transformant strains ALKO3435 and ALKO3435a. The XhoI sites (●) flanking the resident cbh1 locus and the SacII sites (▼) in pALK612 and pALK613 plasmid fragments are shown.

Figure 20:
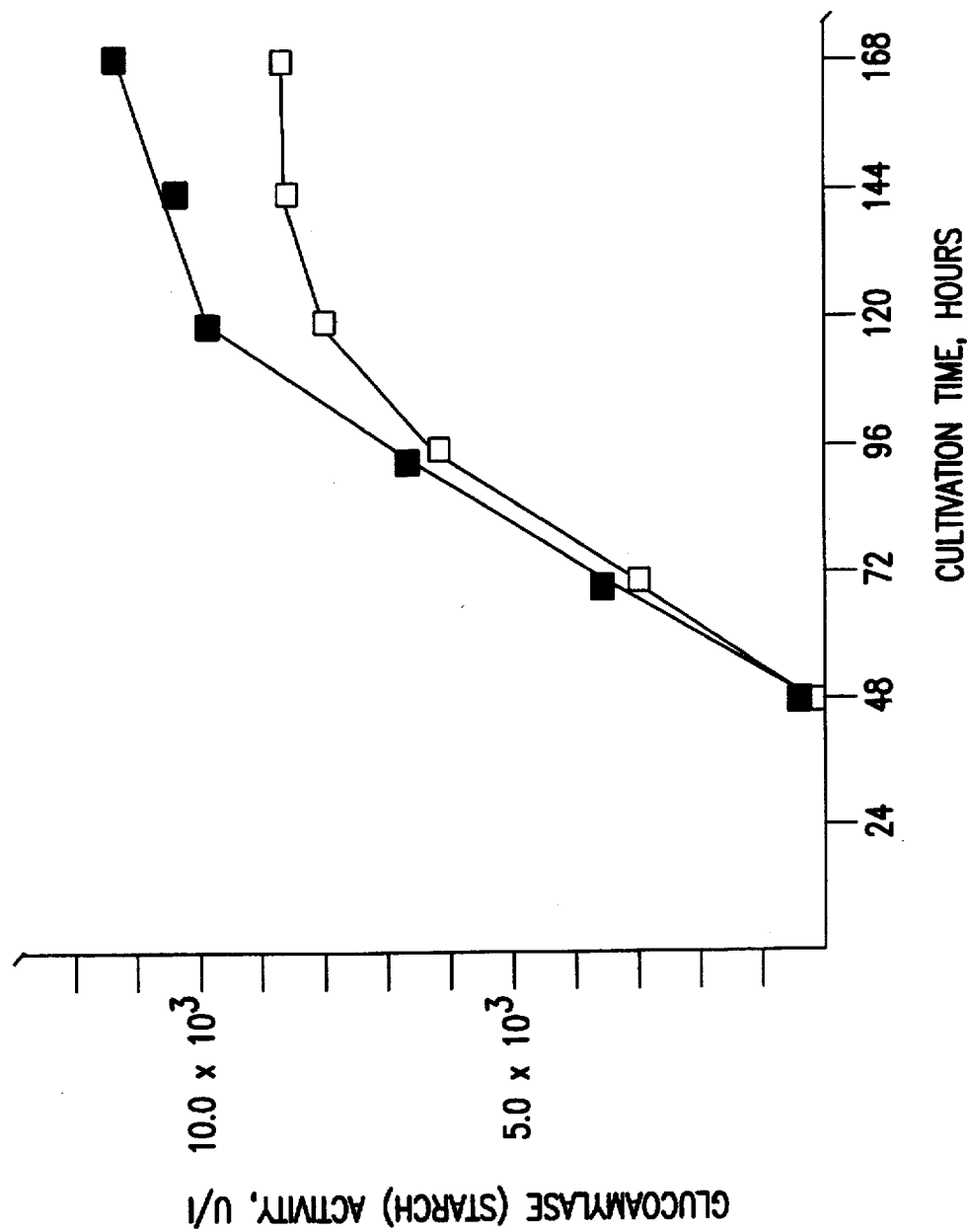

FIG. 20 shows the time course of the glucoamylase activity (the α-1,4 glucosidic activity) produced by the T. reesei transformant strains ALKO3435 (■) and ALKO3435a (□) in a 250 ml shake flask cultivation.

DETAILED DESCRIPTION OF THE PREFERRED EMBODIMENTS

Although there have been previous reports of purified glucoamylase P protein, the present inventors found that the glucoamylase P protein preparations described therein, and the methods used to isolate that protein, were not sufficiently economical to permit the large scale industrial utilization of this enzyme. Therefore, the production of recombinant glucoamylase P was investigated. These studies have culminated in the identification of a recombinant clones to glucoamylase P, both cDNA and genomic, and in the elucidation of the sequence of the glucoamylase P protein and gene. These studies have also culminated in the development of highly efficient *Trichoderma reesei* recombinant hosts, that can secrete useful amounts of recombinant glucoamylase P directly into the growth medium. The terms "growth medium" and "culture medium" are used interchangeably in this application.

Trichoderma was chosen as a recombinant host for the expression of glucoamylase P, because compared to Aspergillus, Trichoderma, such as *T. reesei*, secretes larger amounts of β-glucans and hemicellulose decomposing enzyme activities such as β-glucanase and xylanases. These activities are especially desirable in the enzyme preparations and methods of the invention.

*Trichoderma reesei* is the most efficient known producer of cellulases, and synthesizes all of the enzymes required for extensive hydrolysis of crystalline cellulose. In addition, the enzymes that are secreted from *T. reesei* and found in its growth medium have been reasonably well defined and appear to give the highest saccharification yields in hydrolysis of cellulose (Nevalainen, H. *Genetic Improvement of Enzyme Production in Industrially Important Fungal Strains*, Ph.D. Dissertation, Technical Research Centre of Finland Publications 26, VTT, Espoo, Finland, 1985; Mandels, M., *Biotechnol. Bioeng. Symp.* 5:81–105 (1975); Pettersson, G. et al., in: *The Ekman-Days*, International Symposium on Wood and Pulping Chemistry, SPCI, Stockholm, 1981, P.III, pp.39–42).

Cloning of Glucoamylase P Genetic Sequences

The process for production of glucoamylase P, according to the invention, is facilitated through the cloning of genetic sequences that are capable of encoding glucoamylase P protein and through the expression of such genetic sequences. As used herein, the term "genetic sequences" is intended to refer to a nucleic acid molecule (preferably DNA). Genetic sequences that are capable of encoding glucoamylase P are derived from a variety of sources. These sources include genomic DNA, cDNA, synthetic DNA, and combinations thereof. The preferred source of the glucoamylase P cDNA is a cDNA library from the filamentous fungus, *Hormoconis resinae*. The preferred source of the glucoamylase P genomic DNA is a genomic library from the filamentous fungus, *Hormoconis resinae*.

The glucoamylase P cDNA of the invention will not include naturally occurring introns if the cDNA was made using mature glucoamylase P mRNA as a template. The glucoamylase P genomic DNA of the invention may or may not include naturally occurring introns. Moreover, such genomic DNA may be obtained in association with the 5' promoter region of the glucoamylase P gene sequences and/or with the 3' transcriptional termination region. Further, such genomic DNA may be obtained in association with the genetic sequences which encode the 5' non-translated region of the glucoamylase P mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, may be retained and employed for transcriptional and translational regulation.

Glucoamylase P genomic DNA can be extracted and purified from any cell, preferably a filamentous fungal cell, which naturally expresses glucoamylase P by means well known in the art (for example, see *Guide to Molecular Cloning Techniques*, S. L. Berger et al., eds., Academic Press (1987). If a cDNA clone is desired, preferably, the mRNA preparation used will be enriched in mRNA coding for glucoamylase P, either naturally, by isolation from a source which produces large amounts of the protein, or in vitro, by techniques commonly used to enrich mRNA preparations for specific sequences, such as sucrose gradient centrifugation. The host preferred as a source of glucoamylase P mRNA is the filamentous fungus, *Hormoconis resinae*.

For cloning into a vector, the desired DNA preparation (either genomic DNA or ds cDNA) may be randomly sheared or enzymatically cleaved, and ligated into an appropriate vector to form a recombinant gene (either genomic or cDNA) library.

A DNA sequence encoding glucoamylase P or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are well known in the art.

Libraries containing sequences coding for glucoamylase P may be screened and a sequence coding for glucoamylase P identified by any means which specifically selects for such sequence, such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, c) if the cloned genetic sequences are themselves capable of expressing mRNA, by immunoprecipitation of a translated glucoamylase P product produced by the host containing the clone, or d) by assay of glucoamylase P activity in the growth medium of the transformed hosts.

Oligonucleotide probes specific for glucoamylase P which can be used to identify clones to this protein can be designed from knowledge of the amino acid sequence of glucoamylase P. This amino acid sequence can be deduced from the intact protein or obtained by enzymatic or chemical degradation of intact protein or its fragments followed by peptide separation and sequencing with methods well known in the art. As shown herein, when the amino acid sequence is listed horizontally, unless otherwise stated, the amino terminus is intended to be on the left end and the carboxy terminus is intended to be at the right end.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The amino acid sequence may be analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., in: *Molecular Biology of the Gene*, 3rd Ed., W. A. Benjamin, Inc., Menlo Park, Calif. (1977)), one or more different oligonucleotides can be identified from the amino acid sequence, each of which would be capable of encoding glucoamylase P. The probability that a particular oligonucleotide will, in fact, constitute an actual glucoamylase P encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the glucoamylase P sequences is identified.

The suitable oligonucleotide, or set of oligonucleotides, which is capable of encoding a fragment of a glucoamylase P gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate a cloned glucoamylase P gene by techniques known in the art. Techniques of nucleic acid hybridization and clone identification are disclosed by Maniatis, T., et al., in: *Molecular Cloning, A Laboratory Manual*, Cold Spring Harbor Laboratories, Cold Spring Harbor, N.Y. (1982)), and by Hames, B. D., et al., in: *Nucleic Acid Hybridization, A Practical Approach*, IRL Press, Washington, D.C. (1985)). Those members of the above-described gene library which are found to be capable of such hybridization are then analyzed to determine the extent and nature of glucoamylase P encoding sequences which they contain.

To facilitate the detection of a desired glucoamylase P DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radio-active labels, such as $^{32}P$, $^3H$, $^{14}C$, $^{35}S$, or the like. Any radioactive label may be employed which provides for an adequate signal and has a sufficient half-life. If single stranded, the oligonucleotide may be radioactively labelled using kinase reactions. Alternatively, and equally useful, polynucleotides can be labelled for use as nucleic acid hybridization probes with a non-radioactive marker such as digoxigenin, biotin, an enzyme or a fluorescent group. See, for example, Leary, J. J. et al., *Proc. Natl. Acad. Sci. USA* 80:4045 (1983); Renz. M. et al., *Nucl. Acids Res.* 12:3435 (1984); and Renz, M., *EMBO J.* 6:817 (1983).

Thus, in summary, the actual identification of glucoamylase P protein sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a glucoamylase P gene.

In an alternative way of cloning a glucoamylase P gene, a library is prepared using an expression vector, by cloning DNA or, more preferably cDNA prepared from a cell capable of expressing glucoamylase P into an expression vector. The library is then screened for members which express glucoamylase P, for example, by screening the library with antibodies to the protein, or by assaying growth medium for glucoamylase P activity.

The above discussed methods are, therefore, capable of identifying genetic sequences which are capable of encoding glucoamylase P or its fragments. In order to further characterize such genetic sequences, and, in order to produce recombinant glucoamylase P, especially full-length or antigenic or enzymatically active fragments of this protein, it is desirable to express the proteins which these sequences encode. Such expression identifies those clones which express proteins possessing characteristics of glucoamylase P. Such characteristics may include the ability to specifically bind glucoamylase P antibody, the ability to elicit the production of antibodies which are capable of binding to glucoamylase P, the ability to provide glucoamylase P enzymatic activity to a cell, and the ability to provide a glucoamylase P-function to a recipient cell, among others.

For the preparation of mutant glucoamylase P activity, site-directed mutagenesis may be performed as known in the art. For example, site-directed mutagenesis may be performed to alter the thermal stability of the glucoamylase P of the invention as described by Itoh, T. et al., *Agric. Biol. Chem.* 53:3159–3167 (1989) for the glucoamylase from *Saccharomycopsis fibuligera*, wherein Ala 81 and Asp 89 were shown to be important for the thermal stability of the enzyme.

Expression of Glucoamylase P and its Functional Derivatives

To express glucoamylase P and/or its enzymatically active derivatives, transcriptional and translational signals recognizable by an appropriate host are necessary. The cloned glucoamylase P protein encoding sequences, obtained through the methods described above, and preferably in a double-stranded form, may be operably linked to sequences controlling transcriptional expression in an expression vector, and introduced into a host cell, either prokaryote or eukaryote, to produce recombinant glucoamylase P or a functional derivative thereof. Depending upon which strand of the glucoamylase P encoding sequence is operably linked to the sequences controlling transcriptional expression, it is also possible to express glucoamylase P antisense RNA or a functional derivative thereof.

Expression of the glucoamylase P in different hosts may result in different post-translational modifications which may alter the properties of the protein. Glucoamylase P or a functional derivative thereof may be expressed in eukaryotic cells, and especially fungal, mammalian, and insect cells. Preferably, the present invention encompasses the expression of the glucoamylase P or a functional derivative thereof, in transformed *Trichoderma reesei*.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a glucoamylase P encoding sequence and a promoter region sequence linked to the 5' end of the protein encoding sequence) are said to be operably linked if induction of promoter function results in the transcription of the glucoamylase P encoding sequence mRNA and if the nature of the linkage between the two DNA sequences does not (1) result in the introduction of a frame-shift mutation, (2) interfere with the ability of the expression regulatory sequences to direct the expression of the glucoamylase P, antisense RNA, or protein, or (3) interfere with the ability of the glucoamylase P template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene. Such transcriptional control sequences may also include enhancer sequences or upstream activator sequences, as desired.

Expression of the glucoamylase P in recombinant hosts requires the use of regulatory regions functional in such hosts. A wide variety of transcriptional and translational regulatory sequences can be employed, depending upon the nature of the host. The transcriptional and translational regulatory signals can also be derived from the genomic sequences of viruses which infect the host cells. Preferably, a desired regulatory signal is one associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous fungal genes which encode a mRNA product capable of translation are preferred, and especially, strong promoters such as the promoter for *T. reesei* cellobiohydrolase I (CBHI), cellobiohydrolase II (CBHII), endoglucanase I (EGI), and endoglucanase II (EGII) may be employed, especially in the *T. reesei* host. In laboratory yeast hosts, the yeast GAL4 gene promoter, or a glycolytic gene promoter may be used such as the glycerol-3-phosphate dehydrogenase promoter.

As is widely known, translation of eukaryotic mRNA is initiated at the codon which encodes the first methionine. For this reason, it is preferable to ensure that the linkage between a eukaryotic promoter and a DNA sequence which encodes the glucoamylase P, or a functional derivative thereof, does not contain any intervening codons which are capable of encoding a methionine. The presence of such codons results either in a formation of a fusion protein (if the AUG codon is in the same reading frame as glucoamylase P encoding DNA sequence) or a frame-shift mutation (if the AUG codon is not in the same reading frame as the glucoamylase P encoding sequence).

If desired, a fusion product of the glucoamylase P may be constructed. Full-length glucoamylase P encodes a 29 amino acid residue signal sequence which will allow secretion of the protein from fungal hosts, including *Hormoconis resinae*, *Saccharomyces cerevisiae* and *Trichoderma reesei*.

The sequence coding for mature glucoamylase P may be linked to a heterologous signal sequence which will allow secretion of the protein from, or the compartmentalization of the protein in, a particular host. Such signal sequences may be designed with or without specific protease sites such that the signal peptide sequence is amenable to subsequent removal. Examples of such signal sequences for *T. reesei* hosts are those from the cellulase genes, and especially the cellobiohydrolase I (CBHI), cellobiohydrolase II (CBHII), endoglucanase I (EGI), and endoglucanase II (EGII) signal sequences.

Transcriptional initiation regulatory signals can be selected which allow for repression or activation, so that expression of the operably linked genes can be modulated.

If desired, the non-transcribed and/or non-translated regions 3' to the sequence coding for glucoamylase P can be obtained by the above-described cloning methods. The 3'-non-transcribed region may be retained for its transcriptional termination regulatory sequence elements; the 3'-non-translated region may be retained for its translational termination regulatory sequence elements, or for those elements which direct polyadenylation in eukaryotic cells. Where the native expression control sequences do not function satisfactorily in the host cell, then sequences functional in the host cell may be substituted.

To transform a fungal cell with the DNA constructs of the invention many vector systems are available depending upon whether it is desired to insert the glucoamylase P DNA construct into the host cell chromosomal DNA, or to allow it to exist in an extrachromosomal form. The stable transformation of *Trichoderma reesei* and the expression of heterologous genes in such transformants are described in EP 244,234. Preferred plasmid systems are described in the same and in U.S. application Ser. No. 07/496,155, filed Mar. 19, 1990, or in U.S. application Ser. 07/524,308 filed on May 16, 1990, incorporated herein by reference.

If the glucoamylase P encoding sequence and an operably linked promoter is introduced into a recipient eukaryotic cell as a non-replicating DNA (or RNA) molecule, the expression of the glucoamylase P may occur through the transient expression of the introduced sequence. Such a non-replicating DNA (or RNA) molecule may be a linear molecule or, more preferably, a closed covalent circular molecule which is incapable of autonomous replication.

In a preferred embodiment, genetically stable transformants may be constructed with vector systems, or transformation systems, whereby glucoamylase P DNA is integrated into the host chromosome. Such integration may occur de novo within the cell or, in a most preferred embodiment, be assisted by transformation with a vector inserting it into the host chromosome by homologous recombination, for example, with retroviral vectors, transposons or other DNA elements which promote integration of DNA sequences in chromosomes. A vector is employed which is capable of integrating the desired gene sequences into a fungal host cell chromosome. For example, for integration into the chromosome of *T. reesei*, such vectors may provide a gene encoded by *T. reesei*, such as the cellobiohydrolase I gene, to promote homologous recombination at a specific site on the host chromosome.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper. The selectable marker gene can either be directly linked to the DNA gene sequences to be expressed, or introduced into the same cell by co-transfection. Markers useful for transformation of *Trichoderma reesei* are described in U.S. application Ser. No. 07/496,155, filed Mar. 19, 1990; and in Finkelstein, D. B., Chapter 6 in *Biotechnology of Filamentous Fungi*, D. B. Finkelstein et al., eds., Butterworth-Heinemann, Boston, 1992, pp. 113–156, both incorporated herein fully by reference.

Factors of importance in selecting a particular vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct (s) is introduced into an appropriate host cell by any of a variety of suitable means. After the introduction of the vector, recipient cells are grown in a selective medium (if necessary), which selects for the growth of vector-containing cells. Expression of the cloned gene sequence(s) results in the production of the glucoamylase P, or in the production of a fragment of this protein. This expression can take place in a continuous manner in the transformed cells, or in a controlled manner, wherein a certain stimulus is necessary to induce the host cells to produce the cloned glucoamylase P.

If desired, the expressed recombinant glucoamylase P protein can be isolated and purified in accordance with conventional conditions, such as extraction, precipitation, chromatography, affinity chromatography, electrophoresis, or the like.

Industrial Uses of Glucoamylase P

Distilled alcohol is made by a series of processes, starting with the raw materials being converted to sugars that can be utilized by yeast, followed by fermentation, and finally the separation of the ethanol from the solution usually by distillation, leaving a residue rich in proteins and minerals useful as animal feed. For example, an integrated process can be used in which barley is processed to ethanol, starch, carbon dioxide, and different kinds of feed fractions.

For alcohol manufacturing, only the smaller starch granules, called "B starch," with a diameter of about 5 microns are used. The larger granules of about 15 microns (A-starch) go mainly for the purpose of coating paper.

The main advantages of using integrated ethanol and starch production processes are realized in the process and product economics: the water from the starch manufacturing can be used in alcohol manufacturing, material flows are flexible, and emphasis can be placed on the production of those end products with the highest demand.

Thus, processes such as those of the invention, in which the efficiency of the enzymatic conversions of starch to sugars is increased, are highly desirable. The *T. reesei* glucoamylase P strains of the invention are especially useful in brewing, such as the production of beer, and in the manufacture of grain alcohol. The strains of the invention secrete a mixture of enzymes ($\alpha$-1,4-glucoamylase, $\alpha$-1,6-glucoamylase P, $\beta$-glucanase, hydroxyethylcellulose degrading activity (HEC), filter paper degrading activity (FPU), xylanase (hemicellulose degrading activity), acid protease (protein degrading activity at pH 4.7) and $\beta$-glucosidase (cellobiose degrading activity)) into their growth medium. After separation of the solids from the medium, the medium can be used without further purification of these enzymes to very efficiently break down the macromolecular substances in ground grain slurry to substrates utilizable by yeast. The growth medium can be concentrated or diluted as desired to adjust the activity of a desired enzyme(s) in the preparation, using techniques known in the art, for example, lyophilization or dialysis.

The enzyme preparations of the invention, due to the presence of the glucoamylase P of the invention, are very active on the 1,6-linkages and thus degrade isomaltose, panose and pullulan 5–30 times more efficiently than preparations containing Aspergillus or Rhizopus glucoamylase. Complete hydrolyzation of the starch increases production of the simple sugars which then increases overall alcohol yield.

A continuous mode of fermentation (a cascade fermentation) is more efficient and economical than a batch mode. Especially with high cell concentrations, produced by cell recycling or by immobilization, a continuous volumetric productivity of 5–20 times higher than the batch mode can be obtained.

The advantage of cascade fermentation is that the lag time for starting fermentation is eliminated and the inhibition of fermentation caused by ethanol itself can be minimized over the whole range of fermentation by localizing the most severe inhibition to the last vessel in the series. Cascade fermentations are not truly continuous, since the process is stopped about every 2–3 weeks and the tanks are emptied for cleaning.

The growth medium of Trichoderma cultures contains all of the enzymes secreted by the Trichoderma. The enzymes in this medium are reasonably well characterized (see, for example, U.S. appl. Ser. No. 07/524,308, filed May 16, 1990, and U.S. appl. Ser. No. 07/889,893, filed May 29, 1992, both incorporated herein by reference). As such, the medium may be used as a mixture or as a source of these enzymes.

The *Hormoconis resinae* glucoamylase containing growth medium that is produced by any Trichoderma stain which has been transformed with cDNA or genomic sequences encoding glucoamylase P is a useful preparation that contains a desired mixture of enzyme activities. Examples of such strains include *Trichoderma reesei* ALKO 2743 (ALKO-GA). Examples of uses include starch-based biological processing, and specifically ethanol production, including brewing. The activities of $\beta$-glucanase and cellulase that are expressed by *T. reesei* strains 233 and 2743 are about the same order of magnitude. However, strain 233 expresses about ⅓ the xylanase activity of strain 2743.

For grain processing in ethanol production, the mashing procedure usually has three steps:

1) heating (this step is also called gelatinization);
2) addition of $\alpha$-amylase enzyme (this step is also called liquefaction); and,
3) addition of amylolytic enzymes such as glucoamylase, pullulanase, and limit dextrinase (this step is also called saccharification).

The glucoamylase containing medium (or enzyme preparation) of the invention may be added at any one stage of mashing, or at any two stages, or at all stages of mashing. However, if the enzyme is added before or during heating (gelatinization), the enzyme will be inactivated by the heating and additional enzyme must be added after the heating step.

The addition of the growth medium of the invention, (that is, growth medium taken from the culture of Trichoderma that have been transformed with sequences encoding the glucoamylase P of the invention, such as ALKO-GA), increases the recovery and alters the characteristics of wort and beer, when the enzyme (or enzyme-containing culture medium or preparation) is added at the beginning of mashing or fermentation. The same results are seen in pilot and laboratory scale studies. Also there is a difference in these results between the ALKO-GA and the commercial glucoamylase concentrate NOVO AMG 300 L, which is produced by *Aspergillus niger*.

The enzyme activity assays from enzyme concentrates show that ALKO-GA contains starch decomposing side activities as β-glucanase, cellulases, xylanases and β-glucosidase in quantities greater than those currently available, such as NOVO AMG 300 L.

When ALKO-GA or NOVO AMG 300 L was added in laboratory scale mashing, the change in characteristics of the wort was dependent on the amount of ALKO-GA enzyme addition. Thus, this dose effect allows for maximum flexibility in altering the characteristics of the wort. The enzyme effects were basically the same both with ALKO-GA and NOVO AMG 300 L except that the concentration of β-glucans in the treated wort was very low if ALKO-GA was used, and was similar to the control group if NOVO AMG 300 L was used. The low β-glucan concentration in ALKO-GA treated worts is one reason for the lower viscosity and higher filtration rate of the wort, both advantages in the industrial setting. For this reason, the recovery (volume) of the wort is remarkably higher from the ALKO-GA treated mash than from the NOVO AMG 300 L treated mash. This is also an advantage of the invention.

The reasons for this better response with ALKO-GA (even as an amount of 0.1 g/100 g mash) are believed to be the following. First, the β-glucanase, xylanase and cellulase activities in ALKO-GA produced by Trichoderma are higher compared to the same activities in NOVO AMG 300 L produced by Aspergillus. Second, the temperature stability seems to be higher with ALKO-GA β-glucanase compared to the *Aspergillus niger* β-glucanase, which seems to be destroyed during mashing, but not if added to the fermentation mix. The extract yield of the wort is similar in all conditions, but the volume of the extract was much higher when ALKO-GA was added in mashing compared to other commercial preparations, such as the NOVO AMG 300 L, which had no effect even when compared to the control experiment.

The apparent limit attenuation was increased from 84.7% to 89% when the ALKO-GA dose was 3 g/100 g mash. The higher dose had no effect, although there is an increase of fermentable sugars (glucose, maltose, maltotriose etc.) which correlate with the increase in enzyme dose. The result is also the same, if NOVO-AMG 300 L was used during mashing. Based on this result, the ALKO-GA dose 3 g/100 g mash for Pilot scale (100 L) brewing experiment is preferred.

When ALKO-GA or NOVO AMG 300 L is added in laboratory scale fermentation, the changes in characteristics of the wort are dependent on the amount of ALKO-GA enzyme addition and thus are also dose dependent. The enzyme effects are basically the same both with ALKO-GA and NOVO AMG 300 L except that the amount of β-glucans is remarkably lower if ALKO-GA was added than if NOVO AMG 300 L is added, which in contrast to the results in mashing experiments lowered the β-glucan content under the control value. Small amounts of β-glucanase of NOVO AMG 300 L seem to be active in fermentation temperature during long fermentation periods. The viscosity of the wort is lower than in control experiment and lower with the ALKO-GA compared to NOVO AMG 300 L.

During progress of fermentation the apparent extract yield was smaller in enzyme treated worts, thus also being dose dependent on the amount of enzyme added. This means that yeast was able to more effectively use the energy source of the wort.

There are a wide variety of industrial uses for the cloned glucoamylase P enzyme of the invention in addition to those already described. The glucoamylase P of the invention may be used in solution or immobilized on a solid support, such as plastic, glass, flexible polymeric supports such as nylon, polyurethane polymers, both foaming (such as Hypol FHP 2002 for foams) and non-foaming (such as Hypol FHP 8190H for gels), celite, activated carbon, chitin, glutaraldehyde-crosslinked chitin, Celite R649, porous ceramics (for example, SM-10), porous, granular diatomaceous earth, cellulose (such as cotton linkers and Fagus sulfite pulp), fiber and paper such as alginate fibers and papers, and resins such chromatography resins as DEAE cellulose. Methods for the immobilization of enzymes, and specifically glucoamylase are known in the art (Smiley, K. L. et al., *Adv. App. Microbiol.* 15:13–38 (1972); Illanes, A., *Alimentos* 8:22–29 (1983); and Celebi, S. S. et al., *J. Appl. Biochem. Biotechnol.* 27:164–171 (1991)). Such immobilization allows the use of the enzyme of the invention in reactor columns, including recirculated batch reactors and fixed membrane reactors. Immobilization may be facilitated through the use of concanavalin-A and/or cross-linking as known in the art (Saleenuddin, M. et al., *Enzyme Microb. Technol* 13:290–293 (1991)).

The glucoamylase of the invention is useful to enhance the efficiency of the saccharification of starch, such as in the production of glucose from starch. Especially, the enzyme of the invention may reduce or eliminate the need for the addition of pullulanase (EC-3.2.1.41) in a process. The enzyme of the invention may also substitute for pullulanase in many processes that solely utilize pullulanase.

If desired, the enzyme of the invention may be combined with other enzymes, including other glucoamylases, pullulanase, α-amylase, β-amylase, isoamylase, mutarotase, aldose-1-epimerase, glucose-oxidase, peroxidase, transglucosidase, pectinase (polygalacturonase), cellulase, and β-glucanase.

The enzyme of the invention is useful in applications requiring the hydrolysis of gelatinized starch, or the presence of a debranching activity. For example, such applications include starch analysis; the manufacture of glucose syrups, high-DE glucose syrups and high-maltose syrups, isomaltose production; the hydrolysis of maltose and maltodextrins; the preparation of high purity dextrose; maltotetraose and high maltose content starch hydrolysates; straight linear dextrin for use in food, medicines and cosmetics; rice preparations that lack stickiness; the preparation of food fibers by the enzymatic treatment of seed husks or brans, and especially those of food fibers such as corn hull hydrolysis or maize husks, rice husks, husks of soy beans, skins of peanuts, and brans of rice, wheat, barley, oat, adlay, rye, and especially the elimination of serum cholesterol elevation factor from wheat bran; highly stable emulsions useful in the preparation of chocolate; alcohol from starches; sake production; beer production, especially low-calorie (light) beer wherein the unfermentable carbohydrate dextrin is broken down into fermentable sugars by glucoamylase action; the assay of starch contents of various biological materials, the assay of α-amylase; the production of polysaccharides with improved rheological properties over raw starch; the production of crystalline 2-O-alpha-D-glycopyranosyl-L-ascorbic acid; lubricants and gels; the synthesis of branched cyclodextrin; as an addition to laundry and dish washing detergents; in enzyme electrodes and multi-enzyme electrodes; for fragments containing the starch-binding domain for the preparation of genetically engineered peptide affinity tails for the recovery of fusion proteins; in wood and textile industry applications such as, for example, the preparation of plywood adhesives and particle board binders and saccharification of lignocellulosic materials; the preparation of high solid dextrin adhesives for the high speed coating of paper and wrinkle-free conversion of paper to envelopes, poster board, etc.; the preservation of protein containing animal or vegetable fodder; the production of polysaccharides such as xanthine by aerobic fermentation of microorganisms wherein fermentation occurs in the presence of starch and an amylolytic enzyme such as glucoamylase; improving the filterability of glucose syrups and/or lowering the viscosity of the same; lowering the viscosity of organic slurries in fermentation processes; the bioconversion of distillery wastes or vegetable wastes or fruit waste into feedstuff including feed additives, bulk fillers, sweetening agents, liquid feed components for farm animals, raw materials for ethanol production for consumption and as a fuel source; the preparation of feedstuff from meat by-products such as slaughterhouse, leather and good processing industry wastes; treatment of feeds and fodder to increase contents of reducing sugars, improve utilization of sugar present in such feedstuff including grass hays, mixed hays, legume hays, corn silage and rice straw; and assays to predict the digestibility of animal feeds. When used as a feed additive for food animals, the recombinant bacterial biomass may be added directly to the animal's fodder.

The examples below are for illustrative purposes only and are not deemed to limit the scope of the invention.

EXAMPLES

Materials a) Strains and vectors.

E. coli strain Y1090 (r⁻) was used as a host and λgt11-phage as a vector in λ-cDNA cloning. E. coli strains DH5α [F′, endA1, hsdR17, supE44, thi-1, recA1, gyrA96, relA1, 80d (prophage), ΔlacZ(M15)] (Hanahan, D., *J. Mol. Biol.* 166:557–580 (1983), and XL1-Blue {endA1, hsdR17(rk⁻, mk⁻), supE44, thi-1, lambda⁻, recA1, gyrA96, relA1, (lac⁻), [F′, proAB, lacI^qZ^ΔM15, Tn10 (tet^R)]} were used as hosts for constructions made of plasmids pIBI76 (Dente et al., *Nucleic Acids Res.* 11:1645–1655 (1983)), pAAH5 (Ammerer G., In: *Methods in Enzymology* 101:192–201 (1983)), and pALK100 (P. L. Suominen, Alko Ltd., unpublished). pALK 100 has been constructed from pALK 12 (Liljeström-Suominen et al., *Appl. Env. Microbiol.* 54:245–249 (1988)) by removing the 779 bp PstI-HindIII fragment containing the bla gene and adding an oligonucleotide linker containing BamHI and SmaI sites. *Saccharomyces cerevisiae* strain YF135 (α, leu2-3, leu2-112, his3-11, his3-15; Labatt Brewing Company Ltd., Production Research Department, POB5050, London, Ontario, Canada N6A 4M3) was used as a host in glucoamylase production. Fungal RNA was isolated from *Hormoconis resinae* strain ALKO304 (ATCC 20495).

b) Chemicals and Enzymes.

Zymolyase used in yeast protoplast preparation was from Seikagaku Kogyo (Tokyo, Japan). Restriction endonucleases, methylases, kinases, DNA polymerases and ligases were from Boehringer Mannheim (Germany) or New England Bio Labs (Beverly, Mass., USA). Oligo(dT)-cellulose (type 3) was from Collaborative Research, Inc. (Lexington, Mass., USA). Deoxynucleoside triphosphates, dideoxynucleoside triphosphates and protein molecular weight standards were from Pharmacia P. L. Biochemicals (Uppsala, Sweden). α-[³⁵S]-dATP, α-[³²P]-dCTP and γ-[³²P]ATP from Amersham (Buckinghamshire, U.K.) were used for labelling DNA. Oligonucleotides used in DNA sequencing and as probes were synthesized with an Applied Biosystems DNA synthesizer.

Example I

Cloning of H. Resinae Glucoamylase P

Methods

1. Preparation of Induced mRNA from *H. resinae*.

*H. resinae* was grown under conditions inducing glucoamylase production as described previously (Fagerström, R. et al., *J. Gen. Microbiol.* 136:913–920 (1990)) using starch as a carbon source, except that no glucose was used and 0.2% ammonium chloride was added to the growth medium. Frozen mycelia were ground to a powder in liquid nitrogen with a mortar and pestle followed by treatment with a Braun Mikro-dismembrator II. Total cellular RNA was isolated using the guanidinium thiocyanate procedure of Chirgwin et al., *Biochemistry* 18:5294–5299 (1979) and poly(A)⁺ RNA was purified by two cycles of oligo(dT) cellulose chromatography (Aviv et al., *Proc. Natl. Acad. Sci. USA* 69:1408–1412 (1972)).

2. cDNA Library Preparation.

The first strand of cDNA was synthesized using avian myeloblastosis virus reverse transcriptase (EC 2.7.7.49, Boehringer, Mannheim, Germany) and 10 µg of poly(A)⁺ RNA as a template. The RNase H-DNA polymerase I method of Gubler and Hoffman (Gubler et al., *Gene* 25:263–269 (1983)) was used for second-strand synthesis. Double stranded cDNA was methylated using EcoRI methylase, end-filled with T4 DNA polymerase and then ligated to EcoRI linkers (Pharmacia P.L. Biochemicals, Uppsala, Sweden) that had been first phosphorylated using T4 polynucleotide kinase and γ-[³²P]ATP. Following EcoRI digestion, cDNA was size fractionated by centrifugation in a sucrose gradient and a λgt11 cDNA library of fractions containing fragments 1.5–2.0 kb in length was constructed according to manufacturer's instructions (Protoclone, Promega, Madison, Wis., USA).

3. Screening of λgt11 Recombinants with Anti-Glucoamylase Antibodies.

Polyclonal antibodies against purified *H. resinae* glucoamylase P were raised in rabbits and purified by affinity chromatography (Fagerström, R. et al., *J. Gen. Microbiol.* 136:913–920 (1990)). About 10 plaque forming units (pfu) of λgt11 recombinants were plated on a petri dish containing a lawn of *E. coli* Y1090 (ATCC No. 37197) and plates were incubated at 42° C. until plaques became visible. Production of fusion proteins was induced with isopropyl thiogalactoside (IPTG) and the proteins were transferred to nitrocellulose membranes (Schleicher and Schuell, Dassel, Germany). Membranes were incubated with the antibody solution and recombinant plaques were identified using the anti-IgG-alkaline phosphatase method (Protoblot, Promega, Madison, Wis., USA).

4. Manipulation of DNA.

Restriction analysis, nick translation, DNA-ligation and electrophoresis of DNA and RNA were performed by standard methods (Maniatis et al., *Molecular cloning: A Laboratory Manual*, Cold Spring Harbor Laboratory, Cold Spring Harbor, N.Y. (1982)). Transformation of *E. coli* DH5α and XL1-Blue was performed as previously described (Hanahan, D., *J. Mol. Biol.* 166:557–580 (1983)). Plasmid isolations from *E. coli* were made using either CsCl-centrifugation (Maniatis a at., *Molecular Cloning: A Laboratory Manual*, Cold Spring Harbor Laboratory, Cold Spring Harbor, N.Y. (1982)) or alkaline SDS lysis (Birnboim et al., *Nucleic Acids Res.* 7:1513–1523 (1979)). DNA sequencing was performed by the dideoxy-chain termination method (Sanger et al., *Proc. Natl. Acad. Sci. USA* 74:5463–5467b (1977)) directly from plasmid DNA (Zagursky et al., *Gene Anal. Techn.* 2:89–94 (1986)).

5. Blot analysis.

Northern analysis of *H. resinae* mRNA using a synthetic oligonucleotide probe and Southern analyses of the cDNA clones using either full length cDNA or restriction fragments as probes were carried out according to Maniatis et al. (Maniatis et al., *Molecular Cloning: A Laboratory Manual*, Cold Spring Harbor Laboratory, Cold Spring Harbor, N.Y. (1982)). Western analysis of the yeast transformants was done by electrophoretically transferring proteins from a 6% SDS-PAGE gel (Laemmli, U.K., *Nature* 227:680–685 (1970) onto a nitrocellulose membrane (Promega, Madison, Wis., USA). The membrane was treated with anti-glucoamylase-antibodies, anti-IgG-alkaline phosphatase conjugate and a color reagent according to manufacturer's instructions (Protoblot, Promega, Madison Wis., USA).

6. Yeast transformation.

Figure 6:
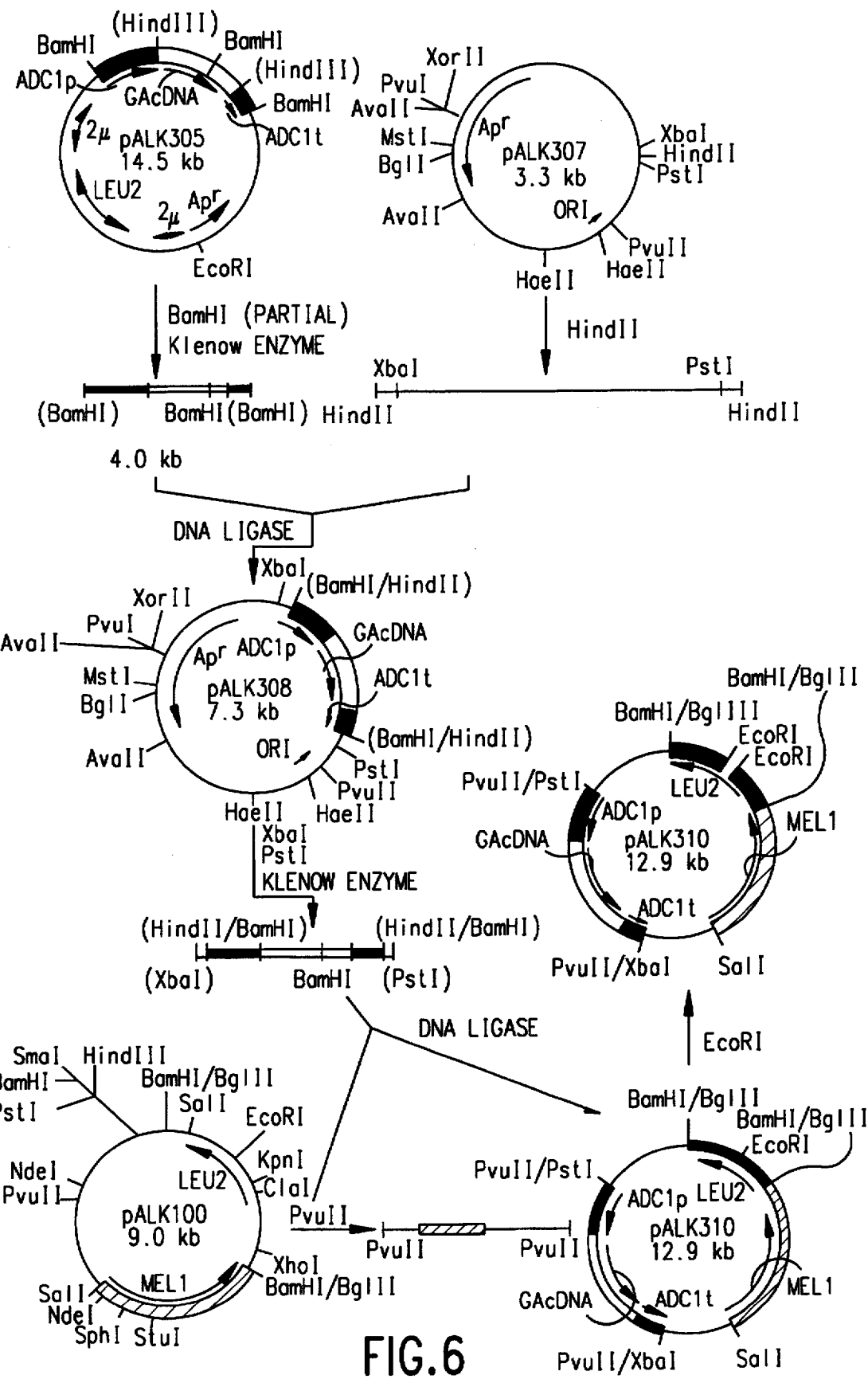
FIG. 6 shows the construction of the yeast integration vector pALK310. The vector was constructed by ligating an end-filled BamHI fragment from pALK305 to the HindIII site of the polylinker region of pALK307 (a pIBI76 derivative where a 941 bp NaeI-PvuI fragment had been deleted).

Transformation of the yeast strain YF135 with pALK305 was done by electroporation of intact cells (Hashimoto et al., *Appl. Microbiol. Biotechnol.* 21:336–339 (1985)) using a Gene Pulser transfection apparatus (Bio-Rad Laboratories, Richmond, Calif., USA) with a pulse intensity of 2.5 kV/cm and a capacitance of 1 μF. Because of the low transformation frequency of yeast with the integrative plasmid pALK310 (FIG. 6), a combination of spheroplasting and electroporation was developed. Spheroplasts were made essentially as described previously (Beggs, I. D., *Nature* 275:104–109 (1978)) except that cells were treated with zymolyase (2.5 μg/ml). Plasmid DNA was linearized prior to transformation by cutting with EcoRI in the middle of LEU2 to allow integration into the chromosome by homologous recombination. Spheroplasts were given a single pulse of 0.125 kV/cm and 250 μF. They were then regenerated and plated as described (Beggs, J. D., *Nature* 275:104–109 (1978)) except that incubations took place overnight before plating.

7. Enzyme activity tests.

Yeast strains were grown in batch culture in YPD (1% yeast extract, 2% peptone, 2% glucose) medium. Samples of growth medium were concentrated by ultrafiltration using Centricon-30 concentrators (Amicon, Danvers, Mass., USA). The remaining glucose in the concentrate was removed by washing with 0.2M sodium acetate buffer, pH 4.3. For the intracellular glucoamylase assay, yeast cells were ground under liquid nitrogen and disrupted with a Braun Mikro-dismembrator II. The disrupted cells were suspended in 50 mM sodium acetate, pH 4.3 containing 1 mM phenyl methyl sulphonyl fluoride (PMSF) and cell walls were removed by centrifugation. Glucoamylase activity was measured as described previously (Fagerström et al., *J. Gen. Microbiol.* 136:913–920 (1990)). α-Galactosidase and β-galactosidase activities on plates were detected using either of two chromogenic substrates, 5-bromo-4-chloro-3-indolyl-α-D-galactopyrasonide (X-α-gal, (Tubb et al., *J. Inst. Brew.* 92:588–590 (1986)); or 5-bromo-4-chloro-3-indolyl-β-D-galactopyranoside (X-β-gal (Miller et al., *Experiments in molecular genetics*, Cold Spring Harbor Laboratory, Cold Spring Harbor, N.Y. (1972)).

Results

Results from the Preparation and Screening of the *Hormoconis resinae* cDNA Library.

Figure 1:
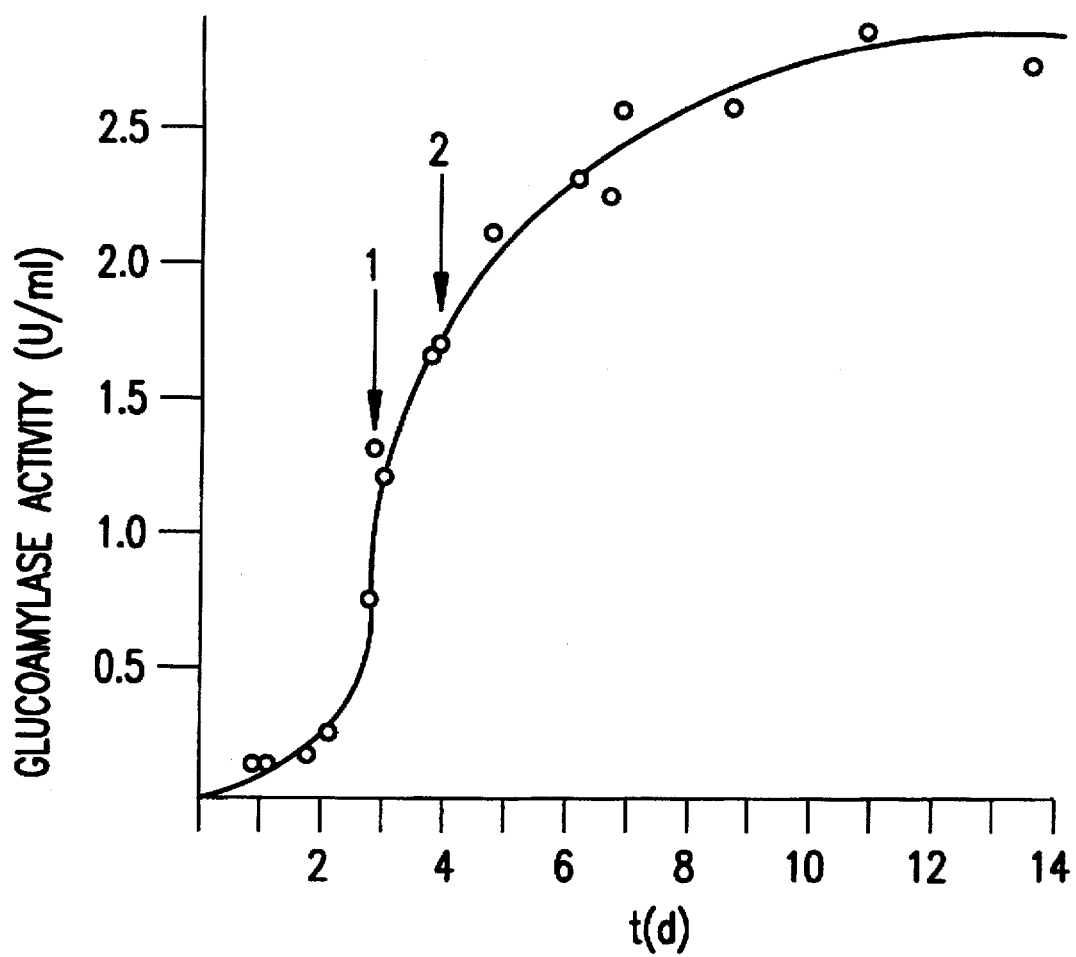
FIG. 1 shows the appearance of glucoamylase enzymatic activity in the growth medium of *H. resinae* at different time points. Poly(A)$^+$ RNA was isolated from cells at growth phases 1 and 2.

Glucoamylase activity in the growth medium was assayed during the growth of *H. resinae* and samples of fungal mycelia for poly(A)$^+$ RNA isolation were taken as the activity started to increase (FIG. 1). A mixture of oligonucleotides was synthesized containing the nucleotide permutations complementary to the amino acid sequence Ala-Asn-Pro-Asp-Tyr-Phe (Seq ID No. 7). This peptide corresponds to a region near the N-terminus of the mature *H. resinae* glucoamylase P (Fagerström et al., *J. Gen. Microbiol.* 136:913–920 (1990)).

Figure 2:
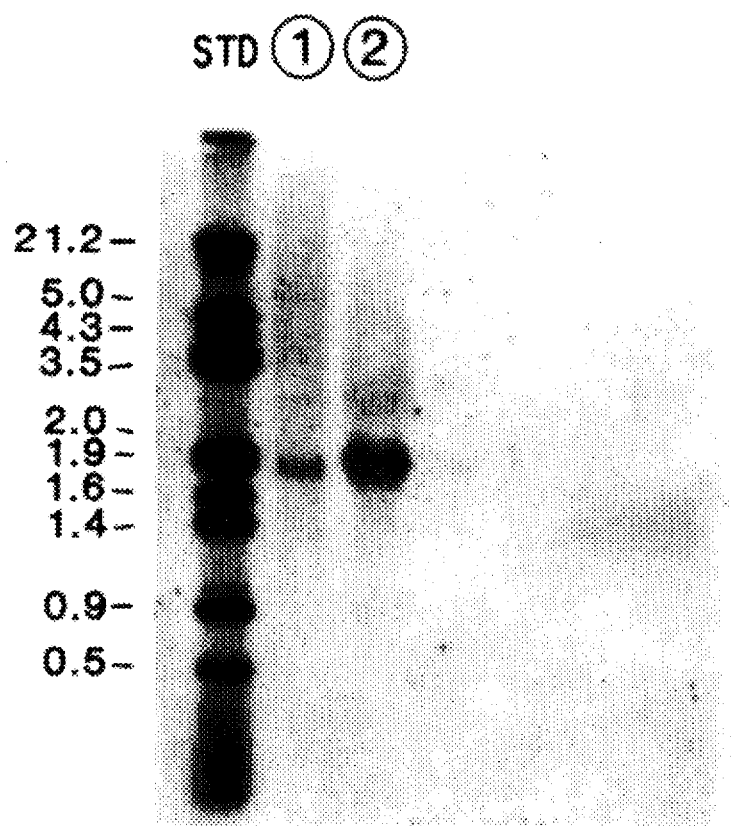
FIG. 2 shows a Northern hybridization of poly(A)$^+$ RNA fractions 1 and 2 isolated from *H. resinae*. The probe consisted of a radiolabeled oligonucleotide complementary to an amino acid sequence found in purified *Hormoconis resinae* glucoamylase P. The poly(A)$^+$ RNA fraction 2, rich in glucoamylase mRNA, was used as a template for cDNA synthesis.

Northern blot analysis of the isolated poly(A)$^+$ RNA samples probed with the radiolabeled synthetic oligonucleotide revealed a fraction, designated "fraction 2", containing most of the glucoamylase mRNA (FIG. 2). This fraction was used as a template for cDNA synthesis. cDNA was size fractionated by centrifugation in a sucrose gradient and fractions containing fragments of 1.5–2.0 kb were used for preparation of a λgt11 library. The cDNA library was screened with polyclonal antiglucoamylase antibodies and three positive clones were found.

Example II

Structure of the Glucoamylase P cDNA.

Figure 3:
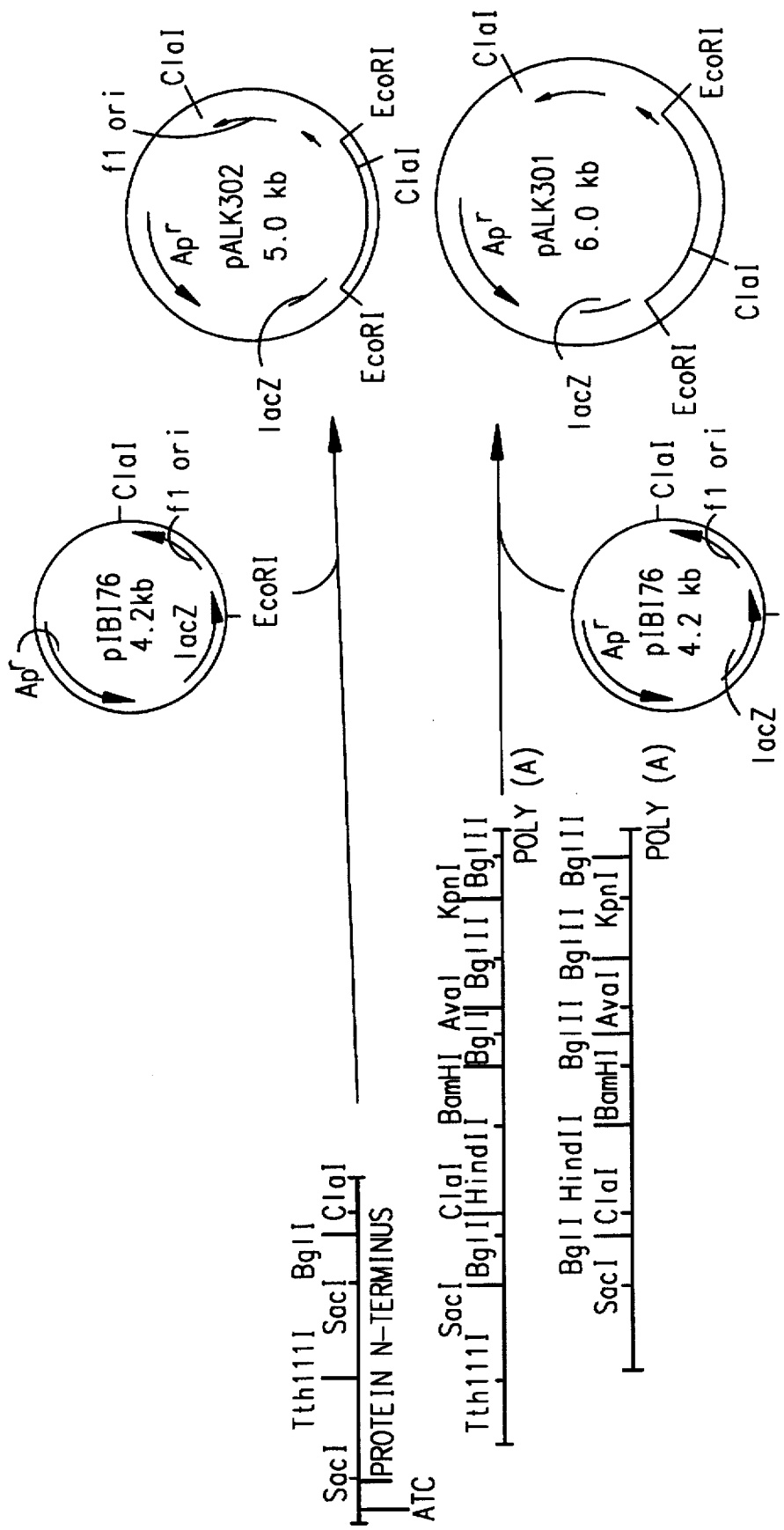
FIG. 3 shows a partial restriction map of the glucoamylase cDNA clones I, II, and III. The overlapping parts of the fragments are aligned. The initiation codon, the mature protein N-terminus and the 3'-poly A region are indicated.

The cDNA inserts from the λgt11 library were subcloned and analyzed in pIBI76. Restriction analysis, Southern blotting and nucleotide sequencing revealed that the inserts were partly overlapping. Insert I (1.0 kb) contained the initiation codon ATG as well as the part of the gene coding for the N-terminal portion of the protein. Insert II (1.8 kb) contained the portion of the gene coding for the C-terminal part of the protein as well as the poly A-tail of the mRNA. Insert III (1.6 kb) was another C-terminal coding cDNA fragment (FIG. 3).

Figure 4:
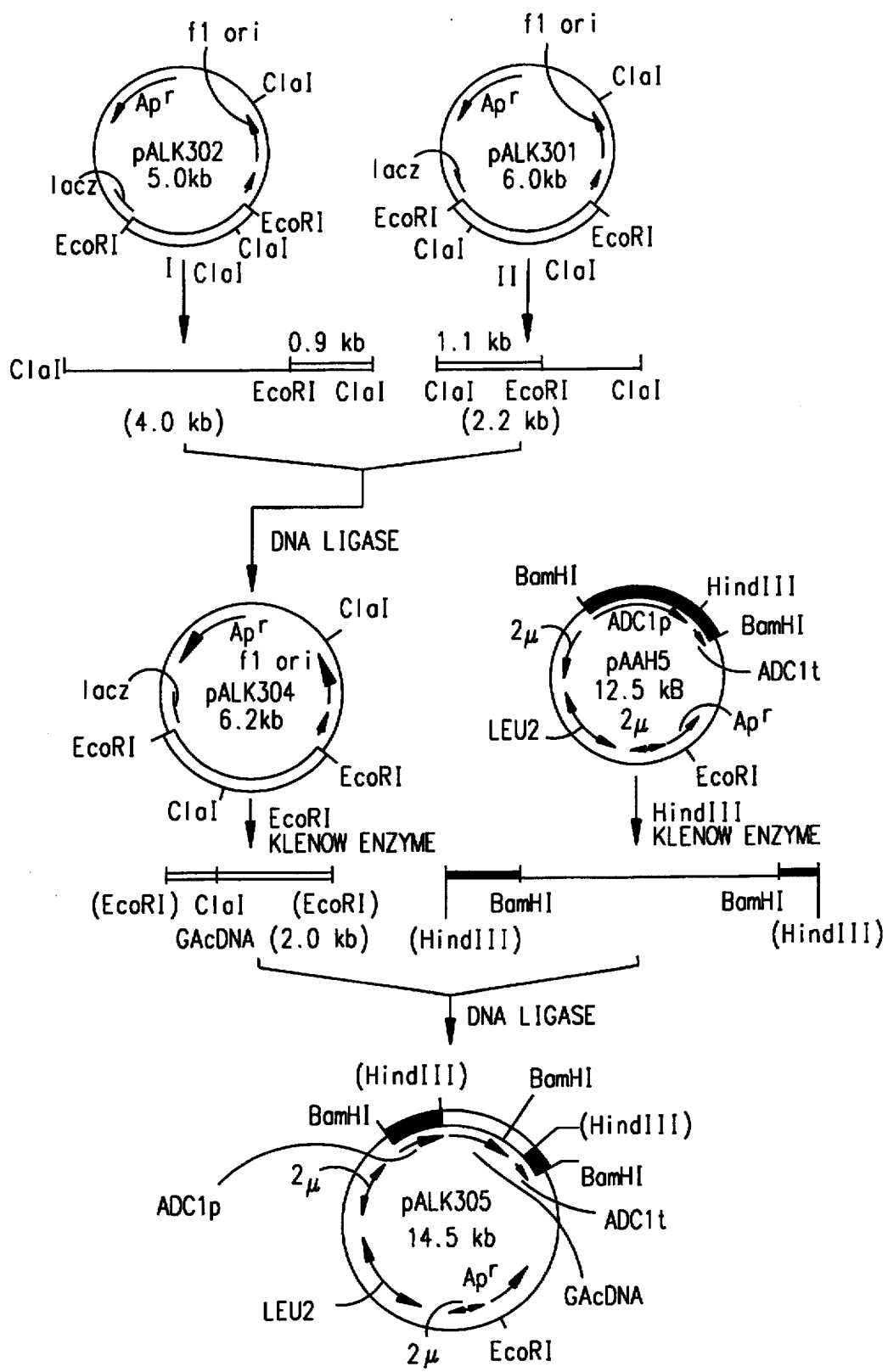
FIG. 4 shows the construction of the complete, full-length glucoamylase cDNA from overlapping fragments I and II cloned in pIBI76. Also shown is the construction of the glucoamylase expression vector pALK305. Plasmids pALK301 and pALK302 were digested with ClaI and the resulting halves containing the 5'-terminal gene portion (from pALK302) and the 3'-terminal gene portion (from pALK301) were ligated together to form pALK304. pALK304 contains the full-length glucoamylase cDNA. For the construction of pALK305, pAAH5 was cut with HindIII at the cloning site between the ADC1 promoter and terminator and the cDNA insert was excised from pALK304 with EcoRI. The sticky ends of the vector and insert were filled using the Klenow enzyme and the fragments were ligated together. The correct orientation was checked with BamHI digestion.

The complete cDNA was constructed from pALK301 and pALK302 by digesting the plasmids with ClaI. This enzyme cuts the cDNA once in the overlapping area and once in the vector itself. Fragments of correct size were purified and ligated together to form pALK304 which contains the final cDNA (FIG. 4).

The nucleotide sequence of the final cDNA (FIG. 5) contains one open reading frame of 1848 base pairs coding for a protein of 616 amino acid residues. The sequence was verified by comparison with peptides sequenced from the purified glucoamylase P (Fagerström et al., *J. Gen. Microbiol.* 136:913–920 (1990)).

Comparison of the deduced amino acid sequence with the N-terminal sequence of the purified glucoamylase P (Fagerström et al., *J. Gen. Microbiol.* 136:913–920 (1990)) revealed a signal peptide of 29 amino acid residues. Thus, the mature protein contains 587 amino acids corresponding to a molecular mass of 66 kDa. The protein has seven potential N-glycosylation sites (Asn-X-Ser/Thr).

Comparison of the *H. resinae* glucoamylase P amino acid sequence with that of other fungal glucoamylases showed it to be highly homologous to the glucoamylases of: *Aspergillus awamori*, 47.7%, (Nunberg et al., *Mol. Cell Biol.* 4:2306–2315 (1984)); *Rhizopus oryzae*, 36.6%, (Ashikari et al., *Agric. Biol. Chem.* 50:957–964 (1986)); *Saccharomycopsis fibuligera*, 37.6%, (Itoh et al., *J. Bacteriol.*

169:4171–4176 (1987)); *Saccharomyces diastaticus*, 36.7%, (Yamashita et al., *J. Bacteriol.* 161:567–573 (1985)); and *Saccharomyces cerevisiae*, 36.6%, intracellular, sporulation-specific glucoamylase, (Yamashita et al., *J. Bacteriol.* 169:2142–2149 (1987)). In contrast, no significant homology was found with the glucoamylase of *Schwanniomyces occidentalis* (Dohmen et al., *Gene* 95:111–121 (1990)). In addition, the amino acid sequence of *H. resinae* glucoamylase P did not contain the serine/threonine rich area (TS-region) (Vainio et al., *Curr. Genet.*, 24:38–44 (1993)) of *Aspergillus awamori* (Svensson et al., "Structure function relationships," in Friedmann R. B. (ed.), *Biotechnology of amylodexytrin oligo saccharides*, American Chem. Soc., Washington, D.C. (1991)).

At the nucleotide level, homologies were: 51.3% with *A. awamori*, 39.1% with *R. oryzae*, 33.9% with *S. fibuligera*; 31.3% with *S. diastaticus*; and 28.0% with *S. cerevisiae*. A putative polyadenylation signal TATAAA was found 32 bp upstream of the poly(A) tail and the sequence TCATC ATGCG, which resembles the consensus sequence in genes of other filamentous fungi (Gurr et al., In: *Special Publications of the Society for General Microbiology*, (Kinghorn, J. R. ed.) Vol. 22, *Gene Structure in Eukaryotic Microbes; Society for General Microbiology Symposium*, St. Andrews, Scotland, U.K. XVI+296P (1987), pp. 93–140), was found at the translation initiation site.

Example III

Expression of Glucoamylase P in *S. cerevisiae*.

For the expression of glucoamylase cDNA in yeast, we chose the constitutive yeast promoter, ADC1. The cDNA insert was cut from pALK304 and blunt-end ligated to the HindIII site between the ADC1 promoter and terminator in pAAH5, a 2µ based yeast-*E. coli* shuttle vector (FIG. 4). The resulting plasmid, pALK305, was used to transform YF135, a Leu⁻ laboratory strain and the transformants were identified using leucine selection. Yeast transformants containing autonomously replicating plasmids were unstable. One of the transformants, ALKO2313 had lost 50% of its pALK305 plasmids after 16 generations of growth without selection.

In order to obtain stable expression, an integration vector was constructed. A DNA fragment containing the glucoamylase cDNA with the ADC1 promoter and terminator was inserted into the PvuII site of pALK100, a plasmid containing MEL1 for positive selection of transformants (Tubb et al., *J. Inst. Brew.* 92:588–590 (1986)) and LEU2 for integration by homologous recombination into the LEU2 gene in the yeast genome (FIG. 6). pALK310-integrants were stable (no plasmid loss after 16 generations) and contained up to 24–26 copies of the plasmid in the genome. The copy number of the integrants was determined by Southern blot analysis and the amount of glucoamylase produced by different integrants appeared to be a function of the copy number. The glucoamylase activities of the yeast transformants are shown in Table 1. The amount of enzyme secreted into the medium was 0.6–1.1 mg/l, corresponding to 99% of the total glucoamylase P produced. Debranching activity was about 70% of the starch-degrading activity.

Western blot analysis revealed that the glucoamylase P produced by the yeast transformants migrates as a diffuse band, part of which consists of higher molecular weight forms than glucoamylase P produced by *H. resinae*. This may be due to variable and excessive glycosylation by the yeast cells. After endoglycosidase treatment the glucoamylase P from yeast appeared as a sharp band of the same apparent molecular mass as the deglycosylated enzyme from *H. resinae*.

TABLE 1

Glucoamylase activity produced by the *S. cerevisiae* transformants and the host strain

| Strain[a] | Plasmid[b] | Glucoamylase activity[c] | | |
|---|---|---|---|---|
| | | (U/l), starch | (U/l), pullulan | (mg/l)[d] |
| YF 135 | secreted[e] | — | 0.03 | — | 0.002 |
| " | cellular | — | — | — | — |
| ALKO2313 | secreted | pALK305 | 15.9 | 12.2 | 1.10 |
| " | cellular | " | 0.03 | 0.02 | 0.002 |
| ALKO2522 | secreted | pALK310 | 8.5 | 5.4 | 0.59 |
| " | cellular | " | 0.05 | 0.03 | 0.003 |

[a]Strain YF135 is described in Materials. ALKO2313 is YF135 containing the autonomously replicating pALK 305 and ALKO2522 is YF135 containing the integrated pALK310.
[b]For maps and description of the plasmids, see FIGS. 4 and 6. pALK305 contains the glucoamylase cDNA (2.0 kb) inserted into the HindIII site of pAAH5. pALK310 is a 4.0 kb DNA fragment that contains the glucoamylase cDNA and ADC1 promoter and terminator from pALK305 inserted into the PvuII site of pALK100 as described in the Brief Description of the Drawings and Example III.
[c]Activity was determined as described previously (Fagerström et al., J. Gen. Microbiol. 136:913–920 (1990)) using either starch or pullulan as a substrate. One unit was defined as the amount of glucoamylase releasing 1 µmol glucose per minute at 30° C. The values are the highest obtained during batch culture growth.
[d]The values were calculated from the activity data obtained using starch as a substrate and the specific activity of 14.4 U/mg at 30° C.
[e]The samples for the assay of the secreted and cellular glucoamylase were prepared as described in Methods. Cellular activity represents the activity found in cells harvested from one liter of culture medium.

Discussion

Expression of genes from filamentous fungi in *S. cerevisiae* is often prevented by the presence of introns found in genomic DNA. The cDNA of *H. resinae* gamP coding for glucoamylase P has been cloned by combining two clones from a cDNA bank. Comparison of the nucleotide sequences of the cDNA clones and the genomic gene (below) revealed that introns were present in the area of both original cDNA clones. The cDNA directed the expression and secretion of active glucoamylase P into the growth medium.

Western blot analysis shows that the apparent molecular mass of the secreted glucoamylase P was variable but larger than the 71 kDa of the original enzyme from *H. resinae* (Fagerström, R. et al., *J. Gen. Microbiol.* 136:913–920 (1990)). This is understandable because of the tendency of yeast to hyperglycosylate proteins. The molecular mass of the deglycosylated enzyme secreted by both *S. cerevisiae* and *H. resinae* was about 63 kDa, only slightly different from the value calculated from the nucleotide sequence, 66 kDa.

The amino acid composition according to the sequence analysis corresponds well with the results from the amino acid analysis of the purified protein (Fagerström, R. et al., *J. Gen. Microbiol.* 136:913–920 (1990)). The pattern of codon usage resembles that of *Aspergillus* but not of *Saccharomyces* (Ballance, D. J., *Yeast* 2:229–236 (1986)). This might be one reason for the low expression level of this gene in yeast. Another reason could be the different sequences at the translation initiation sites of yeast and filamentous fungi. The sequence surrounding the translation initiation codon ATG of *H. resinae* gamP resembles the eukaryotic consensus sequence as the sequences of other gene of filamentous fungi, but it differs especially from the sequences of highly expressed yeast genes by having a C at position −1 instead of A and by having CGC, not TCT as the second translated triplet (Hamilton, R. et al., *Nucl. Acids Res.* 15:3581–3593 (1987)).

The signal peptide of glucoamylase P contains a typical hydrophobic core and an arginine residue near the N-terminus. A typical eukaryotic signal peptidase cleavage site (von Hejne, G., *Eur. J. Biochem.* 133:17–21 (1983)) is surprisingly found between amino acid residues −1 and −2 counted from the experimentally determined N-terminal residue, aspartic acid (Fagerström, R. et al., *J. Gen. Microbiol.* 136:913–920 (1990)). It seems that the arginine residue is proteolytically cleaved off after the action of signal peptidase. Nevertheless, glucoamylase P is effectively secreted from *S. cerevisiae* using its own signal peptide.

The debranching activity of glucoamylase P secreted from yeast is about 70% of the α-1,4-glycosidic activity, the same as that of the enzyme purified from *H. resinae*. On the contrary, the debranching activity of the mixture of glucoamylase P and S secreted into the growth medium of *H. resinae* is only 20% (Fagerström, R. et al., *J. Gen. Microbiol.* 136:913–920 (1990)). Although the amount of glucoamylase P secreted by yeast is rather low, the expression of gamP cDNA enables the yeast to produce a glucoamylase with high debranching activity.

Example IV

Expression of Glucoamylase P in *T. reesei*

TABLE 2

Plasmids used in this example

| Plasmid | Relevant features | Source/Reference |
|---|---|---|
| p3SR2 | Ap$^r$, amdS | Hynes et al., Mol. Cell. Biol. 3:1430–1439 (1983) |
| pAMH110 | Ap$^r$ cbh1 expression cassette | US Patent Appls. 07/044,077 and 07/496,155, incorporated herein by reference |
| pALK304 | Ap$^r$, Glucoamylase P cDNA | This work |
| pALK601 | Ap$^r$, amdS cbh1 expression cassette | This work |
| pALK602 | Ap$^r$, amdS cbh1 expression cassette, Glucoamylase P cDNA | This work |

TABLE 3

*T. reesei* strains used in this example

| RUT-C-30 | Montenecourt et al., Appl. Environ. Microbiol. 34:777–782 (1977); ATCC 56765 |
| ALKO2221 | Alko Culture Collection |
| ALKO2742 | This work |
| ALKO2743 | This work |
| ALKO2744 | This work |

RUT-C-30 (ATCC 56765) is a strain in which the aspartic protease activity is not detected when assayed according to the method described in "Proteolytic activity, fungal (HUT); Food Chemical Codex (1982) 2nd edition, pp. 496–497, editor Committee on code Specifications, National Academy Press, Washington."

ALKO 2221, a UV-mutant of industrial strain ALKO 233 with 10 times lower proteolytic activity than the original strain used. (Aria Mäntylä, Alko Ltd.)

1. Construction of plasmid pALK601.

Plasmid pALK601 is an expression vector for the expression of recombinant genes in *Trichoderma reesei*. The gene to be expressed is inserted between the promoter and terminator regions of the *T. reesei* cbh1 gene. The plasmid also contains the AmdS gene from *Aspergillus nidulans* as a fungal selection marker and both the Ap$^r$ gene and origin of replication for propagation in *E. coli* (FIG. 7).

pALK601 was constructed as follows: Plasmid p3SR2 (Hynes et al., *Mol. Cell. Biol.* 3:1430–1439 (1983)) was digested with SacII and treated with mung bean nuclease in order to get blunt ends. These ends were ligated together with T4-ligase and the ligation mixture was used to transform *E. coli* cells.

One recombinant, lacking a SacII site, was partially digested with NdeI. It was then treated with the large fragment (Klenow) of DNA polymerase I and all four dNTP's to generate filled-in restriction ends. The ends were ligated together and the ligation mixture was used to transform *E. coli* cells.

One recombinant, in which the NdeI site in the pBR322 region was removed, was digested with SalI and SphI enzymes and the 8.2 kb fragment was purified in a LMP-agarose gel (Bethesda Research Laboratory, USA), isolated by phenol extraction and treated with calf intestinal phosphatase (CIP) in order to remove the 5'-terminal phosphate.

The plasmid pAMH110 was also digested with SalI and SphI. The 2.8 kb fragment containing the cbh1 expression cassette (cbh1 promoter and terminator joined by a stuffer fragment) was purified in a LMP-agarose gel and isolated by phenol extraction. This fragment was ligated to the SalI-SphI p3SR2 fragment using T4-ligase and the ligation mixture was used to transform *E. coli*.

One recombinant containing the cbh1 expression cassette in the modified p3SR2 plasmid was further digested with EcoRI and KpnI and the larger, 9.9 kb, fragment was purified in a LMP-agarose gel. The fragment was isolated by phenol extraction and treated with mung bean nuclease in order to get blunt ends. These were ligated together with T4-ligase and the ligation mixture was used to transform *E. coli* cells.

The final recombinant plasmid which contained the desired structure was named pALK601. It contains the *E. coli* Ap$^r$ gene and origin of replication for propagation in *E. coli*, the amdS gene for acetamide selection and the cbh1 expression cassette for foreign gene expression in *Trichoderma reesei*. The small stuffer fragment flanked by SacII and NdeI restriction sites is replaced by a novel gene, that is, a recombinant gene whose expression is sought.

2. Construction of plasmid pALK602.

Plasmid pALK602 consists of plasmid pALK601 with *Hormoconis resinae* glucoamylase P cDNA, inserted into the cbh1 expression cassette (FIG. 8).

*Hormoconis resinae* glucoamylase cDNA was obtained as an EcoRI insert in plasmid pALK304 (FIG. 4). It was removed from the pALK304 by EcoRI digestion, purified in a LMP agarose gel and isolated by phenol extraction. The purified and isolated fragment was treated with the large fragment (Klenow) of DNA polymerase I in the presence of all four dNTP's in order to obtain filled-in ends.

Plasmid pALK601 was partially digested with NdeI (in addition to the NdeI site restricting the stuffer fragment, pALK601 contains another NdeI site in the first intron of the amdS gene) followed by total digestion with SacII. The stuffer-free, linearized form of plasmid pALK601 was purified in a LMP-agarose gel, isolated by phenol extraction, treated with mung bean nuclease to generate blunt ends and finally treated with calf intestinal phosphatase (CIP) in order to remove the 5'-terminal phosphate. The glucoamylase cDNA fragment was inserted into linearized pALK601 and the ligation mixture was used to transform *E. coli* cells. The recombinant containing the desired structure was identified using restriction enzyme digestion and was named pALK602.

3. Transformation of *Trichoderma reesei* with plasmid pALK602.

Spores of *Trichoderma reesei* strains ALKO2221 and RUT-C-30 (ATCC 56765), which lack aspartic protease activity and which are suitable for heterologous protein expression, were grown on 3.9% potato dextrose plates covered with cellophane membranes for about 20 hours at 30° C.

The mycelium was harvested by soaking the membranes in a Petri dish containing 15 ml of 5 mg Novozym 234 (NOVO A/S, Denmark)/1 ml 1.2M $MgSO_4$-10 mM $NaH_2PO_4$ pH 5.8, solution. The Petri dish was incubated with gentle agitation for 1.5-2 hours at 30° C. and the suspension was then filtrated through sintered glass (porosity 1).

The filtrate was transferred to a sterile centrifuge tube and overlayed with an equal volume of 0.6M sorbitol-0.1M Tris-HCl pH 7.0 (Kinghorn, J. R. (Ed.), *Special Publications of the Society For General Microbiology*, Vol. 22, "Gene Structure In Eukaryotic Microbes" Society For Gen. Microbiol. Symp., St. Andrews, Scotland, UK XVI+296p. IRL Press (Oxford, England, UK; Washington D.C., USA) (1987)). Centrifugation was performed for 15 minutes at 4000× g. Protoplasts were collected from the top of the $MgSO_4$ cushion and transferred to a new sterile centrifuge tube. An equal amount of 1.2M sorbitol-10 mM Tris-HCl pH 7.5 was added to the protoplast suspension and the mixture was centrifuged for 5 minutes at 4000× g. Protoplasts were washed two more times with the 1.2M sorbitol-10 mM Tris-HCl pH 7.5 solution and then suspended to a density of $5×10^5$-$5×10^7$/ml in a solution of 1.2M sorbitol −10 mM $CaCl_2$-10 mM Tris-HCl pH 7.5.

200 µl of the protoplast suspension was incubated at +48° C. for 5 minutes, transferred to 0° C. for 30 seconds and finally held at room temperature for 5 minutes. 5-10 µg of purified pALK602 (purified by centrifugation on a CsCl/EtBr gradient and passage through Biogel P-30 column) in a volume of 10-20 µl of 10 mM Tris-HCl-1 mM EDTA pH 7.5 was mixed into the suspension. 50 µl of 25% PEG 6000-50 mM Tris-HCl pH 7.5 was then added and the resulting solution carefully mixed.

The mixture was incubated at +0° C. for 20 minutes and 2 ml of 50 mM $CaCl_2$-10 mM Tris-HCl pH 7.5 solution was added. The solution was then carefully mixed and left at room temperature for 5 minutes. Finally, 4 ml of 1.2M sorbitol-10 mM Tris-HCl pH 7.5 solution was added and the suspension was mixed gently. 250-1000 µl quantities were plated in an agar overlay onto Trichoderma minimal plates (Penttilä et al., *Gene* 61:155-164 (1987)).

The plates contained 1M sorbitol as an osmotic stabilizer, 10 mM acetamide as a sole nitrogen source for selection of acetamidase positive transformants and 15 mM CsCl to inhibit background growth. The top agar contained the same components except that the solidifying agent was 3% agarose instead of 2% agar. Plates were incubated at 30° C. for 5-7 days.

4. Determination of 1,6-Glucosidic Bond Hydrolysis By Glucoamylase P.

For glucoamylase activity determination, transformants or untransformed hosts were grown in 50 ml of 4% whey—complex nitrogen source-1.5% $KH_2PO_4$-0.5% $(NH_4)_2SO_4$ medium for 7 days at 30° C. with vigorous shaking. The cultures were centrifuged for 5 minutes at 4000× g and 10-50 µl of each supernatant fraction was transferred to a 1.5 ml Eppendorf tube. The volume was adjusted to 400 µl with distilled water. 100 µl of 5% pullulan solution and 500 µl of 0.2M $CH_3COONa$ pH 4.3 buffer were added and the tube was mixed quickly. A sample of 50 µl was taken immediately and transferred to 100° C. for 3 minutes. The tube containing the remainder of the sample was incubated at 30° C. and samples of 50 µl were taken at defined times.

The amount of glucose generated at each time point was determined using the Glucose Mercotest Kit 14335 (E. Merck). 500 µl of Gluc-DHG reagent was added to the samples. The tubes were mixed vigorously and left at room temperature for 30-60 minutes. After this incubation, the $OD_{340}$ was measured and glucoamylase activity. (1 U=µmol glucose liberated/min at 30° C.) was calculated by using standard glucose.

The specific activity of the *Hormoconis resinae* glucoamylase enzyme is 9 µmol glucose liberated/min/mg at 30° C. with pullulan as a substrate. Using this value, the amount of *H. resinae* glucoamylase secreted by *Trichoderma reesei* transformants can be estimated.

5. Shaker Flask Cultivations

Well-growing transformant clones were dispersed in 0.9% NaCl-0.01% Tween 20 solution and plated onto selective medium (Trichoderma minimal plates containing 10 mM acetamide, 0.1% Triton X-100 and 15 mM CsCl) so that each clone originated from a single spore. They were grown in 50 ml of 4% whey—complex nitrogen source-1.5% $KH_2PO_4$-0.5% $(NH_4)_2SO_4$ medium for 7 days at 30° C. with vigorous shaking and then centrifuged for 5 minutes at 4000× g. Glucoamylase activity was determined as described above. The amount of glucoamylase varied significantly between different clones. The glucoamylase activities obtained are shown in Table 4a as U/ml and in Table 4B as U/liter on various substrates. Three highly secreting *T. reesei* ALKO2221 transformants were preserved and were named ALKO2742, ALKO2743 and ALKO2744. The best transformant (ALKO2743) produced 40-50 times more 1,6-glycosidic bond hydrolyzing activity compared to the non-transformed host. The strains listed in Table 4a and 4b are all *T. reesei* strains.

TABLE 4a 1,6-glucosidic bonds hydrolyzing activity in flask cultivations

| Strain | Plasmid | Glucamylase activity (U/ml) |
|---|---|---|
| ALKO2221 | — | 0.2 |
| RUT-C30 | — | 0.1 |
| ALKO2743 | pALK602 | 8.2 |
| RUT-C30 | pALK602 | 5.1 |

TABLE 4b

Glucoamylase activities with different substrates

| | Glucoamylase activity on starch[a] (U/l) | Glucoamylase activity on pullulan[a] (U/l) | Heterologous glucoamylase (mg/l)[b] |
|---|---|---|---|
| ALKO2221 | 1380 | 513 | — |
| ALKO2742 (ALKO2221 transformed with pALK602) | 10600 | 6270 | 640 |
| ALKO2743 (ALKO2221 transformed | 11600 | 7290 | 710 |

TABLE 4b-continued

Glucoamylase activities with different substrates

| | Glucoamylase activity on starch[a] (U/l) | Glucoamylase activity on pullulan[a] (U/l) | Heterlogous gluco- amylase (mg/l)[b] |
|---|---|---|---|
| with pALK602) | | | |
| ALKO2744 (ALKO2221 transformed with pALK602) | 10700 | 7170 | 647 |
| Rut-C30 | 42.5 | 21.2 | — |
| ALKO3437 (Rut-C30 transformed with pALK602) | 7470 | 4630 | 516 |

[a]Glucoamylase activity determinations as described in (Fagerström, R. et al., J. Gen. Microb. 136:913–920 (1990))
[b]Calculated as mg/l of heterologous glucoamylase: the U/l (starch) value of the host strain was subtracted from the U/l value of the transformant and the difference was divided by the specific activity of 14.4 U/mg that was obtained when Zulkowsky starch was used as a substrate (Fagerström, R. et al., J. Gen. Microb. 136:913–920 (1990)).

By assuming that the specific activity of the secreted enzyme is the same as that of purified *H. resinae* glucoamylase P (GAMP), the concentration of heterologous glucoamylase secreted by the transformants in Table 4b was calculated to be between about 500 and 700 mg/l. This is an amount that is about twenty-fold higher than the concentration of 30–35 mg/l GAMP that *H. resinae* secretes into the growth medium. A comparison by immunoblotting of samples of a Trichoderma transformant culture filtrate with known amounts of *H. resinae* GAMP gave similar results, suggesting that most of the secreted heterologous glucoamylase, if not all, is in an active form. Pilot fermentations of ALKO2743 showed that the level of secreted GAMP obtained in shake flask cultivations is achieved in pilot fermentation scale, and the growth rate of the transformant strain ALKO2743 was similar to that of the parental strain ALKO2221.

By Northern analysis, the gamP mRNA produced in the ALKO2221 transformants is about 2.0 kb, similar to that found in *H. resinae*.

Monoclonal mouse antiserum raised against pure GAMP protein does not detect any protein in the growth medium of untransformed ALKO2221. In the Trichodmera gamP transformants however, the antibody detected a protein having a molecular weight more disperse than of the protein as secreted from *H. resinae* where the enzyme migrates as being about 71 kDa. This difference is due to different glycosylation patterns and after endoglycosidase H treatment the GAMP from *H. resinae* and the GAMP from Trichoderma both migrate as a compact 63 kDa band. No proteolytic degradation products of the GAMP were found with this antiserum in the growth medium of the low protease host ALKO2221.

Each of ALKO2742, ALKO2743 and ALKO2744 were further evaluated to determine the way in which the transforming plasmid integrated into the Trichoderma genome. Complex plasmid integration events are common in fungal species and known also in *T. reesei*. Southern blot analysis was performed against transformant and parental DNA that had been digested with XhoI. There are no XhoI sites in pALK602. There was an absence of any DNA that migrated with the free plasmid on the gel suggesting that the transforming plasmid integrated into the genomic DNA of *T. reesei* in each transformation event. In each event examined, the integrated plasmid sequences were carried on XhoI fragments that were quite large in size (greater than 20 kb), which may indicate the integration of multiple plasmid copies. Unlike the untransformed parental strain, each transformant contained all of the construction elements of plasmid pALK602 (as shown by probing with gamP, amdS, pBR322, and cbh1 specific probes. This suggests that transformation has occurred by integration of the entire pALK602 plasmid rather than only fragments of it into the genome of the host.

Digestion with XhoI cuts the *T. reesei* genomic cbh1 region so that the entire cbh1 gene with its promoter and terminator sequences remains on an 8.5 kb fragment. Because XhoI does not cut pALK602, a homologous integration between the cbh1 expression control elements of pALK602 and the genomic cbh1 gene increases the size of the cbh1 specific band in the transformant strain. This seemed to be the case in one of the transformants (ALKO2744), whereas the remaining two contained the 8.5 kb cbh1 fragment and an additional cbh1 specific band. This is most likely a result of nonhomologous plasmid integration, which may have happened through pBR322 or amdS sequences.

When the genomic DNA is digested with SacII, and probed with a gamP specific probe, there is a similar result of multiple and nonidentical plasmid integrations into the genome of the host strain ALKO2221 and each transformant contains several different sized copies of gamP cDNA. SacII cuts at only one site in pALK602.

Example V

Characterization of the purified recombinant protein and the unpurified (ALKO-GA) enzyme preparates from *T. reesei*.

1. Glucoamylase Preparations and Determination of Protein Concentrations:

The specific activity of purified glucoamylases was determined using a variety of substrates. The purified commercial preparation of *A. niger* glucoamylase was purchased from Sigma Chemical Co., St. Louis, Mich. (Sigma, A-3514 lot 14 F-0201, 10 mg/ml) and used directly. Glucoamylase P from *H. resinae* (ATCC 20495) was purified as described by Fagerström et al., *J. Gen. Microbiol.* 136:913–920 (1990).

Purification of recombinant glucoamylase P from *T. reesei* was performed as follows: Recombinant *T. reesei* (ALKO2743) culture medium (900 ml) was centrifuged at 10,000× g for 10 minutes. The supernatant (850 ml) was diluted with (400 ml) 0.3M potassium phosphate buffer pH 7.0 containing 3 mM MgCl$_2$ and 0.3 mM EDTA. Proteins were precipitated with 45% (W/V) (NH$_4$)$_2$SO$_4$ overnight at 5° C. The precipitate was collected by centrifugation for 20 minutes at 10,000× g. The precipitate was resuspended in 20 mM potassium phosphate buffer pH 6.5 (buffer I). This sample was desalted by running a Biogel P-30 column (Bio-Rad; 3×24 cm) equilibrated with buffer I. The desalted sample containing glucoamylase activity (assayed with soluble starch as substrate) was applied to a DEAE Sepharose CL-6B (Pharmacia) column (2.5×25 cm) equilibrated with buffer I at a flow rate of 90 ml/h. Elution was performed with a linear gradient from 400 ml buffer I to 400 ml buffer I containing 0.6M NaCl. Fractions of 7.5 ml were collected and assayed for enzymatic activity using both soluble starch and pullulan as substrate. Fractions eluting at less than 0.2M NaCl in buffer I showed only starch degrading activity. These were pooled and contained the *Trichoderma reesei* glucoamylase. The fractions containing both starch and pullulan degrading activity were pooled, diluted 2 to 1 with water, and applied to a second DEAE Sephadex CL-6B (2.5×15 cm) column equilibrated with 20 mM sodium acetate pH 5.5 (buffer II). Elution of the recombinant glucoamylase P was performed with a linear gradient 100 ml buffer II to 100 ml buffer II containing 0.6M NaCl at a flow rate of 80 ml/h. Fractions containing both starch and pullulan degrading activity were pooled and desalted with a Superdex 75 Hiload column (2.6×60 cm Pharmacia) equilibrated with 20 mM sodium acetate pH 4.0. In order to concentrate the sample, it was applied to a Mono Q ion exchanger (0.5×5 cm Pharmacia) equilibrated with buffer II and eluted with a linear gradient (30 ml) of 0 to 0.2 M NaCl in buffer II at a flow rate of 60 ml/h.

Zulkowsky Starch was from Merck and dextran T-10 from Pharmacia. All other substrates were from Sigma. Protein concentration of, purified glucoamylase was determined spectrophotometrically at 205 nm using the method of Scopes (Scopes, R.K., *Analytical Biochem.* 59:277–2829 (1974)); an $A^{1\%}_{1\ cm}$ value of 307 was used for glucoamylase P. In the case of glucoamylase from *A. niger* the values of protein concentration reported by Sigma (10 mg/ml) were used.

2. Determination of Specific Activity

Enzyme was incubated with 0.5% substrate in 0.2M sodium acetate buffer pH 4.3 containing 0.15 mg ovalbumin at 30° C. Samples of 100 μl were withdrawn at defined time points (between 0 and 120 minutes) and the released glucose was quantitated using the glucose dehydrogenase (Gluc-DHG, Merck) method and standard glucose.

Activity measurements were performed in duplicate and initial velocities were estimated from plots. Assay points were chosen at about 5% theoretical hydrolysis in order to minimize the effect of partially hydrolysed substrates. The results for maltose and isomaltose have been divided by two, since two glucose molecules are released for each hydrolysed bond.

Enzyme samples were diluted in order to get about equal absorbances at equal timepoints when using Zulkowsky starch as substrate. Protein concentrations used in the experiment were 0.2 μg/ml *A. niger* glucoamylase, 1.0 μg/ml glucoamylase P from *H. resinae* and 1.2 μg/ml glucoamylase P produced in *T. reesei*. Specific activity is expressed as μmol glucose released/min/rag enzyme.

Results are shown in the Table 5. The specific activity of *A. niger* glucoamylase is higher than that of glucoamylase P when Zulkowsky starch is used as substrate. This higher specific activity is less pronounced when maltose or maltotriose are used as substrate, and turns to the opposite for all the other substrates tested. Since limit dextrins contain many α-1,6-glucosidic bonds, the capability of glucoamylase to hydrolyze these bonds is especially important.

TABLE 5

Specific activities of the purified glucoamylases with different substrates

| | A. niger Glucoamylase (Sigma) μmol/min/mg | H. resinae Glucoamylase P (ATCC 20495) μmol/min/mg | Glucoamylase P from T. reesei (Alko 2743) μmol/min/mg |
|---|---|---|---|
| Starch (Zulkowsky) | 27.3 | 14.4 | 10.3 |
| Pullulan | 0.6 | 9.1 | 6.8 |
| Maltose | 4.0* | 3.1* | 2.2* |
| Maltotriose | 13.0 | 9.4 | 6.3 |

TABLE 5-continued

Specific activities of the purified glucoamylases with different substrates

| | A. niger Glucoamylase (Sigma) μmol/min/mg | H. resinae Glucoamylase P (ATCC 20495) μmol/min/mg | Glucoamylase P from T. reesei (Alko 2743) μmol/min/mg |
|---|---|---|---|
| Isomaltose | 0.2* | 0.6* | 0.5* |
| Isomaltotriose | 0.6 | 1.4 | 1.2 |
| Panose | 1.3 | 7.7 | 5.9 |
| Dextran T-10 | n.d. | 0.6 | 0.4 |

The specific activity is expressed as μmol glucose released/min/mg enzyme; *results divided by two;
n.d. not detectable even after 4 hours incubation.

3. Relative Activities of Glucoamylase Preparates

Relative activities of glucoamylase preparates compared are shown in Table 6. Activity measurements were performed as indicated above. The initial velocities of the reaction rates were compared so that the initial velocity of Zulkowsky starch hydrolysis was taken as 100%. The Novo preparate used was the commercially available Novo AMG 300 L (Batch AMN 4033). *T. reesei* preparate was the culture media of the transformant Alko 2743. The amount of enzyme units used in the experiment was the same for the Novo and the *T. reesei* preparate estimated using Zulkowsky starch (12.2 μmol/min/ml).

TABLE 6

Relative activities of the glucoamylase preparates with different substrates

| | % Relative Activity (Initial Velocity) | |
|---|---|---|
| | Novo AMG 300L | Alko-GA (T. reesei Alko 2743) |
| Starch (Zulkowsky) | 100 | 100 |
| Pullulan | 2 | 61 |
| Maltose | 29* | 46* |
| Maltotriose | 48 | 64 |
| Isomaltose | 1* | 9* |
| Isomaltotriose | 2 | 10 |
| Panose | 5 | 56 |
| Dextran T-10 | n.d. | 4 |

*results divided by two;
n.d. not detectable even after 4 hours incubation.

The results obtained with the unpurified enzyme preparates show that the *T. reesei* preparate is better in all cases than the Novo preparate even in digesting maltose and maltotriose. Purified enzymes did show an opposite effect in digesting shorter malto-oligosaccharides. The difference in the case of unpurified enzyme preparates may be due to the presence of *T. reesei* glucoamylase in the *T. reesei* preparate (found to be present during purification of glucoamylase P). The synergistic effect of the different starch degrading enzymes may be more pronounced in the presence of a debranching enzyme, as, for example, glucoamylase P. The specific activity of the purified recombinant glucoamylase P from *T. reesei* was slightly lower than the wild type glucoamylase P. This is because of the higher purity of the wild type enzyme. The ratio of pullulan degradation against starch degradation (as well as all other degrading ratios between the different substrates) is the same for both purified enzymes. Further work on purifying recombinant glucoamylase P from *T. reesei* has further confirmed this (Fagerstöm, R., *Enzyme and Microbiol Technology*, in press (1993)).

Example VI

Production of alcohol from the transformed yeast

Yeast strain ALKO2522 containing the integrated plasmid pALK310 and the control yeast strain YF 135 without plasmids were grown overnight in YPD medium. The cells were washed with 0.9% sodium chloride and 0.25 g of cells were inoculated in 250 ml of the following medium: 2% yeast extract, 2% peptone, 5% soluble starch (Merck). For comparison, the strain YF 135 was also fermented in the presence of 10 μl of added glucoamylase (AMG 300 L, Novo Industri A/S, Copenhagen, Denmark).

Fermentation was carried out at 30° C. in 300 ml vessels equipped with air restrictors and magnetic stirring (300 rpm). The vessels were placed on laboratory balances (Mettler) connected to a computer recording the weight loss corresponding to glucose consumption every fifteen minutes (FIG. 9). The ethanol content after 120 hours of fermentation was evaluated using gas chromatography (Hewlett Packard 5890A gas chromatograph, Porapak Q column) and the glucoamylase activity was measured from the unconcentrated medium.

The cultures of ALKO2522 contained 22.4 and 25.0 g/l ethanol and the control strain YF 135 contained 2.7 and 4.7 g/l ethanol. The control strain with added glucoamylase produced 25.7 and 25.4 g/l ethanol. The glucoamylase activities of the cultures at the end of the fermentation were: 0.8 and 0.0 U/l (YF 135), 216.6 and 246.6 U/l (YF 135+GA), 20.9 and 30.3 U/l ethanol (ALKO2522).

The results show that the production of glucoamylase by the strain ALKO2522 enabled it to convert the soluble starch into glucose and then to ferment the glucose to ethanol.

In laboratory scale experiments two different glucoamylase containing fungal growth media concentrates were compared: ALKO-GA which contains *H. resinae* glucoamylase produced by *T. reesei* ALKO 2743 and the commercial enzyme concentrate NOVO AMG 300 L (NOVO A/S, Denmark) containing *Aspergillus niger* glucoamylase. In pilot scale (100 liters) experiments only ALKO-GA was tested. The enzyme activities of both preparates are presented in Table 7. (The growth medium was five times concentrated by ultrafiltration as described in Example VIII.) The relative parts (%) of α-1,6-activity from α-1,4-activity are presented in brackets. In the third column are presented the relative activity values of different enzymes produced by *T. reesei* 2743. These values are not meant to restrict the scope of the invention. They are presented only to illustrate one embodiment of the invention as it is within the skill of the art to change the relationships of the enzyme activities produced by *T. reesei*, for example, by changing the growth conditions. For example, cellulase activities are not present when Trichoderma is grown on high levels of glucose. Increasing temperature decreases cellulase activity. Increasing pH increases xylanase activity. Decreasing temperature and pH increases cellulase activity. The activity values of NOVO AMG 300 L concentrate are each from one measurement. The activity values from *T. reesei* ALKO 2743 growth media are the mean values from 1–4 batches grown in 10 liters or 1000 liters pilot scale fermentation in the following growth media: 6% whey—complex nitrogen source-1.5% $KH_2PO_4$-0.5% $(NH_4)_2SO_4$ at pH 4.5 for 5 days at 30° C. with vigorous shaking. The Table 7 column entitled "relative activity values" refers to the relative activities of different enzymes produced by *T. reesei* 2743.

TABLE 7

|  | A. Niger concentrate NOVO 300L | T. reesei 2743 5× concentrate ALKO-GA | T. reesei 2743 relative act. values of different enzymes produced by T. reesei 2743. |
|---|---|---|---|
| 2. Tot.-prot. (mg/ml) | 220 | 59 |  |
| 1. glucoamylase |  |  |  |
| α-1,4-activity (U/ml) | 2171 | 107 | 10 |
| α-1,6-activity (U/ml) | 69 (3.2%) | 56 (52%) | 5 |
| 3. β-glucanase (U/ml) | 2167 | 35000 | 3000 |
| 4. HEC (U/ml) (mostly endoglucanase activity) | 154 | 6950 | 650 |
| 5. FPU (U/ml) (filter paper units) (mostly cellobiohydrolase activity) | 0 | 22 | 2 |
| 6. Xylanase (U/ml) | 3700 | 17800 | 1700 |
| 7. Acid protease (U/ml) | 419 | 302 | 30 |
| 8. β-Glucosidase (U/ml) | 300 | 658 | 60 |

Example VII

Use of *T. reesei* ALKO 2743 produced glucoamylase P in brewing

The aim of this study was to evaluate the effect of ALKO-GA on the recovery and characteristics of wort and beer, when the enzyme was added in mashing or fermentation. The experiments were performed both in laboratory and pilot (100 liters) scale.

β-Glucanase activity was determined using barley β-glucan as a substrate. The pH was adjusted to pH 4.8 with 0.05M Na-acetate buffer, pH 4.8. The incubation temperature was 50° C. and the incubation time was 10 minutes. HEC- and FPU activities were measured as described in "*Measurement of Cellulase Activities,*" 1984, Commission on Biotechnology, International Union of Pure and Applied Chemistry, Biochemical Engineering Research Centre, Indian Institute of Technology, Delhi, New Delhi, India 110016. Xylanase was determined according to Bailey et al.,

*J. Biotechnol.* 23:257–270 (1992). Acid protease was determined as described in *Food Chemicals Codex*, pp. 496–497 (3rd edition). β-glucosidase was determined according to Bailey, M. and K. M. H. Nevalainen, *Enzyme Microb. Technol.* 3:153–157 (1981).

The effect of ALKO-GA or NOVO AMG 300 L if added in mashing in laboratory scale: The change in characteristics of the wort was dependent on the ALKO-GA enzyme addition and the effect was dose dependent. The enzyme effect was basically the same both with ALKO-GA and NOVO AMG 300 L except the concentration of β-glucans was very low if ALKO-GA was used, but was similar to the control group if NOVO AMG 300 L was used. The low β-glucan concentration in ALKO-GA treated worts is one reason for the lower viscosity and higher filtration rate of the wort. For this reason the recovery (volume) of the wort was remarkably higher from the ALKO-GA treated mash than from the NOVO AMG 300 L treated mash.

The main reasons for this better response with ALKO-GA (even as an amount of 0.1 g/100 g mash) are the high β-glucanase, xylanase and cellulase activities in ALKO-GA produced by Trichoderma compared to the same activities in NOVO AMG 300 L produced in Aspergillus (Table 7). The extract content of the wort was similar in all experiments, but the volume of the wort was much higher when ALKO-GA was added in mashing compared to the NOVO AMG 300 L, which had no effect even when compared to the control experiment.

The apparent limit attenuation elevated from 84.7% to 89% when the ALKO-GA dose was 3 g/100 g mash and the higher dose had no more effect, although the increase of fermentable sugars (glucose, maltose and maltotriose) was correlating with the increase in enzyme dose. The result was similar, if NOVO-AMG 300 L was used during mashing. Based on this result, the ALKO-GA dose 3 g/100 g mash for pilot scale (100 liters) brewing experiment was chosen.

The effect of ALKO-GA or NOVO AMG 300 L if added in fermentation in laboratory scale: The changes in characteristics of the wort were dependent on the amount of the ALKO-GA enzyme that was added. The enzyme effects were basically the same both with ALKO-GA and NOVO AMG 300 L except that the amount of β-glucans was remarkably lower if ALKO-GA was added than if NOVO AMG 300 L was added, which, in contrast to the results in mashing experiments, lowered the β-glucan content under the control value. A small amount of the β-glucanase of NOVO AMG 300 L seems to be active at the fermentation temperature during a long fermentation period. After fermentation, the viscosity of the wort was markedly decreased with the ALKO-GA compared to NOVO AMG 300 L.

The apparent extract content was lower in enzyme-containing experiments as fermentation progressed, meaning that the yeast was able to more effectively use the energy source of the wort.

Based on the values of the apparent limit attenuation with different ALKO-GA dosages compared to the NOVO AMG 300 L value obtained by 6 g/100 liters wort, the dosage of ALKO-GA for pilot scale brewing experiment was chosen to be 60 g/100 liters wort.

The effect of ALKO-GA if added in mashing or fermentation in pilot scale (100 liters): In the pilot brewery there were two worts (100 liters each) prepared, which were used in three 50-liter fermentations as described below. In experiment 1, ALKO-GA was added in mashing, and in the control experiment, experiment 2, mashing was carried out without enzyme addition. The wort prepared with ALKO-GA in mashing (experiment 1) was fermented further without ALKO-GA addition. The wort prepared in the control mashing (experiment 2) was used in two fermentations: experiment 2A, in which ALKO-GA was added in fermentation and the control experiment, experiment 2B, in which fermentation was carried out without enzyme addition.

These tests were performed by using all-malt wort and high gravity brewing technique.

During the boiling and the clarification of the wort there were no notable differences between the test batches.

The brew-house yield was better in the ALKO-GA-mashing than in the control mashing. The addition of the ALKO-GA in mashing reduced considerably the β-glucan content and the viscosity of the wort. The apparent limit attenuation of the ALKO-GA wort was higher than of the comparison wort. The addition of ALKO-GA in mashing increased the amount of the fermentable sugars, especially the glucose content of the wort.

The β-glucan content and the viscosity of the unfiltered and filtered beer was considerably lower in the ALKO-GA beer than in the control beer. The filterability of the beers ($V_{max}$) was better if ALKO-GA was added in mashing or in fermentation compared to the control beer.

The highest alcohol content and the lowest extract content were achieved when ALKO-GA was added during the fermentation. The addition of the ALKO-GA decreased the foam stability slightly and also darkened the color. The scoring of all the beers in the taste test was 3 (good), but the ALKO-GA beers got a slightly better score than the control beer. The beers were evaluated as being a little fruity.

The use of ALKO-GA increased the formation of esters and higher alcohols during the fermentation. The highest concentrations in the beer occurred when ALKO-GA was added in mashing.

Mashing experiments in laboratory scale:

Materials and methods: The amount of ground Kustaa-malt (supplied by Lahden polttimo, Finland) used per experiment was 100 g mixed with 400 ml of water and the pH was adjusted with 1N sulfuric acid (0.6 ml). Calcium chloride was added 0.15 g.

The following enzyme dosages per experiment were used: ALKO-GA: 0, 0.1, 0.4, 1.5, 3,6 and 10 g/100 g malt; NOVO AMG 300 L: 0.35 g/100 g malt.

The control experiment without enzyme addition was also performed.

The mashing program was the following:

(1) mashing-in at +48° C., incubation for 15 minutes;
(2) increase the temperature +1° C./minute until +65° C., then incubate for 30 minutes;
(3) increase the temperature +1° C./minute until +72° C., then incubate for 30 minutes;
(4) increase the temperature +1° C./minute until +80° C., then incubate for 10 minutes;
(5) filter at +80° C.; and
(6) rinse at +80° C. two times with 100 ml water.

The saccharification during mashing at +65° C. was detected by the iodine test, (Analytica-EBC (1987) p. E 61).

After mashing the following characteristics of the wort were determined: filtration time, filtration volume, extract content, viscosity, β-glucans and apparent limit attenuation were measured according to the protocols of European Brewery Convention, Analytica-EBC (1987). The brew-house yield was calculated from the extract content and volume of the wort. The amount and profile of small molecular size carbohydrates were determined by HPLC.

Original data:

The characteristics of the wort after mashing are presented in Table 8.

Convention, Analytica-EBC (1987). The amount and profile of small molecular weight carbohydrates were evaluated by HPLC.

TABLE 8

Addition of the Enzyme Preparates (Alko-GA or Novo AMG 300L) in Mashing

| | | | | | | | | |
|---|---|---|---|---|---|---|---|---|
| Alko-GA, g | — | 0.1 | 0.4 | 1.5 | 3 | 6 | 10 | — |
| Novo AMG 300L, g | — | — | — | — | — | — | — | 0.35 |
| Saccharification, 65° C., min | 15–20 | 20–25 | 20–25 | 20–25 | 15–20 | 10–15 | 10–15 | 20–25 |
| Filtration, min/ml | 28/425 | 27/485 | 27/500 | 26/511 | 26/510 | 26/513 | 24/522 | 27/420 |
| Extract Content, % (w/w) | 12.8 | 12.6 | 12.4 | 12.6 | 12.4 | 12.7 | 12.8 | 12.9 |
| Brew-house Yield, % | 57 | 64 | 65 | 67 | 66 | 68 | 70 | 57 |
| Apparent Limit Attenuation, % | 84.7 | 84.9 | 85.5 | 87.2 | 89.2 | 89.0 | 89.0 | 89.4 |
| Viscosity, cP | 1.74 | 1.62 | 1.58 | 1.56 | 1.52 | 1.54 | 1.48 | 1.66 |
| β-Glucans, mg/l | 244 | 90 | 33 | <20 | <20 | <20 | <20 | 264 |
| Glucose, g/l | 10.5 | 12.3 | 15.5 | 26.3 | 36.8 | 58.0 | 72.9 | 53.0 |
| Maltose, g/l | 63.5 | 62.9 | 62.4 | 58.2 | 48.5 | 38.5 | 25.6 | 44.7 |
| Maltotriose, g/l | 10.9 | 10.5 | 8.6 | 4.0 | 3.5 | <1 | <1 | 0.9 |
| Panose, g/l | x) | x) | x) | 1.9 | 3.0 | 4.0 | 4.4 | x) |
| Isomaltotriose, g/l | x) | x) | x) | x) | x) | x) | x) | 1.7 |
| Fermentable Sugars, g/l | 84.9 | 85.7 | 86.5 | 88.5 | 88.8 | 97.5 | 99.5 | 98.6 | x) Not separated from maltotriose

Fermentation experiments in laboratory scale:

Materials and methods

The initial wort for fermentation experiments was prepared by the same mashing program that was used in the pilot brewery. The wort was aerated and divided to 8 fermentation vessels (2.5 liters each). The yeast strain used in fermentation was VTT-A-63015 (VTT collection of Industrial Microorganisms, Finland) and the pitching rate was 3 g centrifuged yeast/liter of wort. The fermentation temperature was +10° C.

The following enzyme dosages per experiment were used:

ALKO-GA: 0, 5, 10, 20, 40, 80 and 160 g/100 liters wort.
NOVO AMG 300 L: 6 g/100 liters wort The control experiment without enzyme addition was also performed.

The fermentation rate was followed after 6 days from the beginning of fermentation by measuring the apparent extract content. After fermentation the following quality characteristics were determined: carbohydrates, apparent attenuation, β-glucans and viscosity. All the measurements were performed according to the protocols of European Brewery The analysis results of the wort used in this experiment are presented in Table 9. The quality characteristics after fermentation are presented in Table 10.

TABLE 9

The Extract Content of the Wort Used in the Fermentation Experiment

| | | First Wort |
|---|---|---|
| Extract Yield | % (w/w) | 12.7 |
| β-Glucans | mg/l | 291 |
| Viscosity | cP | 1.89 |
| Apparent Limit Attenuation | % | 84.4 |
| Glucose | g/l | 11.2 |
| Maltose | g/l | 58.9 |
| Maltotriose | g/l | 11.5 |
| Fermentable Sugars | g/l | 81.6 |

TABLE 10

Addition of the Enzyme Preparates (Alko-GA or Novo AMG 300L) in Fermentation

| | | | | | | | | |
|---|---|---|---|---|---|---|---|---|
| Alko-GA, g | — | 5 | 10 | 20 | 40 | 80 | 160 | — |
| Novo AMG 300L, g | — | — | — | — | — | — | — | 6 |
| Extract Content, % (w/w) | | | | | | | | |
| 6 days | 2.3 | 2.2 | 2.0 | 1.8 | 1.6 | 1.4 | 1.1 | 1.4 |
| 7 days | 2.1 | 2.0 | 1.8 | 1.6 | 1.3 | 0.9 | 0.2 | 0.9 |
| 8 days | 2.2 | 2.0 | 1.8 | 1.6 | 1.3 | 0.6 | 0.1 | 0.8 |
| 9 days | 2.1 | 1.8 | 1.6 | 1.4 | 1.0 | 0.2 | 0.2 | 0.5 |
| β-Glucans, mg/l | 280 | <20 | <20 | <20 | <20 | <20 | <20 | 55 |
| Viscosity, cP | 1.71 | 1.44 | 1.42 | 1.40 | 1.37 | 1.34 | 1.33 | 1.42 |
| Apparent Attenuation, % | 83.5 | 85.8 | 87.4 | 89.0 | 92.1 | 98.4 | 101.6 | 96.1 |
| Glucose, g/l | <0.01 | 0.06 | 0.09 | 0.16 | 0.26 | 0.38 | 0.20 | 0.38 |
| Maltose, g/l | x) | x) | x) | x) | x) | x) | x) | x) |
| Isomaltose, g/l | 0.9 | 0.8 | 0.8 | 0.9 | 1.0 | 1.0 | 1.1 | 1.1 |
| Maltotriose, g/l | <0.1 | <0.1 | <0.1 | <0.1 | <0.1 | <0.1 | <0.1 | <0.1 |
| Isomaltotriose, g/l | 1.4 | xx) | xx) | xx) | xx) | xx) | xx) | xx) |
| Panose, g/l | xx) | 1.3 | 1.3 | 1.4 | 1.6 | 1.7 | 1.7 | 1.7 |
| Xylose, g/l | 0.16 | 0.16 | 0.16 | 0.17 | 0.19 | 0.22 | 0.23 | 0.17 | x) Not separated from isomaltose
xx) Isomaltotriose and panose not separated from each other Mashing and fermentation experiments in pilot scale (100 liters)

Materials and methods:

In the pilot brewery there were two worts (100 liters each) prepared, which were used in three fermentations (50 liters) as described below. In the first experiment, experiment 1, ALKO-GA was added in mashing. In the control experiment, experiment 2, mashing was carried out without enzyme addition. The wort prepared with ALKO-GA in mashing (experiment 1) was fermented further without ALKO-GA addition. The wort prepared in the control mashing (experiment 2) was used in two fermentations: experiment 2A, in which ALKO-GA was added in fermentation, and the control experiment, experiment 2B, in which fermentation was carried out without enzyme addition. These tests were performed by using all-malt wort and high gravity brewing technique. The pH in the mashing was adjusted with lactic acid and the calcium salts were added according to the conventional brewing practice. Raw materials and the process conditions were the following:

Raw materials:

Pilsen malt (2-row Kustaa-barley) (Lahden polttimo, Finland) 23 kg;

$CaCl_2 \cdot 2H_2O$ 30 g;

$CaSO_4$ 10 g;

Lactic acid (concentrated) 35 ml;

ALKO-GA 690 g (in mashing); and

Hopping: Hallertau 100 g, Saaz 70 g.

The grinding conditions were:

Steeping for the wet-milling: 30 liters water, 10 minutes at 48° C.

The mashing conditions (in 100 liters) were:

(1) mashing-in at 48° C.;

(2) maintain the mash at 48° C. for 15 minutes;

(3) increase the temperature to 65° C.;

(4) maintain the mash at 65° C. for 30 minutes;

(5) increase the temperature to 72° C.;

(6) maintain the mash at 72° C. for 30 minutes;

(7) increase the temperature to 80° C.; and (8) maintain the mash at 80° C. for 10 minutes.

The increase of the temperature was carried out at the rate of 1° C./minute.

The lautering:

After the running of the first wort, the mash cake was rinsed three times (35 liters +25 liters +5 liters). The mash cake was turned over during lautering, in the first and second rinsing water for one minute, and in the third rinsing water for 30 seconds.

Handling of the wort:

The wort was boiled for 75 minutes and hops were added. The hot wort was clarified in the whirlpool. The wort was cooled, aerated with pressure air at the rate of 2 liters/min, and pumped into fermentation tanks (50 liters). The control wort was divided into two fermentation tanks (50 liters to each). To one tank ALKO-GA was added (0.6 g/liters), and the other tank was run without enzyme addition. The amount of the yeast used was 3 g of centrifuged yeast (strain VTT-A-63015)/liter of wort.

Fermentation and the handling of the beer.

The primary and secondary fermentations were carried out at +10° C. The primary fermentation took 6 days and the secondary fermentation took 2 weeks. The normal secondary fermentation time in the pilot brewery is 3–4 weeks for the all-malt beer. The beer was filtered through EK sheets (Seitz) and the concentration of the beers was adjusted with the oxygenated and carbonated water, as the target was to get an original gravity of 10.5 per cent (weight/weight).

The analysis results of the cooled worts are presented in Table 11.

The results concerning the beer analysis are presented in Table 12.

The aroma compounds of beers are presented in Table 13.

TABLE 11

The analysis of the wort

| Sample | AMG mashing | The control mashing |
|---|---|---|
| Extract Content | 13.1 | 13.0 |
| pH | 5.3 | 5.3 |
| β-glucans mg/l | <20 | 427 |
| Apparent limit attenuation, % | 88.3 | 84.2 |
| Color, °EBC | 12 | 8.4 |
| Viscosity cP | 1.71 | 1.96 |
| Glucose, g/l | 45.2 | 12.1 |
| Maltose, g/l | 50.8 | 66.9 |
| Isomaltose, g/l | x | x |
| Maltotriose, g/l | 3.1 | 11.8 |
| Isomaltotriose, g/l | xx | xx |
| Panose, g/l | 3.1 | xxx |
| Brewhouse yield, % | 71.3% | 68.4 | x = Cannot be well separated from maltose.
xx = Cannot be well separated from panose.
xxx = A small amount can be under the peak of maltotriose.

TABLE 12

The Analyses of the Beers

| Sample | Alko-GA in mashing | Alko-GA in fermentation | The control beer |
|---|---|---|---|
| The unfiltered beer: | | | |
| Filterability, $V_{max}$, ml | 237 | 220 | 81 |
| β-glucans, mg/l | <20 | <20 | 389 |
| Viscosity, cP | 1.46 | 1.30 | 1.65 |
| The unfiltered beer: | | | |
| Original gravity, % (w/w) | 10.6 | 10.9 | 10.7 |
| Alcohol content, % (w/w) | 3.85 | 4.55 | 3.70 |
| Alcohol content, % (v/v) | 4.90 | 5.75 | 4.70 |
| Apparent extract content, % (w/w) | 1.30 | −0.05 | 1.75 |
| Real extract content, % (w/w) | 3.05 | 2.00 | 3.45 |
| Apparent attenuation, % | 88.0 | 100.5 | 83.5 |
| The real attenuation, % | 71.0 | 81.5 | 67.5 |
| Color, °EBC | 6.9 | 5.9 | 5.5 |
| pH | 4.30 | 4.35 | 4.40 |
| Foam stability | 221 | 204 | 244 |
| β-Glucans, mg/ml | 28 | <20 | 252 |
| Viscosity, cP | 1.28 | 1.15 | 1.37 |
| Glucose, g/l | ≦0.1 | 2.7 | ≦0.1 |
| Maltose, g/l | x | x | x |
| Isomaltose, g/l | 1.1 | 0.9 | 0.7 |
| Maltotriose, g/l | xx | xx | xx |
| Isomaltotriose, g/l | xx | xx | xx |
| Panose, g/l | 2.1 | 1.1 | 1.1 |
| Flavor | 3 (3.33) | 3 (3.2) | 3 (2.8) | x) The peak of isomaltose can cover maltose, especially in the sample of the Alko-GA mashing.
xx) Cannot be well separated from panose.
The scale of scoring of the flavor: 5 = excellent, 4 = very good, 3 = good, 2 = satisfactory, 1 = poor

TABLE 13

The Aroma Compounds of the Beers

| | Alko-GA added in mashing | Alko-GA added in fermentation | Control beer |
|---|---|---|---|
| Acetaldehyde, mg/ml | 2.4 | 10.3 | 3.1 |
| n-Propanol, mg/ml | 16.2 | 16.0 | 12.4 |
| Iso-butanol, mg/ml | 14.9 | 11.6 | 9.2 |
| Iso-Amylalcohol, mg/ml | 52.4 | 46.8 | 41.5 |
| Optically active amylalcohol, mg/ml | 17.6 | 15.6 | 12.6 |
| Ethylacetate, mg/ml | 30.0 | 24.0 | 15.5 |
| Isoamylacetate, mg/ml | 2.8 | 1.5 | 0.8 |
| Ethylcaproate, mg/ml | 0.2 | 0.2 | 0.2 |

Example VIII

Glucoamylase Preparation For Grain Mash Saccharification

Summary: The capacity of *Hormoconis resinae* glucoamylase P produced by a heterologous host *Trichoderma reesei* to saccharify barley grain mash was compared with that of *Aspergillus niger* glucoamylase. The results showed that incubation with preparations containing the glucoamylase P secreted by *T. reesei* produces more fermentable sugars from mash and thus makes a higher ethanol yield possible in fermentation.

Introduction

Alcoholic fermentation is one of the main industrial applications in which enzymatic starch hydrolysis is involved. In the ethanol production process, raw starch is first ground and heated. In the next stage, α-amylase is added and this liquefies and degrades starch into α-limit dextrins containing α-(1,4) and α-(1,6) glucosidic bonds. Further hydrolysis is achieved by addition of glucoamylase (1,4-α-D-glucan glucohydrolase, EC3.2.1.3.), which cleaves glucose units from nonreducing ends of α-limit dextrins formed during liquefaction. The rate of dextrin hydrolysis depends on the affinity of the glucoamylase preparation for the α-(1,6) linkages (Labout, J. J. M, St arke 37:157–161 (1985)). Most glucoamylases degrade α-(1,6) bonds inefficiently, but two glucoamylases of fungal origin, the glucoamylase P (gamP) of *Hormoconis resinae* (McCleary and Anderson, *Carbohydr. Res.* 86:77–96 (1980)) and one of the glucoamylases of *Aspergillus oryzae* (Saha et al., Stärke 31:307–314 (1979)) cleave α-(1,6) bonds easily. In other experiments, we have determined that the rate of hydrolysis of the oligosaccharides panose and $6^3$-α-D-glucosyl maltotriose by *Hormoconis resinae* gamP is only slightly lower than those of maltotriose and maltotetraose, indicating that this enzyme cleaves α-(1,6) bonds very efficiently. Based on these results, a cDNA clone described above (Vainio et al., *Curr. Genet.*, 24:38–44 (1993)) encoding the gamP protein was introduced into the cellulolytic filamentous fungus *Trichoderma reesei* under control of the Trichoderma major cellulase gene (cbh1) promoter for large scale enzyme production (Joutsjoki et al., *Curr. Genet.*, 24:223–228 (1993)). Here we report a grain mash saccharification experiment, in which the gamP secreted by *Trichoderma reesei* was compared with an *Aspergillus niger* glucoamylase (GAM), which is commonly used for grain mash saccharification in ethanol industry. The results showed that the gamP secreted by Trichoderma produces more fermentable sugars from mash and so renders higher ethanol yields possible.

Materials and Methods

Strains and Media.

*Trichoderma reesei* transformant strain ALKO2743, producing about 700 mg/l of the *Hormoconis resinae* gamP enzyme, was constructed as described above. For large scale enzyme production the Trichoderma strain was cultivated in a medium containing per liter: 60 g whey extract, 30 g complex nitrogen source derived from grain, 5 g $(NH_4)_2SO_4$, 5 g $KH_2PO_4$. The Aspergillus glucoamylase (a concentrate of an industrial-scale submerged fermentation of a selected *Aspergillus niger* strain) and the cooked and α-amylase-treated barley grain mash were obtained from the Koskenkorva ethanol factory of Alko Ltd (Ilmajoki, Finland). The glucose, maltose and maltotriose contents of the mash before and after saccharification were evaluated using liquid chromatography (Hewlett Packard 1081B liquid chromatograph). *Saccharomyces cerevisiae* strain ALKO743, used in the fermentation procedure of the saccharified grain mash, is a commercial yeast, which has formerly been used for industrial scale ethanol production. Production of the heterologous GAMP preparate.

*T. reesei* strain ALKO2743 was cultivated for 95 hours in a Bioengineering NLF 22 bioreactor (working volume 11 liters+1 liter inoculum). The temperature was adjusted to 30° C. and the pH of the culture was controlled between 4.0 and 4.8 by addition of $NH_4OH$ and $H_2SO_4$. The $pO_2$ was adjusted to >30% by agitation speed with a constant aeration rate of 12 l/min. The bioreactor inoculum was grown for three days in 3×200 ml of half-strength medium. After cultivation the growth medium in the bioreactor was spun at 5000 rpm for 20 min. The supernatant fraction was first ultrafiltered with Pellicon Cassette System (PTGC-membranes, cut-off MW10000) and then pre- (Seitz K150 board) and sterilifiltered (Seitz EK board) with a laboratory-scale plate filter to the final volume of 1.6 liters.

Determination of starch degrading activity.

Both of the glucoamylase preparates used were tested for their ability to release reducing sugar units from starch. The enzyme concentrates were diluted with 0.05M $CH_3COONa$ buffer (pH 4.8) and 1.0 ml samples of each dilution were transferred into two test tubes, which were incubated for 5 min at 60° C. One ml of 1% (w/v, in 0.05M $CH_3COONa$ buffer and preheated to 60° C.) Zulkowsky soluble starch (E. Merck, FRG) was added to one tube and incubation at 60° C. was continued for 10 min. Two ml of dinitro salicylic acid (DNS) reagent was added to both tubes and 1.0 ml of the glucoamylase preparation dilution was added to the blank tube also. After careful mixing the tubes were transferred into a boiling water bath for 5 min. Thereafter they were filled with 20 ml of deionized water, mixed well and the $OD_{540nm}$ was measured. A standard curve of known amounts of glucose was used to determine the activity values. One unit is defined as 1 μmol of reducing glucose units released in 1 min in pH 4.8.

Saccharification of grain mash and alcoholic fermentation.

For saccharification, 500 ml shake flasks equipped with air restrictors and containing 250 ml of autoclaved grain mash were supplemented with either the *Aspergillus niger* glucoamylase (GAM) or the concentrated GAMP secreted by *Trichoderma reesei*. The amount of Aspergillus-GAM added was 26 μl (22.0 U) , which means about 100 μl enzyme concentrate per 1 kg mash. This ratio has been used in industrial scale batch fermentation at the Koskenkorva ethanol factory of Alko Ltd. The amount of GAMP concentrate added was either 100% (22.0 U), 75% (16.5 U) or 50% (11.0 U), as compared with the activity on starch of the Aspergillus-glucoamylase dose. The flasks were incubated at 30° C. in moderate shaking (150 rpm) for 30 or 120 minutes. For ethanol fermentation 3 g of yeast suspended in glycerol was added to each flask. Fermentation was carried out at 30° C. with magnetic stirring (300 rpm). The flasks were placed on laboratory balances (Mettler) connected to a computer recording the weight loss corresponding to glucose consumption. The ethanol content after 70 hours of fermentation was evaluated using gas chromatography (Hewlett Packard 5890A gas chromatograph, Porapak Q column).

Results and Discussion

Fungal glucoamylases for industrial applications are usually obtained by concentrating the proteins of a growth medium, which results in an enzyme mixture of various activities. Therefore, in addition to glucoamylase, other either endo- or exo-acting hydrolases contribute to starch hydrolysis. This results in formation of glucose oligomers in addition to glucose and gives reason for the comparison of different glucoamylase preparates on the ground of their ability to produce reducing sugars from starch instead of glucose only.

For utilization of the brewer's yeast *Saccharomyces cerevisiae* starch must be hydrolyzed to at least maltotriose units. (Panchel et al., *Food Technol.* 38:99–106 (1984)). The amount of fermentable saccharides in the grain mash before and after saccharification are shown in Table 14.

TABLE 14

The glucose, maltose and maltotriose contents of grain mash before and after saccharification

| Saccharification<sup>a</sup> | | Sugars (%) | | |
|---|---|---|---|---|
| Glucoamylase added | Incubation time/min | Glucose | Maltose | Malto-triose |
| —<sup>b</sup> | — | 0.80 | 0.56 | 0.44 |
| A. niger GAM, 22.0 U | 30 | 1.3 | 0.80 | 0.54 |
| GAMP from T. reesei, 22.0 U | 30 | 1.4 | 0.73 | 0.49 |
| GAMP from T. reesei, 16.5 U | 30 | 1.1 | 0.68 | 0.40 |
| A. niger GAM, 22.0 U | 120 | 4.5 | 1.3 | 1.1 |
| GAMP from T. reesei, 22.0 U | 120 | 4.9 | 1.5 | 1.2 |
| GAMP from T. reesei, 11.0 U | 120 | 3.0 | 1.3 | 1.0 |

<sup>a</sup>See Materials and Methods
<sup>b</sup>Autoclaved, unsaccharified grain mash without glucoamylase addition The 30 min incubation time in the saccharification procedure is too short to make any significant difference between the amounts of sugars generated. During the 120 min incubation time more fermentable sugars from grain mash are produced by 22.0 U of GAMP from *Trichoderma reesei* than by an analogous amount of *Aspergillus niger* GAM. FIGS. 10 and 11 show the weight loss curves corresponding to sugar consumption during fermentation of the saccharified grain mash.

Saccharification with 22.0 U (100%) of GAMP from *T. reesei* for 30 and 120 min gives the greatest weight loss values. The weight loss from the amount of grain mash saccharified with 22.0 U of GAMP for 30 min (FIG. 10) is only slightly less than that with 120 min incubation time (FIG. 11). FIG. 10 shows also, that more weight was lost from mash saccharified with 16.5 U (75%) of GAMP than with 22.0 U (100%) of *A. niger* GAM for 30 min, even though the amount of fermentable sugars produced by the former saccharification method was smaller than by the latter (Table 14). This suggests, that the GAMP produced by *T. reesei* efficiently hydrolyzes dextrins into fermentable sugars during ethanol fermentation. The best ethanol yield was achieved with mash saccharified with 22.0 U of GAMP for 30 or 120 min (Table 14). This indicates that the additional amount of fermentable sugars utilized by yeast during fermentation (FIGS. 10 and 11) increases ethanol production. The concentrations of ethanol obtained from mash quantities saccharified with 22.0 U of GAMP for 30 or 120 min differ only slightly from each other, whereas the ethanol yield obtained from mash saccharified with 22.0 U of *A. niger* GAM is significantly lower with the 30 min than that with the 120 min incubation time. Furthermore, more ethanol was gained from mash saccharified for 30 min with 16.5 U of GAMP than for 30 min with 22.0 U of *A. niger* GAM (Table 15).

TABLE 15

Ethanol yield obtained from saccharified grain mash by yeast fermentation

| Method of saccharification<sup>a</sup> | Ethanol g/l |
|---|---|
| A. niger GAM, 22.0 U, 30 min | 69.1 |
| GAMP from T. reesei, 22.0 U, 30 min | 75.1 |
| GAMP from T. reesei, 16.5 U, 30 min | 73.2 |
| A. niger GAM, 22.0 U, 120 min | 73.3 |
| GAMP from T. reesei, 22.0 U, 120 min | 75.7 |
| GAMP from T. reesei, 11.0 U, 120 min | 71.4 |

<sup>a</sup>See Materials and Methods

These results are consistent with the weight loss values of FIGS. 10 and 11 and indicate that increased ethanol yields can be achieved with efficient dextrin hydrolysis of GAMP during ethanol fermentation.

Fungal species are a good source of glucoamylase (Manjunath et al., *J. Appl. Biochem.* 5:235–260 (1983)) and most commercially important producers belong to the *Aspergillus niger* group or are strains of Rhizopus species. However, efficient conversion of starch varieties rich in amylopectin to glucose needs a sufficient amount of α-(1,6) bonds degrading activity in addition to α-(1,4) activity. In this respect, the *Hormoconis resinae* GAMP is particularly interesting, because both of these activities are retained in the same polypeptide and no additional enzymes, e.g. pullulanase to increase the α-(1,6) activity, are needed. Furthermore, cellulosic material has been shown to prevent the efficient utilization of starch during enzymatic hydrolysis. Digestion with cellulases before the glucoamylase treatment increased the D-glucose yield from cassava starch, which contains 1–10% of attached cellulose components (Kumakura and Kaetsu, *Enzyme Microb. Technol.* 5:199–203 (1983)). *Trichoderma reesei*, which was used as host for the production of *H. resinae* GAMP, is known as an efficient secretor of cellulase enzymes (Durand, *Enzyme Microb. Technol.* 10:341–345 (1988)). The concentrated GAMP preparate produced by *T. reesei* contains various cellulolytic activities, which most likely enhance the conversion of starch attached to cellulose components to glucose in the same way as added cellulase enzymes do.

Example IX

Construction of pALK608 and its use for expression of glucoamylase P

Brief Summary: The cloning and sequencing of the glucoamylase P gene of the fungus *Hormoconis resinae* from a genomic library is described (Joutsjoki V. V. and Turkkeli T.

K., *FEMS Microbiol. Lett.* 99:237-244 (1992)), incorporated herein by reference. The gene consists of a 2153-bp protein coding region including three introns. The usual number of introns in cloned fungal glucoamylase genes has been four and in some cases five. Two of the glucoamylase P gene introns contain a sequence resembling the consensus sequence found near the 3' splice site in the introns of the fungus *Trichoderma reesei* cellobiohydrolase 1 (cbh1) gene. The *H. resinae* glucoamylase P gene, under its own promoter, was introduced into *T. reesei*, but no expression could be detected.

Materials And Methods

Microbiol strains, plasmids, phage, growth media and growth conditions

For genomic DNA isolation, *H. resinae* ATCC 20495 (American Type Culture Collection, Rockville, Md., USA) was grown for 3 days under agitation at 230 rpm at 30° C. in YPD medium (20 mg/ml proteose peptone (Difco), 10 mg/ml yeast extract, 20 mg/ml glucose).

For the gene cloning, the Stratagene (La Jolla, Calif.) λZAPII® system was used. All the materials, including the host strain *Escherichia coli* XL1-Blue and the helper phage R408 needed in the cloning procedure were purchased from Stratagene.

*E. coli* HB101 (Boyer, H. W. et al., *J. Mol. Biol.* 41:459-472 (1969)), used as a host in Trichoderma transformation vector construction, was grown in LB broth supplemented with 50-100 µg/ml ampicillin when needed. Plasmid p3SR2 (Hynes, M. J. et al., *Mol. Cell. Biol.* 3:1430-1439 (1983)) containing the acetamidase (amdS) gene, used as a selectable marker in Trichoderma transformation, was kindly donated by M. Hynes (University of Melbourne, Australia).

For enzyme production, tranformants of *T. reesei* strain ALKO2221, which is a low aspartyl protease mutant derived from the strain VTT-D-79125 (Bailey, M. J., et al., *Enzyme Microb. Technol.* 3:153-157 (1981)) by UV-mutagenesis (Arja Mäntylä, Alko Ltd.), were grown in shake flasks for 7 days at 250 rpm and 30° C. in 50 ml of two culture media, one a whey/complex nitrogen source medium with 15 mg/ml $KH_2PO_4$ and 5 mg/ml $(NH_4)_2SO_4$ (pH 5.5) and the other containing per ml: 30 mg starch, 5 mg proteose peptone (Difco), 5 mg yeast extract, 15 mg $KH_2PO_4$, 5 mg $(NH_4)_2SO_4$ (pH 5.5) supplemented with mineral salts (0.005 mg $FeSO_4.H_2O$, 0.0016 mg $MnSO_4.H_2O$, 0.0014 mg $ZnSO_4.7H_2O$, and 0.002 mg $CoCl_2$).

Genomic DNA was extracted from mycelia of Trichoderma transformants grown in shake flasks for 3 days at 250 rpm and 30° C. in 200 ml of culture medium containing per ml: 15 mg $KH_2PO_4$, 5 mg $(NH_4)_2SO_4$, 1.5 mg proteose peptone (Difco), 20 mg glucose, 0.46 mg $CaCl_2$, 0.74 mg $MgSO_4.7H_2O$ (pH 5.5), supplemented with the mineral salts mentioned above.

Total RNA was isolated from mycelia of Trichoderma transformants grown in shake flasks for 3 days at 250 rpm and 30° C. in 50 ml of whey/complex nitrogen source medium, which was heated to 110° C. for 30 min and then filtered through Whatman 3 MM paper before addition of $KH_2PO_4$ and $(NH_4)_2SO_4$.

DNA Manipulations And Sequencing

Chromosomal DNA from *H. resinae* was isolated by the method of Raeder and Broda (Reader, U. et al., *Lett. Appl. Microb.* 1:17-20 (1985)). Isolated DNA was partially digested with XhoI and fragments were size-fractionated by sucrose density gradient centrifugation in a neutral 10-40% (w/v) sucrose gradient (1M NaCl, 10 mM Tris-HCl, 1 mM EDTA, pH 8.0), which was spun in a Beckmann centrifuge (Palo Alto, Calif.) in an SW28 rotor at 25000 rpm for 20 h. The desired fragments (5-10 kb) were isolated and ligated to dephosphorylated XhoI-digested λZAPII® arms and packaged using the Stratagene packaging extracts. Bacteriophage particles were propagated in *E. coli* XL1-Blue and plated for plaque isolation. The whole glucoamylase P cDNA (EMBL database accession No. X67708; Arja Vainio et al., submitted) was used as a probe for the genomic clone. The cDNA clone was labelled with $[\alpha^{32}P]dATP$ using the Nick Translation Kit (Amersham, Bucks., UK) and the probe was used in plaque hybridization under stringent conditions (Amersham's instructions) to identify the positive clones. These were excised in vivo using R408 as helper phage and *E. coli* XL1-Blue as host. Plasmid DNA was isolated by the alkaline lysis method (Birnboim, H. C. et al., *Nucleic Acids Res.* 7:1513-1523 (1979)) and purified by centrifugation in a CsCl gradient (Garger, S. J., et al., *Biochem. Biophys. Res. Comm.* 117:835-842 (1983)).

The sequencing procedure was performed from plasmid DNA using the Sanger dideoxy chain termination method (Sanger, F. et al., *Proc. Natl. Acad. Sci. USA* 74:5463-5467 (1977)) with Sequenase® version 1.0 (United States Biochemicals, Cleveland, Ohio). Primers used in the sequencing procedure were synthesized with an Applied Biosystems (Foster City, Calif.) 381 A synthesizer.

*T. reesei* Transformation And Transformant Analysis

Standard DNA manipulations for the construction of the hybrid plasmid pALK608 (FIG. 14) were performed as described in Maniatis et al. (Maniatis, T. et al., *Molecular Cloning: A Laboratory Manual*, Cold Spring Harbor Laboratory, Cold Spring Harbor, N.Y. (1982)). The vector construction was propagated in *E. coli* host strain HB101 and isolated by the alkaline lysis method. For fungal transformation, pALK608 was purified by centrifugation in a CsCl gradient (Garger, S. J., et al., *Biochem. Biophys. Res. Comm.* 117:835-842 (1983)) and by gel chromatography in a Bio-Gel P-30 (Bio-Rad Laboratories, Richmond, Calif.) column with 10 mM Tris-HCl/1 mM EDTA (pH 8.0) as eluent. Transformation of the strain ALKO2221 was carried out according to the method of Penttilä et al. (Penttilä, M. et al., *Gene* 61:155-164 (1982)).

Total genomic DNA of the transformants obtained was isolated (Reader, U. et al., *Lett. Appl. Microb.* 1:17-20 (1985)) and the presence of the recombinant plasmid was studied by Southern blotting (Southern, E. M. *J. Mol. Biol.* 98:503-517 (1975)). In this procedure the non-radioactive DIG DNA Labelling and Detection Kit (Boehringer Mannheim, FRG) was used. Digoxigenin-labelled glucoamylase P cDNA was used as probe and after hybridization it was located with an anti-digoxigenin alkaline phosphatase conjugate. A subsequent enzyme-catalysed reaction with 5-bromo-4-chloro-3-indolyl phosphate and nitroblue tetrazolium salt produced a blue color, which visualized the hybrid molecules.

For detection of glucoamylase-specific mRNA, total RNA of the transformants was isolated (Chirgwin, J. M. et al., *Biochemistry* 18:5294-5299 (1979)) and analyzed by Northern blotting. RNA samples were denatured with formaldehyde and treated by standard methods (Maniatis, T. et al., *Molecular Cloning: A Laboratory Manual*, Cold Spring Harbor Laboratory, Cold Spring Harbor, N.Y. (1982)). Glucoamylase P cDNA labelled with $[\alpha^{32}P]dCTP$ using the Random Primed DNA Labelling Kit (Boehringer Mannheim, FRG) was used as a probe.

Hybond™-N nylon membrane (Amersham, Bucks., UK) was used in Southern and Northern blot hybridizations according to the protocols of the manufacturer.

Nine per cent sodium dodecyl sulphate polyacrylamide gel electrophoresis (SDS-PAGE) (Laemmli, U. K. *Nature* 277:680–685 (1970)) and Western blot analysis Towbin, H. et al., *Proc. Natl. Acad. Sci. USA* 76:4350–4354 (1979)) were used for the detection of glucoamylase enzyme. The blot was probed with glucoamylase-specified polyclonal rabbit anti-serum (Fagerström, R. et al., *J. Gen. Microb.* 136:913–920 (1990)) and the immunocomplexes were identified with the anti-IgG-alkaline phosphatase method (ProtoBlot®; Promega, Madison, Wis.).

Results And Discussion

In screening of the *H. resinae* genomic library by hybridizing with the glucoamylase P cDNA probe, several positive plaques were found. After in vivo excision and restriction enzyme characterizations, one plasmid containing an insert of 6.5 kb (FIG. 12) was chosen for further study. The entire structural gene (FIG. 13A, B, C) was found to consist of a 2153-bp protein coding region, which is more than the complementary cDNA. Comparison with the cDNA showed that the genomic glucoamylase P gene contains three introns. This differs from previous findings, since the other known genomic glucoamylase genes of filamentous fungi usually contain four and in some cases five introns (Nunberg, J. H., et al., *Mol. Cell. Biol.* 4:2306–2315 (1984); Hayashida, S. et al., *Agric. Biol. Chem.* 53:923–929 (1989); Boel, E. et al., *EMBO J.* 3:1581–1585 (1984); Hata, Y. et al., *Gene* 108:145–150 (1991); Shibuya, I et al., *Agric. Biol. Chem.* 54:1905–1914 (1990); Ashikari, T. et al., *Agric. Biol. Chem.* 50:957–964 (1986)). Two of the present introns are short, 53 and 73 bp, and the third, 176 bp in length, is a little longer than usual. All three introns have GT-AG boundaries (Lerner, M. R. et al., *Nature* 238:220–224 (1980)) and the shorter ones contain a consensus sequencing CTGACT near the 3' splice site. This is a part of the consensus sequence CAGCTGACTG found near the 3' splice site of *T. reesei* cbh1 gene introns (Shoemaker, S. et al., *Biotechnology* 1:691–696 (1983)). As possible transcription control regions in the glucoamylase P gene promoter there are a putative TATA box-like region (Gannon, F. et al., *Nature* 278:428–434 (1979)) at position −70 and a putative CAAT box-like region (Efstratiadis, A. et al., *Cell* 21:653–668 (1980)) at position −208 upstream from the translation initiation site. The potential eukaryotic polyadenylation signal consensus sequence AATAAA (Proudfoot, N. J. et al., *Nature* 263:211–214 (1976)) is not found, but a shortened sequence ATAAA exists 68 bp downstream from the translation termination site.

The filamentous fungus *T. reesei* is known for its ability to produce large amounts of its own secretory proteins (Montenencourt, B. S., *Trends Biotechnol.* 1:156–161 (1983)) and in this respect might serve as a useful heterologous host for glucoamylase production. From previous studies it is also known, that the amdS (acetamidase), argB (ornithine carbamoyl transferase) and gpd (glyceraldehydephosphate dehydrogenase) genes of *A. nidulans* (Penttilä, M. et al., *Gene* 61:155–164 (1982)) and the pyr4 (orotidine-5'-phosphate decarboxylase) gene of *Neurospora crassa* (Gruber, F. et al., *Curr. Genet.* 18:71–76 (1990)) are expressed in *T. reesei*. Based on these results, the hybrid plasmid pALK608 (FIG. 14) was constructed by inserting the *A. nidulans* amdS gene from plasmid p3SR2 as a selectable marker to the pBluescript vector containing the genomic glucoamylase P clone. pALK608 was introduced into the *T. reesei* strain ALKO2221 (see Materials And Methods) and some stable transformants were obtained. These were grown in media described in Materials and Methods and analysis of secreted and mycelial proteins was performed by Western blotting. Heterologous glucoamylase enzyme was not found in the transformants but the isolated *H. resinae* glucoamylase P protein used as a positive control was clearly visualized (data not shown). Northern hybridization showed a similar result: no glucoamylase P-specific mRNA could be seen (data not shown).

Southern blot analysis of one transformant strain showed the presence of the glucoamylase P gene in the strain. The blot was probed with glucoamylase P cDNA, which does not hybridize with sequences in the untransformed strain. There is one NotI site in pALK608 and plasmid sequences in the transformant are carried on a NotI fragment of different size (smaller) than linearized pALK608. This suggests that the transforming plasmid DNA is integrated into the genomic DNA of *T. reesei*. SalI-SphI digestion releases the whole glucoamylase P protein coding sequence from plasmid pALK608. The corresponding fragment is present in the SalI-SphI-digested DNA of the transformant strain but not in the untransformed parental strain. These results suggest that the glucoamylase P gene integrated into the genome of the *T. reesei* transformants is either not transcribed or the level of transcription is so low that it cannot be detected by the methods used.

For large scale enzyme production the usual way is to over-express the gene for the desired enzyme in its own host. In some cases the original host cannot be used in industrial applications because of difficulties in cultivation, slow growth or a too low protein secretion capacity, as in the case with *H. resinae*. In this situation a host strain having more suitable industrial characteristics would be a better choice. Transcription control elements of *T. reesei* obviously differ so much from those of *H. resinae*, that successful expression of glucoamylase P gene under the control of its own promoter is not possible in Trichoderma.

The ability of *T. reesei* to produce glucoamylase from a cDNA construct that is operably linked to *T. reesei* transcriptional expression signals is described above. The experiment below describes the surprising enhancement of glucoamylase P expression that was found when the glucoamylase P gene sequences (exons and introns) were operably linked to *T. reesei* expression signals, an enhancement even over that of the cDNA construct.

Example X

Construction of pALK612 and its use for expression of glucoamylase P

A construct was prepared, pALK612(FIGS. 15 and 16), in which the glucoamylase P is synthesized from the *H. resinae* gene in Trichoderma, using the native glucoamylase P secretion signal and operably linking expression to the cbh1 expression cassette. As shown below, the growth medium of the Trichoderma that were transformed with this construct contained three to eight times more glucoamylase P (up to 50 U/ml) than the growth medium of a Trichoderma transformed with the previously best cDNA construct, ALKO2743.

Figure 14:
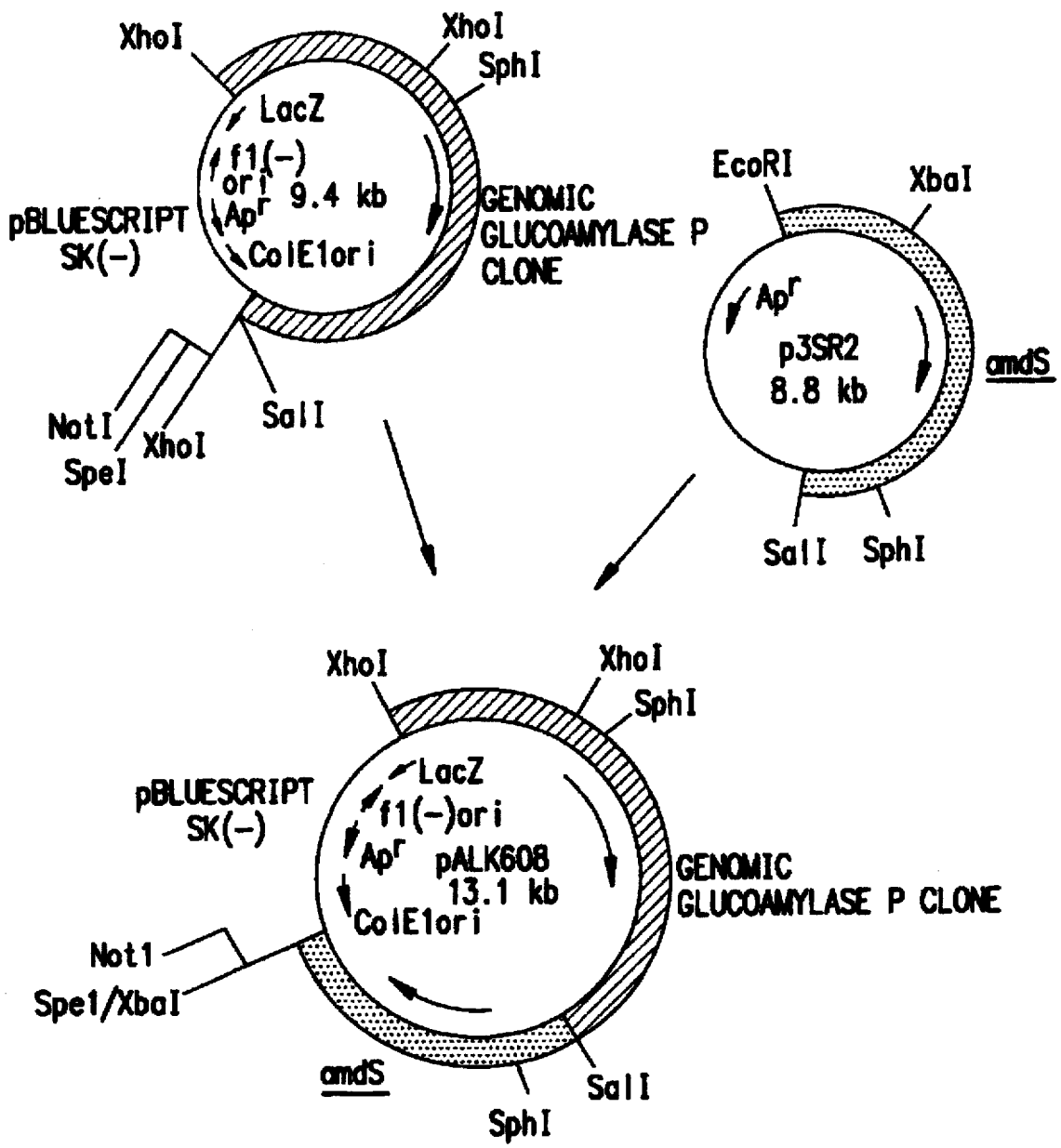
FIG. 14 shows the construction of hybrid plasmid pALK608. The small SpeI-SalI-limited fragment in the pBluescript vector containing the genomic glucoamylase P clone was replaced by the 3.8-kb XbaI-SalI fragment from plasmid p3SR2 containing the amdS gene. SpeI and XbaI restriction ends are compatible and can be joined together.
Figure 15:
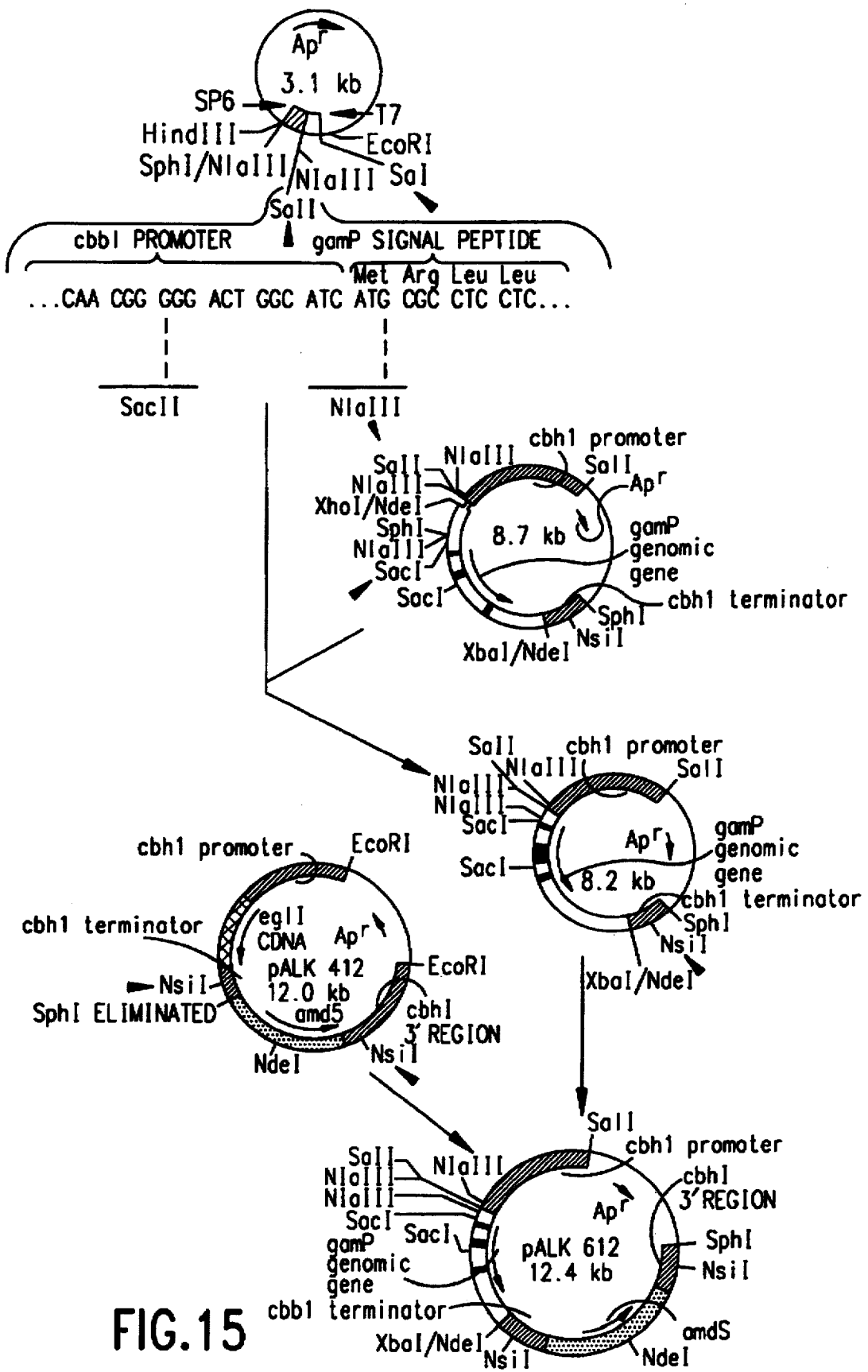
FIG. 15 shows the construction of plasmid pALK612.
Figure 16:
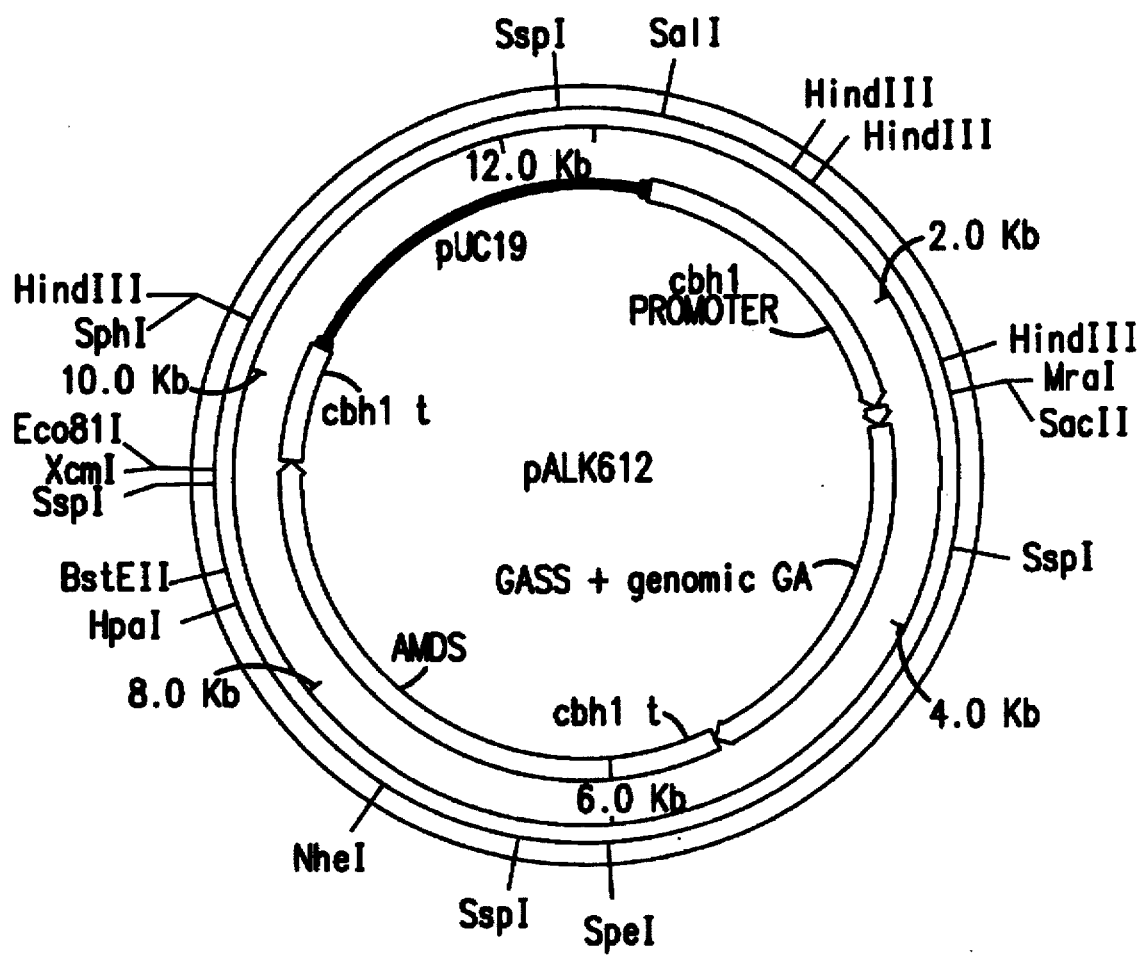
FIG. 16 is a more detailed, scaled map of plasmid pALK612.

Hybrid plasmid pALK612 was constructed by using standard DNA methods as described (Maniatis et al., *Molecular cloning: A Laboratory Manual*, Cold Spring Harbor Laboratory, Cold Spring Harbor, N.Y. 1982) (FIGS. 14 and 15). In this plasmid vector the cbh1 gene promoter is fused precisely to the protein coding region of the gamP genomic gene. The 8.7 kb plasmid was obtained by inserting the 3.1 kb XhoI-XbaI fragment containing the genomic gamP gene coding region from plasmid pALK608 (Example IX and Joutsjoki, V. V. and Torkkeli, T. K., *FEMS Microbiol. Lett.* 99:237–244 (1992)) into the NdeI site of the cbh1 expression cassette in pAMH110 (Nevalainen et al., in Leong and Berka (eds.), *Molecular Industrial Mycology*, Marcel Dekker Inc., N.Y. (1991), pp. 129–148; see also U.S. patent application Ser. No. 07/496,155) after digestion of the cohesive restriction ends with mung-bean nuclease. The precise assembly of the cbh1 promoter and the gamP protein coding region was achieved by using pGEM3 (Promega, Madison, Wis., USA) as an auxiliary vector. The 93 bp NlaIII-SacI fragment, which contains the entire gamP gene signal sequence, was isolated from the genomic gamP gene in pALK608 by phenol extraction from a 3.8% LMP-agarose gel (FMC BioProducts, Rockland, Me., USA) and ligated to the SacI and SphI sites in pGEM3. NlaIII and SphI restriction ends are compatible and can be joined together. Both the NlaIII and SphI restriction sites were reformed in this ligation and so enabled the ligation of the 98 bp NlaIII fragment, which precedes the translation start ATG codon in the cbh1 promoter region and was isolated from pAMH110 as described above, in the vector. The cbh1 promoter and the gamP signal sequence fusion was released from the 3.1 kb plasmid with SacII and SacI digestions and inserted into the place of the SacII-SacI fragments denoted in the 8.7 kb plasmid. This resulted in an 8.2 kb plasmid, in which the fidelity of the construction was checked by sequencing with the Applied Biosystems 373A DNA Sequencer. For successful replacement of the cbh1 locus in the host strain the 5' and 3' cbh1 flanking regions in the replacing fragment should be at least 1 kb in size (Suominen et al., *Mol. Gen. Genetics* (1993), in press). Therefore, the amdS gene (used as a selection marker for the transformants) containing the NsiI fragment in the 8.2 kb plasmid was replaced with the corresponding fragment from plasmid pALK412 (Karhunen et al., *Mol. Gen. Genetics* (1993), in press) after elimination of the SphI site in pALK412 by mung-bean nuclease treatment of the cohesive restriction ends before relegation. The cbh1 3' region in pALK412 contains a small region of cbh1 coding sequence beside the amdS gene, and this increases the size of the flanking cbh1 terminator region in plasmid pALK612 to about 1 kb. The cbh1 gene replacing fragment in pALK612 can be released from the *Escherichia coli* vector sequences with SalI and SphI digestions.

*Trichoderma reesei* ALKO2221 was transformed with the linear SphI-SalI fragment from pALK612. Transformation was performed as described previously. About 250 transformants were screened by cultivating them first in shaker flasks and measuring the 1,6-glycosidic bond hydrolyzing activity as described earlier. The best transformants were about three times more active compared with the former best strain of *T. reesei*, ALKO2743. When these best transformants were cultivated in one liter fermentors, they were about five times more active compared with the former best strain ALKO2743. In cultivations in ten liter fermentors, the best transformants were six to eight times better than the former best strain ALKO2743, the glucoamylase activity being about 50 U/ml.

Thus, surprisingly, the *H. resinae* genomic clone, which retained the native *H. resinae* glucoamylase P introns and peptide secretion signal sequence but which was operably linked to *T. reesei* expression signals, specifically the cbh1 expression signals, was a significantly better construct for glucoamylase P production in *T. reesei* than was the cDNA transcript use in ALKO2743.

Example XI

Secretion of the Hormoconis resinae glucoamylase P enzyme from Trichoderma reesei directed by the natural and the cbh1 gene secretion signal Secretion of the *Hormoconis resinae* glucoamylase P (GAMP) enzyme from *Trichoderma reesei* using either the natural N-terminal extension of the premature glucoamylase P or the cellobiohydrolase 1 (CHBI) signal peptide was examined. The expression conditions for the heterologous glucoamylase P (gamP) gene in *T. reesei* were standardized by targeting one copy of a plasmid fragment, containing the gamP gene, to the cbh1 locus of the host. The results below show that the transient N-terminal extension of the premature GAMP acts as an efficient secretion signal in *T. reesei* and leads to a higher yield of extracellular glucoamylase activity than does the signal peptide of CHBI.

The export of most secretory proteins across the cytoplasmic membrane in procaryotes and the endoplasmic reticulum (ER) in eukaryotes is mediated by a transient N-terminal signal sequence. In spite of the high degree of sequence variability, three structurally distinct regions have been identified in signal sequences: a basic N-terminal region, a central hydrophobic region and a more polar C-terminal region (von Heijne, G., *J. Mol. Biol.* 184:99–105 (1985)). The amino acids in the immediate proximity of the cleavage site have an essential role in removal of the signal sequence to form the mature protein (von Heijne, G., *Eur. J. Biochem.* 133:17–21 (1983); von Heijne, G., *Nucl. Acids Res.* 14:4683–4690 (1986)). Many features of the protein translocation process seem to be shared by all species, since most exported proteins can be secreted and processed correctly by the export machinery from several organisms (Gierasch, L. M., *Biochemistry* 28:923–930 (1989)).

Heterologous and synthetic signal sequences have been used in elucidating the mechanism of protein secretion. The secretion of human lysozyme by *Saccharomyces cerevisiae* has been altered by engineering the hydrophobic segment of the signal sequence (Yamamoto et al., *Biochem. Biophys. Res. Comm.* 149:431–436 (1987); Yamamoto and Kikuchi, *Eur. J. Biochem* 184:233–236 (1989)), which thus appears to have an important role in protein translocation. Various signal peptide constructions have also been tested in the filamentous fungal species *Aspergillus nidulans* (Cullen et al., *Bio/Technology* 5:369–376 (1987); Gwynne et al., *Bio/Technology* 5:713–719 (1987)) and *Trichoderma reesei* (Harkki et al., *Bio/Technology* 7:596–603 (1989)).

The soft rot fungus *Trichoderma reesei* is an efficient producer of cellulolytic enzymes (Durand et al., *Enzyme Microb. Technol.* 10:341–345 (1988)), of which cellobiohydrolase I (CBHI) forms the major part (Grizali and Brown, *Adv. Chem. Ser.* 81:237–260 (1979)). The promoter of the cellobiohydrolase 1 (cbh1) gene (Shoemaker et al., *Bio-Technology* 1:691–696 (1983); Teeri et al., *Bio/Technology* 1:696–699 (1983)) has proven to be effective for directing the expression of the *Hormoconis reesinae* glucoamylase P (gamP) (Vainio et al., *Curr. Genet.*, 24:38–44 (1993); Joutsjoki and Torkkeli, *FEMS Microbiol. Lett.* 99:237–244 (1992)) gene in *T. reesei* (Joutsjoki et al., *Curr. Genet.*, 24:223–228 (1993)). The nascent CBHI enzyme contains a 17 amino acid signal peptide (Shoemaker et al., op. cit.), whereas the nascent glucoamylase P (GAMP) protein has a 29 amino acid N-terminal extension, which does not occur in the mature protein and may contain a proteolytically processable part in addition to a signal sequence (Vainio et al., *Curr. Genet.*, 24:38–44 (1993)).

The potential effect of the N-terminal extension of the secretion of the heterologous GAMP from *T. reesei* was examined. This example shows the modification of a one-step gene replacement vector, which contained the genomic gamP gene under the cbh1 gene promoter. The sequence coding for the GAMP N-terminal extension and the first amino acid of the mature protein was replaced with the sequence coding for the CBH1 signal peptide and the first amino acid of mature CBH1. The first amino acid of the mature protein was included into the replaced region, because it is close to the final peptide-protease complex (von Heijne, G., *Eur. J. Biochem.* 133:17–21 (1983))during the cleavage procedure. We describe GAMP production by two *T. reesei* transformant strains, in which the cbh1 gene was replaced with one copy of the gamP gene containing either the natural N-terminal extension or the cbh1 gene signal sequence.

Materials and Methods

Abbreviations: E, EcoRI; H, HindIII; Nd, NdeI; Nl, NlaIII; Ns, NsiI; S, SalI; Sal, SacI; SalI, SacII; Sp, SphI; Xb, XbaI; Xh, XhoI; SphI eliminated; p, promoter; t, terminator.

Strains and Media

*Escherichia coli* strain HB101 (Boyer & Roulland-Dussoix, *J. Mol. Biol.* 41:459–472 (1969)) was used as a host in the construction of the hybrid plasmid pALK613. The host and its transformants were grown in LB broth supplemented with 50–100 µg/ml ampicillin when needed. *Trichoderma reesei* strain ALKO2221, which is a low aspartyl protease mutant derived from the strain VTT-D-79125 (Bailey & Nevalainen, *Enzyme Microb. Technol.* 3:153–157 (1981)) by UV-mutagenesis (Aria Mäntylä, Alto Ltd.), was used as a recipient for the vector fragment containing the gamP gene. It was maintained on PD agar (Potato Dextrose broth [Difco]) slants and plates. For enzyme production, Trichoderma transformants were grown in shake flasks for seven days at 250 rpm and 30° C. in 50 or 250 ml of a culture medium that induces cellulase production and contains per ml: 40 mg whey extract/15 mg complex nitrogen source derived from grain/15 mg $KH_2PO_4$/5 mg $(NH_4)_2SO_4$ (pH 5.5). Glucoamylase activity was determined after seven days' cultivation of the 50 ml cultures and in daily samples of the 250 ml cultures. Genomic DNA was isolated from mycelia of Trichoderma transformants grown in shake flasks for three days at 250 rpm and 30° C. in 100 ml of culture medium containing per ml: 1.5 mg proteose peptone (Difco) /20 mg glucose/15 mg $KH_2PO_4$/5 mg $(NH_4)_2SO_4$/0.46 mg $CaCl_2$10.74 mg $MgSO_4.7H_2O$ (pH 5.5) supplemented with mineral salts (0.005 mg $FeSO_4.H_2O$/0.0016 mg $MnSO_4.H_2O$/0.0014 mg $ZnSO_4.7H_2O$/0.002 mg $CoCl_2$).

Plasmid Construction

Figure 17:
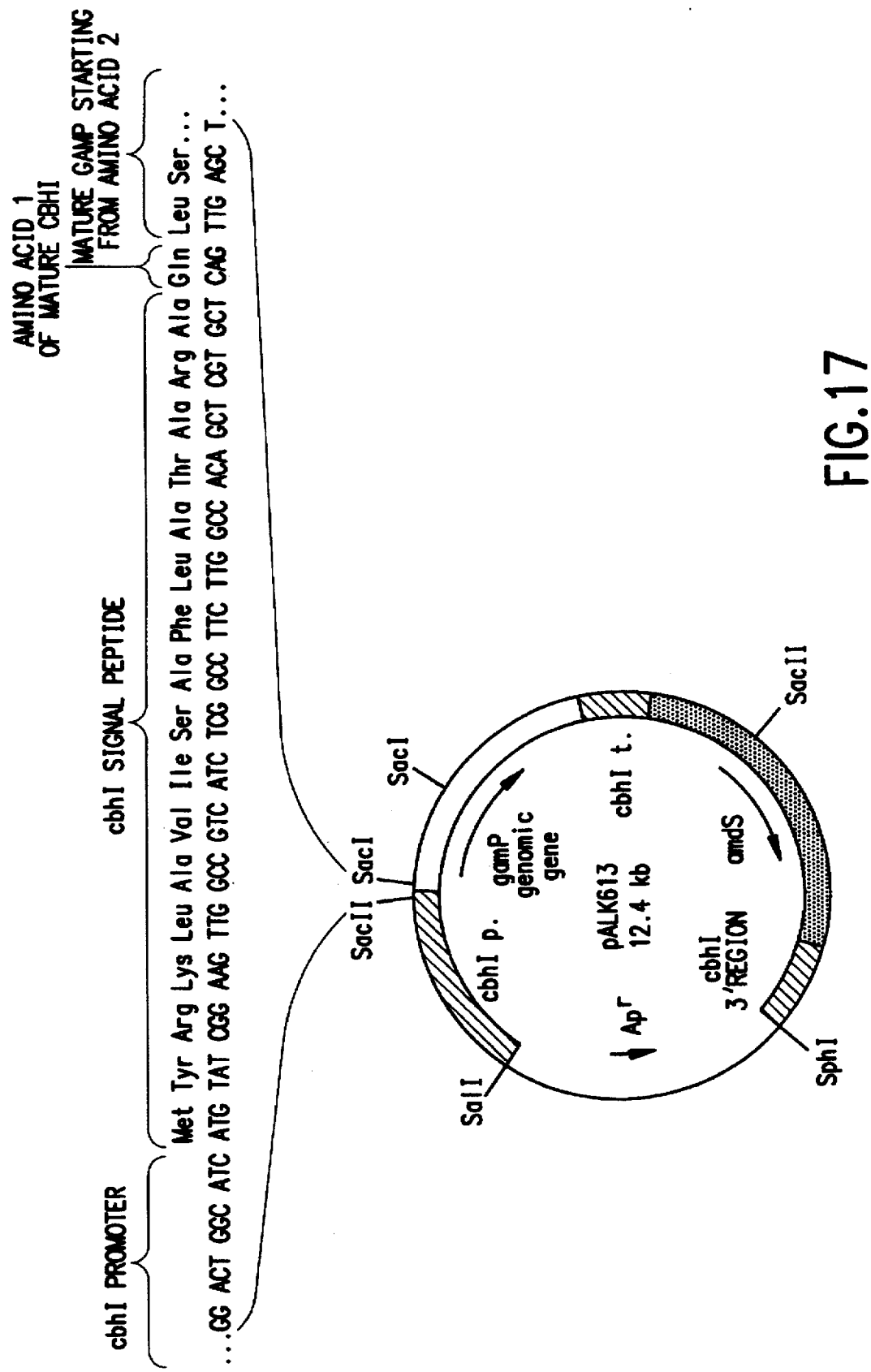
FIG. 17 is a construction of the one-step cbh1 gene replacement vector pALK613. For construction of the hybrid plasmid pALK613, the 107 bp SacII-SacI fragment in plasmid pALK612 was replaced with the following linker (FIG. 17, SEQ ID No. 5 and Seq ID No. 6; for details see Materials and methods)

The hybrid plasmid pALK613 (FIG. 17) was constructed by modifying the plasmid pALK612 in which the genomic gamP gene is under the control of the cbh1 gene promoter and terminator regions, and the *Aspergillus nidulans* acetamidase (amdS) gene is included as a selectable marked for Trichoderma transformants. For construction of the plasmid pALK613, the 107 bp SacII-SacI fragment of pALK612, containing the sequence coding for the N-terminal extension of the premature GAMP and the first amino acid of the mature enzyme, was replaced with a synthetic linker with SacII and SacI cohesive ends and the sequence coding for the cbh1 gene signal sequence and the first amino acid of mature CBHI. For construction of the linker, 70-mer and 72-mer oligonucleotides were synthesized with an Applied Biosystems (Foster City, Calif.) 381A Synthesizer. For purification from undersized fragments, the oligos were run on an 8M urea/10% polyacrylamide gel and the desired band was cut out and ground in an Eppendorf tube with a glass rod. The tube was filled with 10 mM Tris.HCl/1 mM EDTA (pH 8.0) and incubated at 37° C. overnight. After incubation, the contents of the Eppendorf tube were passed through a Bio-Gel P-30 (Bio-Rad Laboratories, Richmond, Calif.) column with 10 mM Tris.HCl/1 mM EDTA as eluent. The oligos were annealed in 0.2M NaCl/10 mM Tris.HCl (pH 7.8)/1 mM EDTA, which was heated to 65° C. for 30 min., then adjusted to 57° C. for 2 h and left to cool slowly to 30° C. Finally, the tube was chilled on an ice slurry for one hour. Phosphorylation of the constructed linker and dephosphorylation of the vector fragment before ligation were done as described (Maniatis et al., *Molecular Cloning: A Laboratory Manual*, Cold Spring Harbor Laboratory, N.Y., p. 545 (1982)) and the ligation mixture was used to transform *E. coli* HB101 (Mandel and Higa, *J. Mol. Biol.* 53:159–162 (1970)). The accuracy of the modified region in pALK613 was verified by sequencing with the Applied Biosystems 373A DNA Sequencer.

*Trichoderma reesei* Transformation and Transformant Analysis

The hybrid plasmid pALK613 was propagated in *E. coli* host strain HB101 and isolated by the alkaline lysis method (Birnboim and Doly, *Nucl. Acids Res.* 7:1513–1523 (1979)). For Trichoderma transformation, the plasmid was digested with SalI and SphI and run on a 0.6% LMP-agarose gel (FMC Bioproducts, Rockland, Me.). The fragment containing the gamP gene was isolated by phenol extraction and purified with an anion-exchange resin-containing Qiagen-tip 20 column (Qiagen Inc., Chatworth, Calif.). Transformation of *Trichoderma reesei* ALKO2221 was performed as described (Penttilä et al., *Gene* 61:155–164 (1987)) and transformants were selected by their ability to grow on acetamide because of the amdS gene. Well growing and sporulating transformants were purified through single spores on Trichoderma minimal plates containing 10 mM acetamide, 0.1% Triton X-100 and 15 mM CsCl and grown in a 96-well Millititer Filtration Plates (Millipore Corporation, Bedford, Mass.) at 30° C. for seven days. After cultivation, the filtered cultures were transferred onto a nitrocellulose filter (Amersham, Buckinghamshire, UK) with a Minifold I SRC 96 Dot Blotter (Schleicher & Schuell, Dassel, FRG). For detection of the CBHI enzyme, the filter was analyzed with CBHI-specific monoclonal antibody CI-89 (Aho et al., *Eur. J. Biochem.* 200:643–649 (1991)). The immunocomplexes were identified with the anti-IgG-alkaline phosphatase method (ProtoBlot®; Promega, Madison, Wis.). For Southern blot hybridizations, total genomic DNA of *Trichoderma reesei* was isolated by the method of Raeder and Broda (Raeder and Broda, *Lett. Appl. Microb.* 1:17–20 (1985)). After digestion with restriction enzyme, the genomic DNA was transferred (Southern, E. M., *J. Mol. Biol.* 98:913–920 (1990)) onto Amersham's Hybond™-nylon membrane, which was then hybridized with a digoxigenin-labelled probe (the DIG DNA Labelling and Detection Kit; Boehringer Mannhein, FRG) according to the protocols of the manufacturer.

Glucoamylase Activity Tests

Secreted glucoamylase activity was determined in the supernatants of *T. reesei* growth medium samples centrifuged for 5 min at 4000× g, with either Zulkowsky soluble starch (E. Merck, FRG) as substrate for the α-1,4 glucosidic activity or pullulan (sigma Chemical Company Ltd., St. Louis, Mo.) for the α-1,6 activity as described (Fagerström et al., *J. Gen. Microb.* 136:913–920 (1990)). The Glucose Mercotest Kit 14335 (Diagnostica Merck, FRG) was used to measure the D-glucose generated. One enzyme unit (U) releases 1 µmol of glucose in one min at 30° C.

Results and Discussion

Targeted recombination of incoming DNA makes it possible to introduce precise changes without affecting any other sites in the genome of the host. In the hybrid pALK613 (FIG. 17), the 9.7 kb SalI-SphI fragment, containing the gamP gene is flanked by the cbh1 gene promoter and 3' region, which act as recombination homologies to the resident cbh1 gene in the host. The linear SalI-SphI fragment of pALK613 was used to transform the *T. reesei* strain ALKO2221, and screening of the transformants for those not secreting CBHI protein was performed with dot blotting and a subsequent analysis with CBHI specific monoclonal antibody as described in Material and methods. As described earlier, Trichoderma transformant strain named ALKO3435 was constructed, in which the cbh1 gene was replaced by one copy of the 9.7 kb SalI-SphI fragment from plasmid pALK612. This fragment contains the genomic gamP gene with the natural N-terminal protein coding region fused directly to the last nucleotide of the cbh1 gene promoter, but is otherwise similar to the pALK613 fragment.

From the CBHI negative transformants obtained with the pALK613 fragment, a single-copy replacement strain was chosen and named ALKO3435a. The genome structure of ALKO3435a was confirmed with Southern blotting by comparing it with the known structure of the ALKO3435 genome. FIG. 18 is a hybridization blot of total DNA from the transformant strains ALKO3435 and ALKO3435a and the untransformed host ALKO2221 digested with the restriction enzyme XhoI and hybridized with a probe specific to the cbh1 gene promoter and terminator sequences. XhoI digestion releases the *T. reesei* genomic cbh1 gene with its promoter and terminator sequences as an 8.5 kb fragment (lane 1). Since XhoI does not cut the pALK612 and pALK613 fragments, the replacement of replacement of the resident cbh1 gene the host with a 9.7 kb plasmid fragment causes the size of the fragment to increase to 13.5 kb. This band can be identified in the genome of the transformant strains ALKO3435 (lane 2) and ALKO3435a (lane 3) with the probe used. FIG. 18a shows a hybridization blot of total DNA from the transformants ALKO3435 and 3435a and the host ALKO2221 digested with restriction enzyme SacII and hybridized with gamP. SacII digestion releases a 4 kb fragment, containing the gamP gene, from the pALK612 plasmid fragment in ALKO3435 (lane 2) and from the pALK613 plasmid fragment in ALKO3435a (lane 3), which can be detected with the gamP probe. The probe does not identify the sequences of the host strain ALKO2221 (lane 1). Thus, as in ALKO3435, so in ALKO3435a, the resident cbh1 gene has been replaced by one copy of the plasmid fragment (FIGS. 19 and 19a). Therefore, potential disparities caused by different copy numbers and different locations in the host genome on the expression of the heterologous gamP gene in *T. reesei* are eliminated. The secreted glucoamylase activities determined from the 50 ml shake flask culture fluids after seven days' cultivation (see Materials and methods) of *T. reesei* transformant strains AKO3435 and ALKO3435a are shown in Table 16.

TABLE 16

| Strain | cbh1 locus | Glucoamylase activity[a,b] | |
|---|---|---|---|
| | | U/l (starch) | U/l (pullulan) |
| ALKO3435 | Replaced by one copy of pALK612 fragment | 9560 | 5950 |
| ALKO3435a | Replaced by one copy of pALK613 fragment | 7720 | 4860 |

[a]For glucoamylase activity determinations see Materials and methods.
[b]Each activity value is the mean of three independent cultivations.

Because of the natural glucoamylase of *T. reesei* (Prentice, N., *Cereal. Chem.* 59:231-323 (1982)), the background α-1,4 and α-1,6 glucosidic activities produced by the host strain ALKO2221 in these culture conditions are about 1500 and 500 U/l, respectively (Fagerström et al., *J. Gen. Microb.* 136:913-920 (1990)). The secreted α-1,4 and α-1,6 activities of ALKO3435 are higher than those of ALKO3435a. Assuming that the specific activities have remained the same, this indicates that the amount of secreted GAMP is higher with the natural N-terminal extension, than with the cbh1 signal sequence. The same thing can be seen from the glucoamylase activity curves determined from the samples of the 250 ml cultivations in FIG. 20. The final α-1,4 activities produced by ALKO3435 and ALKO3435a are somewhat higher in the 250 ml than in the 50 ml cultures, but the difference between the strains is about the same in both cultivation volumes.

Heterologous expression of calf chymosin with various secretory control modifications has been performed in *Aspergillus nidulans* (Cullen et al., *Bio/Technology* 5:369-376 (1987)) and *Trichoderma reesei* (Harkki et al., *Bio/Technology* 7:596-603 (1989)). In addition to the *T. reesei* CBHI and *Aspergillus niger* glucoamylase signal peptides, the propeptide region of the *A. niger* glucoamylase and sequences derived from the mature proteins of CBHI and glucoamylase also had their effect on the secretion of active calf chymosin. In the present work, a higher yield of the *Hormoconis resinae* GAMP from *T. reesei* was obtained with its natural transient N-terminal secretion signal peptide than with the CBHI signal peptide and the first amino acid of mature CBHI, when the copy number and location of the natural and the modified gamP gene in the host genome were compatible. This shows that the transient N-terminal extension of the gamP gene, in spite of its difference from the cbh1 gene signal sequence, is not a rate-limiting factor in the production of the heterologous GAMP from *T. reesei*. As in the homologous host *Hormoconis resinae*, the transient N-terminal peptide in GAMP is cleaved after Arg-1 in *T. reesei*. The efficient processing of premature GAMP may be utilizing the same processing system responsible for cleaving CBHII preprotein after Arg-1 in *T. reesei*. (Teeri et al., *Gene* 51:43-52 (1987)). Therefore, instead of only peptide regions directing the translocation procedure, the entire structure of the exported proteins may have an important role in the level of secretion in filamentous fungi. This is supported by protein fusion experiments, in which the enhanced production of a heterologous protein was achieved by fusing the sequence coding for the heterologous polypeptide in frame to the highly expressed Aspergillus glucoamylase gene (Ward et al., *Bio/Technology.* 8:435-440 (1990); Contreras et al., *Bio/Technology* 9:378-381 (1991); Roberts et al., *Gene* 122:155-161 (1992)).

All references referred to are incorporated herein by reference. Now having fully described the invention, it is considered that the invention and many of its attendant advantages will be understood from the foregoing description and that it will be apparent that various changes may be made in the steps of the described methods without departing from the spirit and scope of the invention or sacrificing all of its material advantages.

What is claimed is:

1. A composition comprising purified DNA molecules that have a nucleotide sequence capable of being processed by a Trichoderma host cell to encode a protein, said protein comprising an amino acid sequence selected from the group consisting of:

a. amino acids 1-616 as shown in SEQ ID NO. 2 (FIG. 5A) or in SEQ ID NO. 4 (FIG. 13); and b. amino acids 30-616 as shown in SEQ ID NO. 2 (FIG. 5A) or in SEQ ID NO. 4 (FIG. 13);

said DNA molecules also having the sequence of introns IVS1, IVS2 and IVS3 as shown in SEQ ID NO. 4 (FIG. 13), said introns being inserted between exons encoding said amino acids as shown in SEQ ID NO. 4 (FIG. 13).

2. The composition of claim 1, wherein said nucleotide sequence of the DNA encoding said protein comprises the protein encoding sequence of SEQ ID NO. 1 (FIG. 5) or SEQ ID NO. 4 (FIG. 13).

3. A recombinant vector comprising a DNA sequence that is capable of being processed by a Trichoderma host cell to encode a protein, said protein comprising an amino acid sequence selected from the group consisting of:

a. amino acids 1-616 as shown in SEQ ID NO. 2 (FIG. 5A) or in SEQ ID NO. 4 (FIG. 13); and b. amino acids 30-616 as shown in SEQ ID NO. 2 (FIG. 5A) or in SEQ ID NO. 4 (FIG. 13);

said DNA sequence also having the sequence of introns IVS1, IVS2 and IVS3 as shown in SEQ ID NO. 4 (FIG. 13), said introns being inserted between exons encoding said amino acids as shown in SEQ ID. NO. 4 (FIG. 13 ).

4. The vector of claim 3, wherein said DNA sequence of the sequence encoding said protein comprises the protein encoding sequence of SEQ ID. NO. 1 (FIG. 5) or SEQ ID NO. 4 (FIG. 13).

5. A Trichoderma host cell transformed with a DNA molecule having a nucleotide sequence that is capable of being processed by said Trichoderma host cell to encode a protein, said protein comprising an amino acid sequence selected from the group consisting of:

a. amino acids 1-616 as shown in SEQ ID NO. 2 (FIG. 5A) or in SEQ ID NO. 4 (FIG. 13); and b. amino acids 30-616 as shown in SEQ ID NO. 2 (FIG. 5A) or in SEQ ID NO. 4 (FIG. 13);

said DNA molecule also having the sequence of introns IVS1, IVS2 and IVS3 as shown in SEQ ID NO. 4 (FIG. 13), said introns being inserted between exons encoding said amino acids as shown in SEQ ID NO. 4 (FIG. 13).

6. The host cell of claim 5, wherein said DNA sequence of the sequence encoding said protein comprises the protein encoding sequence of SEQ ID NO. 1 (FIG. 5) of SEQ ID NO. 4 (FIG. 13).

7. The host cell of claim 5 or claim 6, wherein said host cell is *Trichoderma reesei*.

8. The host cell of claim 5 or claim 6, wherein said DNA sequence contains the native *H. resinae* glucoamylase P introns and secretion signal.

9. The host cell of claim 8, wherein said Trichoderma strain is *T. reesei*.

10. The host cell of claim 5, or claim 6, wherein said DNA encodes a protein that comprises amino acids 30-616 as shown in SEQ ID NO. 2 (FIG. 5A) or SEQ ID NO. 4 (FIG. 13).

11. The host cell of claim 10, wherein said Trichoderma strain is *T. reesei*.

12. The host cell of claim 10, wherein the sequence of said DNA encoding said amino acids is that shown in SEQ ID NO. 1 (FIG. 5) or in SEQ ID NO. 4 (FIG. 13).

13. The host cell of claim 12, wherein said Trichoderma strain is *T. reesei*.

14. The host cell of claim 5 or claim 6, wherein said DNA molecule comprises the promoter and terminator regions of a gene from Trichoderma operably linked to said nucleotide sequence.

15. The host cell of claim 14, wherein said Trichoderma strain is *T. reesei*.

16. The host cell of claim 14, wherein said promoter or said terminator are from the cbh1 gene.

17. The host cell of claim 16, wherein said Trichoderma strain is *T. reesei*.

18. The host cell of claim 5 or claim 6, wherein said DNA molecule is selected from the group consisting of pALK602 and pALK612.

19. The host cell of claim 18, wherein said Trichoderma strain is *T. reesei*.

20. The host cell of claim 5 or claim 6, wherein said glucoamylase P sequence is integrated into the chromosome of said Trichoderma.

21. The host cell of claim 20, wherein said Trichoderma strain is *T. reesei*.

22. A Trichoderma host cell transformed with DNA encoding amino acids 1-29 of SEQ ID NO. 1 (FIG. 5) or in SEQ ID NO. 4 (FIG. 13).

23. The Trichoderma host cell of claim 22, wherein said DNA further comprises DNA encoding, or capable of being processed to encode, amino acids 30-616 as shown in SEQ ID NO. 2 (FIG. 5A) or as shown in SEQ ID NO. 4 (FIG. 13), operably linked to said DNA encoding said amino acids 1-29.

24. The Trichoderma host cell of claim 23, wherein said DNA further comprises the sequence of introns IVS1, IVS2 and IVS3 as shown in SEQ ID NO. 4 (FIG. 13), said introns being inserted between exons encoding said amino acids as shown in SEQ ID NO. 4 (FIG. 13).

25. The culture medium from the fermentation of a Trichoderma host cell that is transformed with a DNA molecule having a molecule sequence capable of being processed by said Trichoderma host cell to encode a protein, said protein comprising an amino acid sequence selected from the group consisting of:

a. amino acids 1-616 as shown in SEQ ID NO. 2 (FIG. 5A) or in SEQ ID NO. 4 (FIG. 13); and b. amino acids 30-616 as shown in SEQ ID NO. 2 (FIG. 5A) or in SEQ ID NO. 4 (FIG. 13);

said DNA molecule also having the sequence of introns IVS1, IVS2 and IVS3 as shown in SEQ ID NO. 4 (FIG. 13), said introns being inserted between exons encoding said amino acids as shown in SEQ ID NO. 4 (FIG. 13).

26. A method for producing glucoamylase P, wherein said method comprises expression of said glucoamylase P from Trichoderma, wherein said DNA encoding said glucoamylase P has a DNA sequence encoding, or capable of being processed by said Trichoderma host cell to encode, a protein, said protein comprising an amino acid sequence selected from the group consisting of:

a. amino acids 1-616 as shown in SEQ ID NO. 2 (FIG. 5A) or in SEQ ID NO. 4 (FIG. 13); and b. amino acids 30-616 as shown in SEQ ID NO. 2 (FIG. 5A) or in SEQ ID NO. 4 (FIG. 13).

27. The method of claim 26, wherein said Trichoderma is *T. reesei*.

28. The method of claim 26, wherein said DNA encoding glucoamylase P is *Hormoconis resinae* glucoamylase P DNA.

29. The method of claim 26, wherein said DNA contains the native *H. resinae* glucoamylase P introns and secretion signal.

30. The method of claim 26, wherein said glucoamylase P DNA encodes a protein comprising amino acids 30-616 as shown in SEQ ID NO. 2 (FIG. 5A) or in SEQ ID NO. 4 (FIG. 13).

31. The method of claim 26, wherein the sequence of said glucoamylase P DNA is that shown in SEQ ID NO. 1 (FIG. 5) or in SEQ ID NO. 4 (FIG. 13).

32. The method of claim 26, wherein said DNA comprises the promoter and terminator regions of a gene from Trichoderma operably linked to said DNA encoding said amino acid sequence.

33. The method of claim 32, wherein said promoter or said terminator are from the cbh1 gene.

34. The method of claim 26, wherein said Trichoderma is transformed with a vector selected from the group consisting of pALK602 and pALK612.

35. The method of any one of claims 26, 33 wherein said recombinant vector further comprises the sequence of introns IVS1, IVS2 and IVS3 as shown in SEQ ID NO. 4 (FIG. 13), said introns being inserted between exons encoding said amino acids as shown in SEQ ID NO. 4 (FIG. 13).

* * * * *